United States Patent [19]
Esser et al.

[11] Patent Number: 5,972,975
[45] Date of Patent: Oct. 26, 1999

[54] SUBSTITUTED 2-AMINOPYRIDINES AS INHIBITORS OF NITRIC OXIDE SYNTHASE

[75] Inventors: Craig Esser; William Hagmann; William Hoffman; Shrenik Shah; Kenny Wong; Renee Chabin; Ravindra Guthikonda; Malcolm Maccoss; Charles Caldwell; Philippe Durette, all of Rahway, N.J.

[73] Assignee: Merck & Co., Inc., Rahway, N.J.

[21] Appl. No.: 08/836,953

[22] PCT Filed: Dec. 8, 1995

[86] PCT No.: PCT/US95/16151
§ 371 Date: May 22, 1997
§ 102(e) Date: May 22, 1997

[87] PCT Pub. No.: WO96/18616
PCT Pub. Date: Jun. 20, 1996

[51] Int. Cl.[6] .......................... A61K 31/44; C07D 213/75
[52] U.S. Cl. .......................... 514/352; 514/211; 514/212; 514/218; 514/224.2; 514/226.5; 514/226.8; 514/228.2; 514/228.5; 514/230.5; 514/233.8; 514/234.2; 514/234.5; 514/248; 514/249; 514/254; 514/255; 514/256; 514/258; 514/266; 514/269; 514/299; 514/300; 514/301; 514/302; 514/303; 514/307; 514/310; 514/311; 514/313; 514/314; 514/334; 514/344; 514/346; 514/349; 540/544; 540/553; 540/575; 540/597; 544/48; 544/55; 544/61; 544/91; 544/96; 544/105; 544/119; 544/127; 544/236; 544/238; 544/277; 544/279; 544/333; 544/350; 544/405; 546/112; 546/113; 546/114; 546/115; 546/118; 546/119; 546/122; 546/143; 546/159; 546/257; 546/289; 546/292; 546/297; 546/304; 546/307; 546/308; 546/311

[58] Field of Search .......................... 514/230.5, 248, 514/255, 266, 269, 299, 300, 301, 307, 310, 311, 313, 314, 334, 344, 346, 349, 352, 211, 212, 218, 224.2, 226.5, 226.8, 228.2, 228.5, 233.8, 234.2, 234.5, 249, 254, 256, 258, 302, 303; 544/105, 277, 333, 350, 405, 48, 55, 61, 91, 96, 119, 127, 236, 238, 279; 546/112, 113, 114, 122, 143, 159, 257, 289, 292, 297, 304, 307, 308, 311, 115, 118, 119; 540/544, 553, 575, 597

[56] References Cited

U.S. PATENT DOCUMENTS

| | | | |
|---|---|---|---|
| 3,907,798 | 9/1975 | Lesher | 260/256.4 |
| 4,035,375 | 7/1977 | Gassman et al. | 260/294.8 |
| 4,209,620 | 6/1980 | Juby | 544/252 |
| 4,328,343 | 5/1982 | Vollhardt et al. | 546/145 |
| 4,386,209 | 5/1983 | McGill et al. | 546/311 |
| 4,405,552 | 9/1983 | Miesel | 424/263 |
| 5,290,943 | 3/1994 | Igarashi et al. | 546/309 |
| 5,629,322 | 5/1997 | Guthikonda et al. | 514/313 |

FOREIGN PATENT DOCUMENTS

3 332 687 A1  3/1985  Germany.

OTHER PUBLICATIONS

Vijn et al., Synthesis of 6–Substituted 2–(N–Acetylamino)pyridines and 2–Aminopyridines by Cyclization of 5–Oximinoalkanenitriles, Journal of Organic Chemistry, vol. 58, No. 4, pp. 887–891, Feb. 1993.

Kress et al., Selective Chlorinations in Sulfuric Acid. Synthesis of Some 2–Amino–5–chloro–, 2–Amino–3–chloro, and 2–Amino–3,5–dichloropyridines, Journal of Organic Chemistry, vol. 41, No. 1, pp. 93–96, Jan. 1976.

Primary Examiner—Mukund J. Shah
Assistant Examiner—Brenda Coleman
Attorney, Agent, or Firm—Richard C. Billups; Curtis C. Panzer; David L. Rose

[57] ABSTRACT

Substituted 2-aminopyridine compounds of Formula (I) and pharmaceutically acceptable salts which have been found useful in the treatment of nitric oxide synthase mediated diseases and disorders.

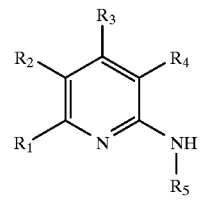

(I)

4 Claims, No Drawings

SUBSTITUTED 2-AMINOPYRIDINES AS INHIBITORS OF NITRIC OXIDE SYNTHASE

CROSS REFERENCE TO RELATED APPLICATIONS

This application is a U.S. national phase application filed under 35 U.S.C. 371 based upon PCT application No. PCT U.S. 95/16151, filed on Dec. 8, 1995, now lapsed, which was based upon U.S. application Ser. No. 08/353,860, filed on Dec. 12, 1994, now abandoned, priority of which is claimed hereunder.

BACKGROUND OF THE INVENTION

This application is directed to inhibitors of nitric oxide synthase, and in particular 2-aminopyridines.

Nitric Oxide in Biology

The emergence of nitric oxide (NO), a reactive, inorganic radical gas as a molecule contributing to important physiological and pathological processes is one of the major biological revelations of recent times. This molecule is produced under a variety of physiological and pathological conditions by cells mediating vital biological functions. Examples include endothelial cells lining the blood vessels; nitric oxide derived from these cells relaxes smooth muscle and regulates blood pressure and has significant effects on the function of circulating blood cells such as platelets and neutrophils as well as on smooth muscle, both of the blood vessels and also of other organs such as the airways. In the brain and elsewhere nitric oxide serves as a neurotransmitter in non-adrenergic non-cholinergic neurons. In these instances nitric oxide appears to be produced in small amounts on an intermittent basis in response to various endogenous molecular signals. In the immune system nitric oxide can be synthesized in much larger amounts on a protracted basis. Its production is induced by exogenous or endogenous inflammatory stimuli, notably endotoxin and cytokines elaborated by cells of the host defense system in response to infectious and inflammatory stimuli. This induced production results in prolonged nitric oxide release which contributes both to host defense processes such as the killing of bacteria and viruses as well as pathology associated with acute and chronic inflammation in a wide variety of diseases. The discovery that nitric oxide production is mediated by a unique series of three closely related enzymes, named nitric oxide synthases, which utilize the amino acid arginine and molecular oxygen as co-substrates has provided an understanding of the biochemistry of this molecule and provides distinct pharmacological targets for the inhibition of the synthesis of this mediator, which should provide significant beneficial effects in a wide variety of diseases.

Nitric Oxide Synthases

Nitric oxide and L-citrulline are formed from L-arginine via the dioxygenase activity of specific nitric oxide synthases (NOSs) in mammalian cells. In this reaction, L-arginine, $O_2$ and NADPH are co-substrates while FMN, FAD and tetrahydrobiopterin are co-factors. NOSs fall into two distinct classes, constitutive NOS (cNOS) and inducible NOS (iNOS). Two constitutive NOSs have been identified. They are:

(i) a constitutive, $Ca^{++}$/calmodulin dependent enzyme, located in the endothelium (ecNOS or NOS 3), that releases NO in response to receptor or physical stimulation, (ii) a constitutive, $Ca^{++}$/calmodulin dependent enzyme, located in the brain (ncNOS or NOS 1) and elsewhere, that releases NO in response to receptor or physical stimulation, The third isoform identified is inducible NOS (iNOS or NOS 2):

(iii) a $Ca^{++}$ independent enzyme which is induced after activation of vascular smooth muscle, macrophages, endothelial cells, and a large number of other cells by endotoxin and cytokines. Once expressed, this inducible NO synthase produces NO in relatively large amounts for long periods of time.

Spectral studies of both the mouse macrophage iNOS and rat brain ncNOS have shown that these enzymes (which have been classified as P-450-like enzymes from their CO-difference spectra) contain a heme moiety. The structural similarity between NOS and the P-450-flavoprotein complex suggests that the NOS reaction mechanism may be similar to P-450 hydroxylation and/or peroxidation. This indicates that NOS belongs to a class of flavohemeproteins which contain both heme and flavin binding regions within a single protein in contrast to the multiprotein NADPH oxidase or Cytochrome P-450/NADPH Cyt c reductase complexes.

Distinct Functions of NO Produced by Different Nitric Oxide Synthases

The NO released by the constitutive enzymes (NOS 1 and NOS 3) acts as an autocoid mediating a number of physiological responses. Two distinct cDNAs accounting for the activity of NOS 1 and NOS 3 in man have been cloned, one for NOS 1 (Nakane et al., *FEBS Letters*, 316, 175–182, 1993) which is present in the brain and a number of peripheral tissues, the other for an enzyme present in endothelium (NOS 3) (Marsden et al., *FEBS Letters*, 307, 287–293, 1992). This latter enzyme is critical for production of NO to maintain vasorelaxation. A second class of enzyme, iNOS or NOS 2, has been cloned from human liver (Geller et al., *PNAS*, 90, 3491–5, 1993), and identified in more than a dozen other cells and tissues, including smooth muscle cells, chondrocytes, the kidney and airways. As with its counterpart from the murine macrophage, this enzyme is induced upon exposure to cytokines such as gamma interferon (IFN-γ), interleukin-1β (IL-1β), tumor necrosis factor (TNF-α) and LPS (lipopolysaccharide). Once induced, iNOS expression continues over a prolonged period of time. The enzyme does not require exogenous calmodulin for activity.

Endothelium derived relaxation factor (EDRF) has been shown to be produced by NOS 3 (Moncada et al., *Pharmacol. Reviews*, 43, 109–142, 1991). Studies with substrate analog inhibitors of NOS have shown a role for NO in regulating blood pressure in animals and blood flow in man, a function attributed to NOS 3. NO has also been shown to be an effector of the cytotoxic effects of activated macrophages (Nathan, *FASEB J.*, 6, 3051–64, 1992) for fighting tumor cells and invading microorganisms (Wright et al., *Card. Res.*, 26 ,48–57, 1992 and Moncada et al., *Pharmacological Review*, 43, 109–142, 1991). It also appears that the adverse effects of excess NO production, in particular pathological vasodilation and tissue damage, may result largely from the effects of NO synthesized by the NOS 2.

NO generated by NOS 2 has been implicated in the pathogenesis of inflammatory diseases. In experimental animals hypotension induced by LPS or TNF-α can be reversed by NOS inhibitors and reinitiated by L-arginine (Kilbourn et al., *PNAS*, 87, 3629–32, 1990). Conditions which lead to cytokine-induced hypotension include septic shock, hemodialysis (Beasley and Brenner, *Kidney Int.*, 42, Suppl., 38, S96–S 100, 1992) and IL-2 therapy in cancer patients (Hibbs et al., *J. Clin. Invest.*, 89, 867–77, 1992). NOS 2 is implicated in these responses, and thus the possibility exists that a NOS inhibitor would be effective in ameliorating cytokine-induced hypotension. Recent studies in animal models have suggested a role for NO in the pathogenesis of inflammation and pain and NOS inhibitors have been shown to have beneficial effects on some aspects of the inflammation and tissue changes seen in models of inflammatory bowel disease, (Miller et al., *J. PhannacoL Exp. Ther.*, 264, 11–16, 1990) and cerebral ischemia and arthritis (Ialenti et al., *Br. J. Phannacol.*, 110, 701–6, 1993; Stevanovic-Racic et al., *Arth. & Rheum.*, 37, 1062–9, 1994). Moreover transgenic mice deficient in NOS 1 show diminished cerebral ischemia (Huang et al., *Science*, 265, 1883–5, 1994).

Further conditions where there is an advantage in inhibiting NO production from L-arginine include therapy with cytokines such as TNF, IL-1 and IL-2 or therapy with cytokine-inducing agents, for example 5, 6-dimethylxanthenone acetic acid, and as an adjuvant to short term immunosuppression in transplant therapy. In addition, compounds which inhibit NO synthesis may be of use in reducing the NO concentration in patients suffering from inflammatory conditions in which an excess of NO contributes to the pathophysiology of the condition, for example adult respiratory distress syndrome (ARDS) and myocarditis.

There is also evidence that an NO synthase enzyme may be involved in the degeneration of cartilage which takes place in autoimmune and/or inflammatory conditions such as arthritis, rheumatoid arthritis, chronic bowel disease and systemic lupus erythematosis (SLE). It is also thought that an NO synthase enzyme may be involved in insulin-dependent diabetes mellitus. Therefore, a yet further aspect of the present invention provides cyclic amidine derivatives or salts thereof in the manufacture of a medicament for use in cytokine or cytokine-inducing therapy, as an adjuvant to short term immunosuppression in transplant therapy, for the treatment of patients suffering from inflammatory conditions in which an excess of NO contributes to the pathophysiology of the condition.

SUMMARY OF THE INVENTION

The invention disclosed herein encompasses compounds of Formula (I)

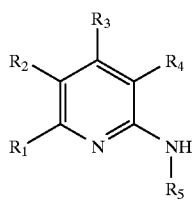

(I)

and pharmaceutically acceptable salts thereof which have been found to be useful in the treatment of nitric oxide synthase-mediated diseases and disorders, including neurodegenerative disorders, disorders of gastrointestinal motility and inflammation. These diseases and disorders include hypotension, septic shock, toxic shock syndrome, hemodialysis, IL-2 therapy such as in cancer patients, cachexia, immunosuppression such as in transplant therapy, autoimmune and/or inflammatory indications including sunburn, eczema or psoriasis and respiratory conditions such as bronchitis, asthma, oxidant-induced lung injury and acute respiratory distress (ARDS), glomerulonephritis, inflammatory sequelae of viral infections, myocarditis, heart failure, atherosclerosis, arthritis, rheumatoid arthritis, chronic or inflammatory bowel disease, ulcerative colitis, Crohn's disease, systemic lupus erythematosis (SLE), ocular conditions such as ocular hypertension, retinitis and uveitis, type 1 diabetes, insulin-dependent diabetes mellitus and cystic fibrosis. Compounds of Formula I are also useful in the treatment of hypoxia, hyperbaric oxygen convulsions and toxicity, dementia, Sydenham's chorea, Parkinson's disease, Huntington's disease, amyotrophic lateral sclerosis, mulitple sclerosis, Korsakoff's disease, imbecility related to cerebral vessel disorder, NO mediated cerebral trauma and related sequelae, ischemic brain edema, sleeping disorders, schizophrenia, depression, pre-menstrual syndrome (PMS), anxiety, drug addiction, pain, migraine, immune complex disease, as immunosupressive agents, acute allograft rejection, infections caused by invasive microorganisms which produce NO, radiocontrast induced renal failure and for preventing or reversing tolerance to opiates and diazepines.

DETAILED DESCRIPTION OF THE INVENTION

The invention disclosed herein encompasses compounds of Formula (I)

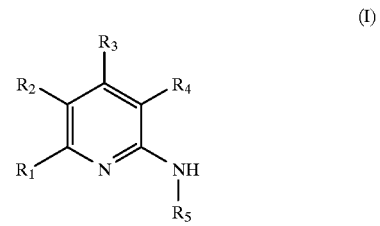

(I)

or a pharmaceutically acceptable salt thereof wherein:
$R_1$, $R_2$, $R_3$ and $R_4$ are each independently selected from the group consisting of
(a) hydrogen,
(b) hydroxy,
(c) amino,
(d) carboxyl,
(e) aminocarbonyl,
(f) cyano,
(g) nitro,
(h) halo, where halo is selected from fluoro, chloro, bromo, and iodo,
(i) trifluoromethyl,
(l) $C_{1-12}$alkyl,
(k) $C_{2-12}$alkenyl,
(l) $C_{2-12}$alkynyl,
(m) $C_{1-12}$alkoxy,
(n) $C_{1-12}$alkylcarbonyl,
(o) $C_{1-12}$alkoxycarbonyl,
(p) $C_{1-12}$alkylaminocarbonyl,
(q) mono- and di-$C_{1-12}$alkylamino,
(r) $C_{1-12}$alkylthio,
(s) aryl, where aryl is selected from phenyl and naphthyl,
(t) aryloxy, where aryl is selected from phenyl and naphthyl,
(u) arylthio, where aryl is selected from phenyl and naphthyl, (v) arylC$_{1-6}$alkyl, where aryl is selected from phenyl and naphthyl,
(w) cycloalkyl, wherein the cycloalkyl is a 5- to 10-membered monocyclic ring which optionally contains 1 or 2 heteroatoms selected from S, O, and N,
(x) heteroaryl, wherein heteroaryl is selected from the group consisting of:
  (1) pyridyl,
  (2) pyrrolyl,
  (3) furanyl,
  (4) thienyl,
  (5) isothiazolyl,
  (6) imidazolyl,
  (7) benzimidazolyl,
  (8) tetrazolyl,
  (9) pyrazinyl,
  (10) pyrimidyl,
  (11) quinolyl,
  (12) isoquinolyl,
  (13) benzofuranyl,
  (14) isobenzofuryl,
  (15) benzothienyl,
  (16) pyrazolyl,
  (17) pyrazinyl,
  (18) indolyl,
  (19) isoindolyl,
  (20) purinyl,
  (21) carbazolyl,
  (22) isoxazolyl,
  (23) thiazolyl,
  (24) triazolyl
  (25) oxazolyl,
  (26) oxadiazolyl,
  (27) thiadiazolyl
  (28) benzthiazolyl, and
  (29) benzoxazolyl,
(y) heteroarylC$_{1-6}$alkyl, where heteroaryl is defined above in item (x),
  each of (j) to (y) being optionally mono- or di-substituted, the substituents being independently selected from
    (1) hydroxy,
    (2) C$_{1-6}$alkyl,
    (3) C$_{1-6}$alkoxy,
    (4) amino,
    (5) mono- and di-C$_{1-6}$alkylamino,
    (6) carboxyl
    (7) C$_{1-6}$alkylthio,
    (8) —S(O)$_k$-C$_{1-3}$alkyl, where k is 1 or 2,
    (9) C$_{1-6}$alkoxycarbonyl,
    (10) halo selected from fluoro, chloro, bromo, and iodo,
    (11) oxo,
    (12) amidino,
    (13) guanidino,
R$_1$ and R$_2$, or R$_2$ and R$_3$ or R$_3$ and R$_4$ may be joined together to form a 5- to 10-membered saturated or unsaturated ring containing 0 to 2 heteroatoms which together with the atoms to which R$_1$ and R$_2$, or R$_2$ and R$_3$ or R$_3$ and R$_4$ are attached there is formed a bicyclic ring according to Formulae (IIa–IIc), the heteroatoms being selected from the group consisting of O, S and N,

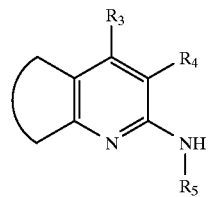

(IIa)

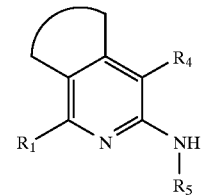

(IIb)

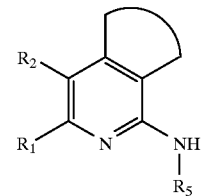

(IIc)

R$_5$ is selected from the group consisting of
  (a) hydrogen,
  (b) C$_{1-12}$alkyl,
  (c) C$_{2-12}$alkenyl,
  (d) C$_{2-12}$alkynyl,
  (e) aryl, wherein the aryl group is as defined above,
  (f) arylC$_{1-6}$alkyl, wherein the aryl group is as defined above,
  (g) heteroaryl, wherein heteroaryl is as defined above,
  (h) heteroarylC$_{1-6}$alkyl, wherein heteroaryl is as defined above,
  (i) cycloalkyl, wherein the cycloalkyl is a 5- to 10-membered monocyclic ring which optionally contains 1 or 2 heteroatoms selected from the group consisting of S, O and N,
  each of (b) to (i) being optionally mono- or di-substituted, the substituents being independently selected from
    (1) hydroxy,
    (2) C$_{1-6}$alkyl,
    (3) C$_{1-6}$alkoxy,
    (4) amino,
    (5) mono- and di-C$_{1-6}$alkylamino,
    (6) carboxyl
    (7) C$_{1-6}$alkylthio,
    (8) —S(O)$_k$-C$_{13}$alkyl, where k is 1 or 2,
    (9) C$_{1-6}$alkoxycarbonyl,
    (10) halo selected from fluoro, chloro, bromo, and iodo,
    (11) oxo,
    (12) amidino, and
    (13) guanidino,
with the proviso that R$_2$ is other than aryl, heteroaryl, arylC$_{1-4}$alkyl, heteroarylC1-4alkyl, aryl-S(O)$_k$ or heteroaryl-S(O)$_k$.

In an alternative aspect, this embodiment includes compounds wherein R2 may be aryl-S(O)$_k$ or heteroaryl-S(O)$_k$.
Within this embodiment there is the genus of compounds wherein $R_1$, $R_2$, $R_3$ and $R_4$ are each independently selected from the group
consisting of
- (a) hydrogen,
- (b) hydroxy,
- (c) amino,
- (d) cyano,
- (e) fluoro, chloro, bromo, and iodo,
- (f) trifluoromethyl,
- (g) $C_{1-6}$alkyl,
- (h) $C_{1-6}$alkoxy,
- (i) $C_{1-6}$alkylthio,
- (j) $C_{1-6}$alkylcarbonyl,
- (k) mono- and di-$C_{1-6}$alkylamino,
- (l) aryl, where aryl is phenyl and naphthyl,
- (m) aryloxy, where aryl is phenyl and naphthyl,
- (n) cycloalkyl, wherein the cycloalkyl is a 5-, 6-, or 7-membered monocyclic ring which optionally contains 1 or 2 heteroatoms selected from S, O, and N,
- (o) heteroaryl, wherein heteroaryl is selected from the group consisting of:
  - (1) pyridyl,
  - (2) furanyl,
  - (3) thienyl,
  - (4) pyrazinyl,
  - (5) pyrimidyl,
  - (6) thiazolyl, and
  - (7) triazolyl, each of (g) to (o) being optionally mono- or di-substituted, the substituents being independently selected from
  - (1) hydroxy,
  - (2) $C_{1-4}$alkyl,
  - (3) $C_{1-3}$alkoxy,
  - (4) $C_{1-3}$alkylthio,
  - (5) mono- and di-$C_{1-3}$alkylamino,
  - (7) —S(O)$_k$-$C_{1-3}$alkyl, where k is 1 or 2,
  - (8) —C(O)-O-$C_{1-3}$alkyl,
  - (9) halo selected from fluoro, chloro and bromo,
  - (10) amino,
  - (11) carboxyl, $R_1$ and $R_2$, or $R_2$ and $R_3$ or $R_3$ and $R_4$ may be joined together to form a 5-, 6- or 7-membered saturated monocyclic ring containing 0, 1 or 2 heteroatoms which together with the atoms to which $R_1$ and $R_2$, or $R_2$ and $R_3$ or $R_3$ and $R_4$ are attached there is formed a bicyclic ring according to Formulae (IIa–IIc), the heteroatoms being selected from the group consisting of O, S and N,

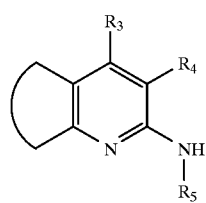

(IIa)

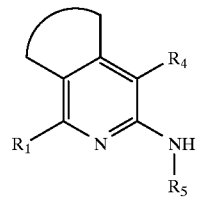

(IIb)

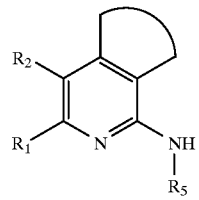

(IIc)

$R_5$ is selected from the group consisting of
- (a) hydrogen,
- (b) $C_{1-6}$alkyl,
- (c) aryl, wherein the aryl group is phenyl and naphthyl,
- (d) aryl$C_{1-6}$alkyl, wherein the aryl group is phenyl and naphthyl,
- (e) heteroaryl, wherein heteroaryl is as defined above,
- (f) heteroaryl$C_{1-6}$alkyl, wherein heteroaryl is as defined above,
- (g) cycloalkyl, wherein the cycloalkyl is a 5-, 6-, or 7-membered monocyclic ring which optionally contains 1 or 2 heteroatoms selected from S, O, and N, each of (b) to (g) being optionally mono- or di-substituted, the substituents being independently selected from
  - (1) hydroxy,
  - (2) $C_{1-4}$alkyl,
  - (3) $C_{1-3}$alkoxy,
  - (4) $C_{1-3}$alkylthio,
  - (5) mono- and di-$C_{1-3}$alkylamino,
  - (7) —S(O)$_k$-$C_{1-3}$alkyl, where k is 1 or 2,
  - (8) —C(O)-O-$C_{1-3}$alkyl,
  - (9) halo selected from fluoro, chloro and bromo.

Within this genus there is a class of compounds wherein $R_1$, $R_2$, $R_3$ and $R_4$ are each independently selected from the group consisting of
- (a) hydrogen,
- (b) hydroxy,
- (c) amino,
- (d) cyano,
- (e) fluoro, chloro or bromo,
- (f) trifluoromethyl,
- (g) $C_{1-6}$alkyl,
- (h) $C_{1-6}$alkoxy,
- (i) $C_{1-6}$alkylthio,
- (j) mono- and di-$C_{1-4}$alkylamino, $R_1$ and $R_2$, or $R_2$ and $R_3$ or $R_3$ and $R_4$ may be joined together to form a 5-, 6- or 7-membered saturated monocyclic ring containing 0, 1 or 2 heteroatoms which together with the atoms to which $R_1$ and $R_2$, or $R_2$ and $R_3$ or $R_3$ and $R_4$ are attached there is formed a bicyclic ring according to Formulae (IIa–IIc), the heteroatoms being selected from the group consisting of O, S and N,

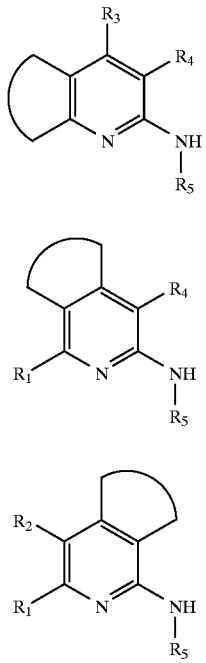

(IIa)

(IIb)

(IIc)

$R_5$ is selected from the group consisting of
(a) hydrogen,
(b) $C_{1-4}$alkyl,
(c) phenyl,
(d) phenyl$C_{1-4}$alkyl,
(e) heteroaryl, wherein heteroaryl is selected from,
  (1) pyridyl,
  (2) furanyl,
  (3) thienyl,
  (4) pyrazinyl,
  (5) pyrimidyl,
  (6) thiazolyl, and
  (7) triazolyl,
(f) heteroaryl$C_{1-6}$alkyl, wherein heteroaryl is defined as above,
(g) cycloalkyl, wherein the cycloalkyl is a 5-, 6-, or 7-membered monocyclic ring which optionally contains 1 or 2 heteroatoms selected from S, O, and N,
  each of (b) to (g) being optionally mono- or disubstituted, the substituents being independently selected from
  (1) hydroxy,
  (2) $C_{1-4}$alkyl,
  (3) $C_{1-3}$alkoxy,
  (4) $C_{1-3}$alkylthio,
  (5) mono- and di-$C_{1-3}$alkylamino,
  (7) —S(O)$_k$-$C_{1-3}$alkyl, where k is 1 or 2,
  (8) —C(O)-O-$C_{1-3}$alkyl,
  (9) halo selected from fluoro, chloro and bromo.

Within this class is the subclass of compounds wherein the rings of Formulae IIa, IIb and IIc are selected from the group consisting of

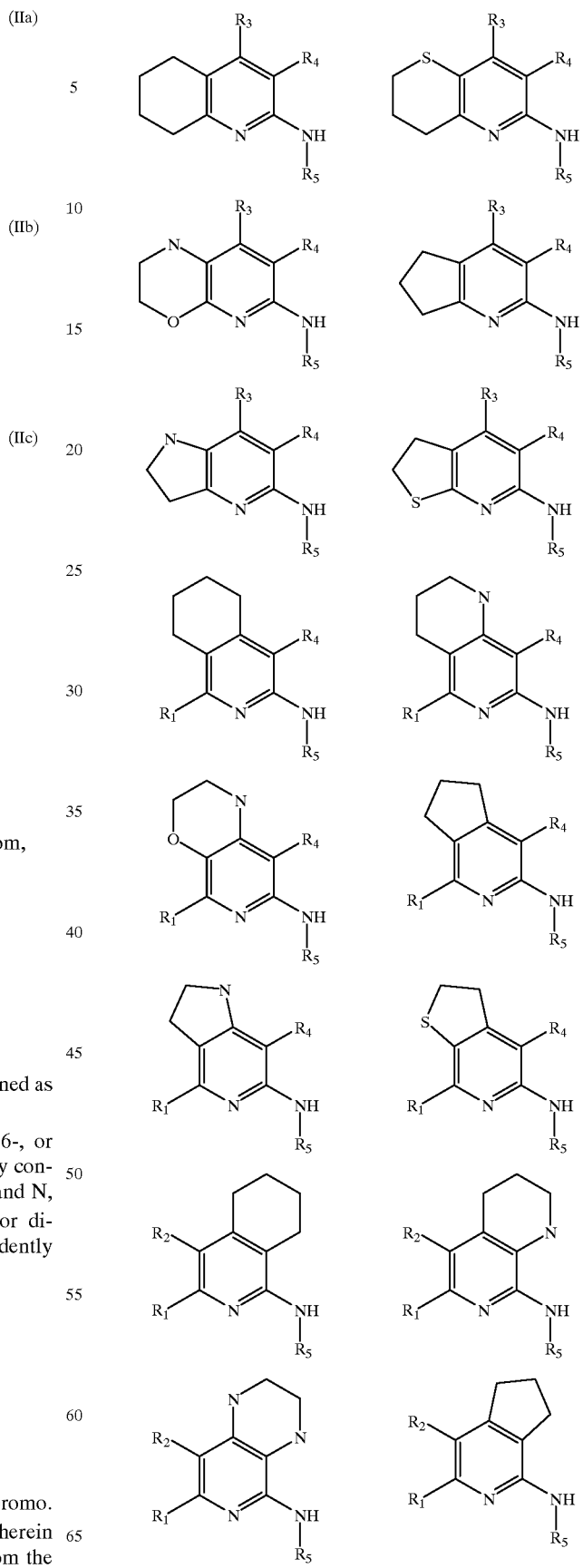

-continued

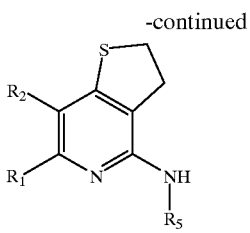
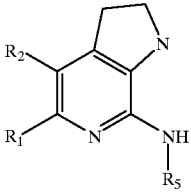

Within the above subclass of compounds are the compounds of Formulae IIa, IIb, and IIc wherein $R_1$, $R_2$, $R_3$ and $R_4$, as explicitly shown, are each independently selected from the group consisting of
(a) hydrogen,
(b) hydroxy,
(c) amino,
(d) cyano,
(e) fluoro, chloro or bromo,
(f) trifluoromethyl,
(g) $C_{1-4}$alkyl,
(h) $C_{1-4}$alkoxy,
(i) $C_{1-4}$alkylthio,
(j) mono- and di-$C_{1-4}$alkylamino,
$R_5$ is selected from the group consisting of
(a) hydrogen,
(b) $C_{1-4}$alkyl,
(c) phenyl,
(d) phenyl$C_{1-4}$alkyl,
(e) heteroaryl, wherein heteroaryl is selected from,
  (1) pyridyl,
  (2) furanyl,
  (3) thienyl,
  (4) pyrazinyl,
  (5) pyrimidyl,
  (6) thiazolyl, and
  (7) triazolyl,
(f) heteroaryl$C_{1-6}$alkyl, wherein heteroaryl is defined as above,
(g) cycloalkyl, wherein the cycloalkyl is a 5-, 6-, or 7-membered monocyclic ring which optionally contains 1 or 2 heteroatoms selected from S, O, and N, each of (b) to (g) being optionally mono- or di-substituted, the substituents being independently selected from
  (1) hydroxy,
  (2) $C_{1-4}$alkyl,
  (3) $C_{1-3}$alkoxy,
  (4) $C_{1-3}$alkylthio,
  (5) mono- and di-$C_{1-3}$alkylamino,
  (7) —S(O)$_k$-$C_{1-3}$alkyl, where k is 1 or 2,
  (8) —C(O)-O-$C_{1-3}$alkyl,
  (9) halo selected from fluoro, chloro and bromo.
Illustrating the invention are the following compounds:
(a) 2-amino-3-benzylurea-4-picoline,
(b) 2-amino-3-methoxypyridine,
(c) 2-amino-3-methylthio-4-picoline,
(d) 2-amino-4-methylthiomethylpyridine,
(e) 2-amino-3-hydroxymethyl-4-picoline,
(f) 2-amino-3-ethyl-4-picoline dihydrochloride,
(g) 2-amino-3-methoxymethyl-4-picoline dihydrochloride,
(h) 2-amino-3-n-propyl-4-picoline dihydrochloride,
(i) 2-amino-3-dimethylamino-4-picoline trihydrochloride,
(j) 2-amino-3-chloro-4-picoline,
(k) 2-amino-5-chloro-4-picoline,
(l) 2,5-diamino-4-picoline,
(m) 5-acetylamino-2-amino-4-picoline,
(n) 2-amino-5-ethynyl-4-methyl-pyridine,
(o) 2-amino-4-methyl-5-pentyl-pyridine,
(p) 4-methylthio-2-aminopyridine,
(q) 4-chloro-6-methoxycarbonyl-2-aminopyridine,
(r) 4,6-dimethyl-5-ethenyl-2-aminopyridine,
(s) 2,4-diaminopyridine dihydrochloride,
(t) 2-amino-5-phenylpyridine,
(u) 2-amino-4-methyl-5-phenylpyridine,
(v) 2-amino-5-bromo-4-methylpyridine,
(w) 2-amino-5-cyano-4-methylpyridine,
(x) 2-amino-5-carboxy-4-methylpyridine,
(y) 2-amino-5-methoxycarbonyl-4-methylpyridine,
(z) 2-amino-5-aminomethyl-4-methylpyridine dihydrochloride,
(aa) 2-amino-5-acetamidomethyl-4-methylpyridine,
(ab) 2-amino-5-hydroxymethyl-4-methylpyridine,
(ac) 2-(2-amino-3-pyridinoxy)-ethyl-(S)-glycine dihydrochloride,
(ad) 2-amino-4,5-dimethylpyridine hydrochloride,
(ae) 2-amino-6-(3-buten-1-yl)-4-methylpyridine,
(af) 2-amino-6-ethyl-4-methylpyridine,
(ag) 2-amino-4-methyl-6-(1-methylethyl)pyridine,
(ah) 2-amino-6-(4-aminobutyl)-4-methylpyridine,
(ai) 6-(4-acetamidobutyl)-2-amino-4-methylpyridine,
(aj) 2-amino-6-(2-hydroxyethyl)-4-methylpyridine,
(ak) α-(2-(6-amino-4-methylpyrid-2-yl) ethyl)glycine dihydrochloride,
(al) 2-amino-5-ethylpyridine,
(am) 2-amino-6-benzylpyridine,
(an) 2-amino-6,7-dihydro-(5H)-pyrindine,
(ao) 2-amino-6-(3-aminopropyl)-4-methylpyridine,
(ap) 2-amino-6-(2-aminoethyl)-4-methylpyridine,
(aq) 2-amino-4-methyl-6-propylpyridine,
(ar) 2-amino-4-methyl-6-(3-phenylpropyl)pyridine,
(as) 2-amino-4-methyl-6-(4-phenylbutyl)pyridine,
(at) 2-amino-4-methyl-6-(3-methylbutyl)pyridine,
(au) 2-amino-4-methyl-6-(2-methylpropyl)pyridine,
(av) 2-amino-4-methyl-6-(2-phenylethyl)pyridine,
(aw) 5-(6-amino-4-methyl-2-pyridinyl)pentanoic acid hydrochloride,
(ax) 4-(6-amino-4-methyl-2-pyridinyl)butanoic acid hydrochloride,
(ay) (S)-2-amino-6-(3-aminobutyl)-4-methylpyridine, or
(az) (R)-2-Amino-6-(3-aminobutyl)-4-methylpyridine, or a pharmaceutically acceptable salt thereof.

For purposes of this specification alkyl is defined to include linear, branched, and cyclic structures, with $C_{1-6}$alkyl including methyl, ethyl, propyl, 2-propyl, s- and t-butyl, butyl, pentyl, hexyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like. Likewise, $C_{1-6}$ alkylthio is intended to include alkylthio groups of from 1 to 6 carbon atoms of a straight, branched or cyclic configuration. Examples of lower alkylthio groups include methylthio, propylthio, isopropylthio, cycloheptylthio, etc. By way of illustration, the propylthio group signifies —$SCH_2CH_2CH_3$.

Heteroaryl includes but is not limited to, pyridyl, pyrrolyl, furanyl, thienyl, isothiazolyl, imidazolyl, benzimidazolyl, tetrazolyl, pyrazinyl, pyrimidyl, quinolyl, isoquinolyl, benzofuranyl, isobenzofuryl, benzothienyl, pyrazolyl, pyridazinyl, indolyl, isoindolyl, purinyl, carboxazolyl, isoxazolyl, thiazolyl, triazolyl, oxazolyl, oxadiazolyl, thiadiazolyl, benzthiazolyl and benzoxazolyl.

As outlined in the summary of the invention, the compounds of the instant invention are useful for in the treatment of a number of NOS implicated diseases. The implication of these diseases is well documented in the literature. For example, with regard to psoriasis, see Ruzicka et al., J. Invest. Derm., 103: 397 (1994) or Kolb-Bachofen et al., Lancet, 344: 139 (1994) or Bull, et al., J. Invest. Derm., 103:435(1994); with regard to uveitis, see Mandia et al., Invest Opthalmol., 35: 3673–89 (1994); with regard to type 1 diabetes, see Eisieik & Leijersfam, Diabetes & Metabolism, 20: 116–22 (1994) or Kroncke et al., BBRC, 175: 752–8 (1991) or Welsh et al., Endocrinol, 129: 3167–73 (1991); with regard to septic shock, see Petros et al., Lancet, 338: 1557–8 (1991),Thiemermann & Vane, Eur. J. Pharmacol., 211: 172–82 (1992), or Evans et al., Infec. Imm., 60: 4133–9 (1992), or Schilling et al., Intensive Care Med., 19: 227–231 (1993); with regards to pain, see Moore et al., Brit. J. Pharmacol., 102: 198–202 (1991), or Moore et al, Brit. J. Pharmacol., 108: 296–97 (1992) or Meller et al., Europ. J. Pharnacol., 214: 93–6 (1992) or Lee et al., NeuroReport, 3: 841–4 (1992); with regard to migraine, see Olesen et al., TIPS, 15: 149–153 (1994); with regard to rheumatoid arthritis, see Kaurs & Halliwell, FEBS Letters, 350: 9–12 (1994); with regard to osteoarthritis, see Stadler et al., J. Immunol., 147: 3915–20 (1991); with regard to inflammatory bowel disease, see Miller et al., Lancet, 34: 465–66 (1993) or Miller et al., J. Pharmacol. Exp. Ther., 264: 11–16 (1993); with regard to asthma, see Hamid et al., Lancet, 342: 1510–13 (1993) or Kharitonov, et al., Lancet, 343: 133–5 (1994); with regard to Immune complex diseases, see Mulligan et al., Br. J. Pharmacol., 107: 1159–62 (1992); with regard to multiple sclerosis, see Koprowski et al., PNAS, 90: 3024–7 (1993); with regard to ischemic brain edema, see Nagafuji et al., Neurosci., 147: 159–62 (1992) or Buisson et al., Br. J. Pharmacol., 106: 766–67 (1992) or Trifiletti et al., Europ. J. Pharmacol., 218: 197–8 (1992); with regard to toxic shock syndrome, see Zembowicz & Vane, PNAS, 89: 2051–55 (1992); with regard to heart failure, see Winlaw et al., Lancet, 344: 373–4 (1994); with regard to ulcerative colitis, see Boughton-Smith et al., Lancet 342: 338–40 (1993); and with regard to atherosclerosis, see White et al., PNAS, 91: 1044–8 (1994); with regard to glomerulonephritis, see Mühl et al., Br. J. Pharmcol., 112: 1–8 (1994); with regard to paget's disease and osteoporosis, see Löwick et al., J. Clin. Invest., 93: 1465–72 (1994); with regard to inflammatory sequelae of viral infections, see Koprowski et al., PNAS, 90: 3024–7 (1993); with regard to retinitis, see Goureau et al., BBRC, 186: 854–9 (1992); with regard to oxidant induced lung injury, see Berisha et al., PNAS, 91: 744–9 (1994); with regard to eczema, see Ruzica, et al., J. Invest. Derm., 103:395(1994); with regard to acute allograft rejection, see Devlin, J. et al., Transplantation, 58:592–595 (1994); with regard to infection caused by invasive microorganisms which produce NO, see Chen, Y and Rosazza, J. P. N., Biochem. Biophys. Res. Comm., 203:1251–1258(1994), and with regard to radiocontrast induced renal failure, see Schwaartz, et al., Am. J. Physiol, 267:F374–9 (1994).

It will be understood that in the discussion of methods of treatment which follows, references to the compounds of Formula I are meant to also include the pharmaceutically acceptable salts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Isolation and Purification of Nitric Oxide Synthases

Methods demonstrating the isolation and purification of all three isoforms of NOS have been published and reviewed in U. Forstermann, J. S. Pollock, W. R. Tracey, M. Nakane in *Methods in Enzymology*, Vol. 233, L. Packer, ed., Academic Press, N.Y., 1994, Ch.26, pp. 258–264. Cloned and expressed NOS has also been demonstrated and reviewed in C. J Lowenstein and S. H. Snyder in *Methods in Enzymology*, Vol. 233, L. Packer, ed., Academic Press, N.Y., 1994, Ch.26, pp. 264–269.

Assay Protocol for NOS activity

Various assays for NOS activity have been reported in the literature and are reviewed in the following: M. E. Murphy and E. Noack in *Methods in Enzymology*, Vol. 233, L. Packer, ed., Academic Press, N.Y., 1994, Ch.26, pp. 240–250 and J. M. Hevel and M. A. Marletta in *Methods in Enzymology*, Vol. 233, L. Packer, ed., Academic Press, N.Y., 1994, Ch.26, pp. 250–258. Details for the assay protocols to measure NOS activity are as follows:

NOS activity is measured as the formation of L-[2,3,4,5-$^3$H]Citrulline from L-[2,3,4,5-$^3$H]Arginine. The incubation buffer (100 μL) contained; 100 mM TES, pH 7.5, 5 μM FAD, 5 μM FMN, 10 μM BH$_4$, 0.5 mM NADPH, 0.5 mM DTT, 0.5 mg/mL BSA, 2 mM CaCl2, 10 μg/mL calmodulin (bovine), 1 μM L-Arg, 0.2 μCi L-[2,3,4,5-$^3$H]Arg, and the inhibitor in aqueous DMSO (max. 5%). The reaction is initiated by addition of enzyme. Incubations are performed at room temperature for 30 minutes and stopped by the addition of an equal volume of quenching buffer consisting of 200 mM sodium citrate, pH 2.2, 0.02% sodium azide. Reaction products are separated by passing through a cation exchange resin and quantitated as cpm by scintillation counting. Percent inhibition is calculated relative to enzyme incubated without inhibitor according to: % inhibition=100× (cpm L-[2,3,4,5-$^3$H]Cit with inhibitor/cpm L-[2,3,4,5-$^3$H] Cit without inhibitor).

Illustrative of the utility of the compounds of Formula I is the ability of such compounds to inhibit NO synthase as shown in Tables 1 and 2 and as measured by the assay described above:

TABLE 1

Inhibition of Nitric Oxide Synthases by Substituted 2-Aminopyridines

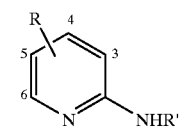

| Example Number | R | R' | iNOS (IC$_{50}$, uM) | ecNOS (IC$_{50}$, uM) | ncNOS (IC$_{50}$, uM) |
|---|---|---|---|---|---|
| 1 | H | H | 1.4 | <10 | <10 |
| 2 | 3-CH$_3$ | H | 3.4 | 1.2 | — |

TABLE 1-continued

Inhibition of Nitric Oxide Synthases by Substituted 2-Aminopyridines

| Example Number | R | R' | iNOS (IC$_{50}$, uM) | ecNOS (IC$_{50}$, uM) | ncNOS (IC$_{50}$, uM) |
|---|---|---|---|---|---|
| 3 | 4-CH$_3$ | H | 0.11 | 0.076 | <1 |
| 4 | 5-CH$_3$ | H | 1.3 | 3.1 | — |
| 5 | 6-CH$_3$ | H | 2.0 | 0.82 | — |
| 6 | 4,6-(CH$_3$)$_2$ | H | 0.108 | — | — |
| 7 | 4-C$_2$H$_5$ | H | 0.23 | — | — |
| 8 | 4-CF$_3$ | H | 13.2 | 73 | — |
| 9 | 3-OH | H | 47.5 | >50 | >50 |
| 10 | 3-NH$_2$ | H | <10 | 1.9 | — |
| 11 | 4-Ph | H | >50 | — | — |
| 12 | 4-CH$_2$Ph | H | >50 | — | — |
| 13 | 3,4-(CH$_3$)$_2$ | H | 0.076 | <1 | — |
| 14 | 4-t-C$_4$H$_9$ | H | >50 | — | — |
| 15 | 4-Cl | H | <1 | <10 | <10 |
| 16 | 4-CN | H | >50 | — | — |
| 17 | 3-NH$_2$-4-CH$_3$ | H | 0.058 | 0.081 | — |
| 18 | 4-CH$_3$ | CH$_2$Ph | 2.4 | <50 | — |

TABLE 2

Inhibition of Nitric Oxide Synthases by Substituted 2-Aminopyridines

| Example Number | iNOS (IC$_{50}$, uM) | ecNOS (IC$_{50}$, uM) | ncNOS (IC$_{50}$, uM) |
|---|---|---|---|
| 19 | <10 | >50 | >50 |
| 20 | >50 | <50 | <50 |
| 21 | <50 | <50 | <10 |
| 22 | <50 | >50 | >50 |
| 23 | <1 | <1 | — |
| 24 | <10 | <10 | — |
| 25 | <10 | <50 | <50 |
| 26 | <50 | — | — |
| 27 | <50 | >50 | <50 |
| 28 | <1 | <10 | <10 |
| 29 | <10 | <50 | <50 |
| 30 | <10 | <50 | <50 |
| 31 | <10 | <50 | <50 |
| 32 | <10 | <50 | <50 |
| 33 | <50 | >50 | <10 |
| 34 | <10 | <10 | <10 |
| 35 | <50 | <50 | <10 |
| 36 | <50 | >50 | >50 |
| 37 | <10 | <10 | <1 |
| 38 | <10 | <50 | <50 |
| 39 | >50 | — | — |
| 40 | >50 | — | — |
| 41 | <10 | <10 | <10 |
| 42 | >50 | — | — |
| 43 | >50 | >50 | >50 |
| 44 | >50 | — | — |
| 45 | <10 | <10 | <50 |
| 46 | <10 | >50 | >50 |
| 47 | <10 | — | — |
| 48 | <50 | <10 | <50 |
| 49 | <1 | <1 | <1 |
| 50 | <50 | <10 | <10 |
| 51 | <10 | <10 | <10 |
| 52 | <1 | <1 | <1 |
| 53 | <1 | <1 | <1 |
| 54 | <1 | <1 | <1 |
| 55 | <1 | <1 | <10 |
| 56 | <1 | <10 | <1 |
| 57 | <10 | <10 | <1 |
| 58 | <1 | <1 | <1 |

TABLE 2-continued

Inhibition of Nitric Oxide Synthases by Substituted 2-Aminopyridines

| Example Number | iNOS (IC$_{50}$, uM) | ecNOS (IC$_{50}$, uM) | ncNOS (IC$_{50}$, uM) |
|---|---|---|---|
| 59 | <1 | <1 | <1 |
| 60 | <10 | <50 | — |
| 61 | <50 | >50 | <50 |
| 62 | >50 | >50 | >50 |
| 63 | <10 | <50 | <10 |
| 64 | <10 | — | — |
| 65 | <50 | <50 | <50 |
| 66 | <1 | <10 | <1 |
| 67 | <1 | <50 | <1 |
| 68 | <1 | <10 | <1 |
| 69 | <50 | <50 | <10 |
| 70 | <10 | <10 | <10 |
| 71 | <1 | <10 | <1 |
| 72 | <1 | <1 | <1 |
| 73 | <10 | <10 | <10 |
| 74 | <10 | <1 | <10 |
| 75 | <10 | <1 | <10 |
| 76 | <1 | <10 | <1 |
| 77 | <10 | <50 | <1 |
| 78 | <10 | — | — |
| 79 | <10 | <10 | <10 |
| 80 | >50 | — | — |

Synthesis of 2-Aminopyridines

Several methods for preparing the compounds of this invention are illustrated in the following schemes and examples. Some of the compounds are known in the literature and are commercially available. Several reviews for the preparation of 2-aminopyridine derivatives have appeared (M. T. Leffler in *Organic Reactions*, Vol. 1, R. Adams, ed., J. Wiley and Sons, N.Y., 1942, Ch. 4, pp. 91–104; A. S. Tomcufcik and L. N., Starker in *The Chemistry of Heterocyclic Compounds, Pyridine and Its Derivatives, Part* 3, E. Klingsberg, ed.; Interscience, N.Y., 1962, Ch. IX, pp. 1–177; E. F. V. Scriven in *Comprehensive Heterocyclic Chemistry*, Vol. 2, Part 2A, A. J. Boulton and A. McKillop, eds., Pergamon Press, N.Y., 1984, Ch. 2.05, pp. 165–314). A limited class of substituted 2-aminopyridine derivatives have been reported to be specific inhibitors of the neuronal constitutive nitric oxide synthase (NOS-1) (PCT WO 94/14780).

In one method illustrated in Scheme 1, these compounds are prepared by the Chitchibabin reaction involving the reaction of a substituted pyridine derivative with sodium amide or sodium amide in the presence of a substituted amine to yield a 2-aminopyridine derivative. This methodology is amenable to a broad range of substitutents. The pyridine and substituted amine starting materials are commercially available or they can be prepared by the methods known to those skilled in the art.

SCHEME 1

Chitchibabin Reaction

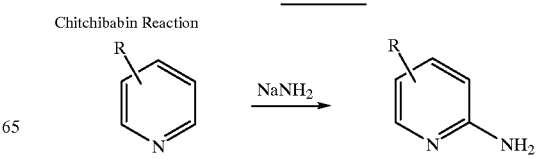

-continued

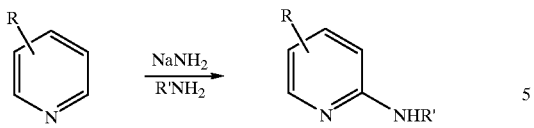

As shown in Scheme 2, the Hofmann rearrangement of a pyridyl-2-carboxamide in the presence of a hypohalite will give a 2-aminopyridine. Similarly, a Curtius rearrangement of a pyridyl-2-hydrazide will also give the desired derivative. Similarly, a Lossen rearrangement of a pyridyl-2-hydroxamic acid will also afford 2-aminopyridine. Similarly, treatment of a 2-pyridyl-hydroxamate-O-sulfonic acid with acid gives 2-aminopyridine (Neber-type rearrangement). Picolinic acid starting materials are commercially available or they can be prepared by the methods known to those skilled in the art. [see E. P. Oliveto in *The Chemistry of Heterocyclic Compounds, Pyridine and Its Derivatives, Part* 3, E. Klingsberg, ed.; Interscience, N.Y., 1962, Ch. X, pp. 179–346.]

SCHEME 2.

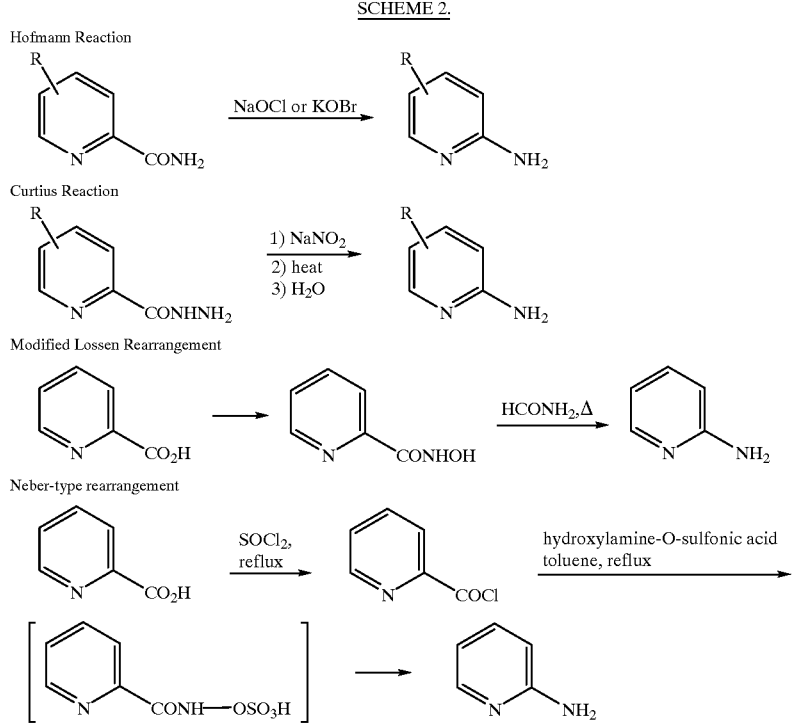

As outlined in Scheme 3, 2-halopyridines can be reacted with ammonia or substituted amines in the presence of copper(II) sulfate to form the 2-aminopyridine derivative. The preparation of a variety of 2-halopyridine derivatives has been reviewed (see H. E. Mertel in *The Chemistry of Heterocyclic Compounds, Pyridine and Its Derivatives, Part* 2 E. Klingsberg, ed.; Interscience, N.Y., 1962, Ch. VI, pp. 299–419). A recent publication describes new methodology for the preparation of highly functionalized 2-halopyridine derivatives (see P. Rocca et al., *J. Org. Chem.* 1993, 58, 7832–7838).

Displacement of a 2-trifluoromethyl group with sodium amide in liquid ammonia also gives 2-aminopyridine.

SCHEME 3

2-Halogen Displacement (where X is a halogen)

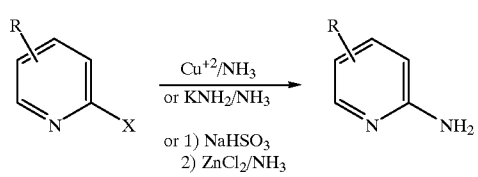

More recent methodology for the synthesis of 2-aminopyridine derivatives has recently been described (K. Wachi and A. Terada, *Chem. Pharm. Bull. Jap.*, 1980, 28, 465–472) and is outlined in Scheme 4. Pyridine-N-oxides can react with the imidoyl chloride of 1,3-benzoxazine to give N-(2-pyridyl)-1,3-benzoxazines. Subsequent treatment with strong acid affords the 2-aminopyridine.

SCHEME 4

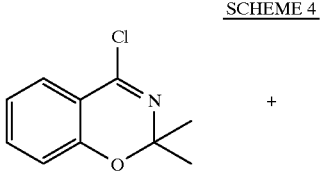

+

-continued

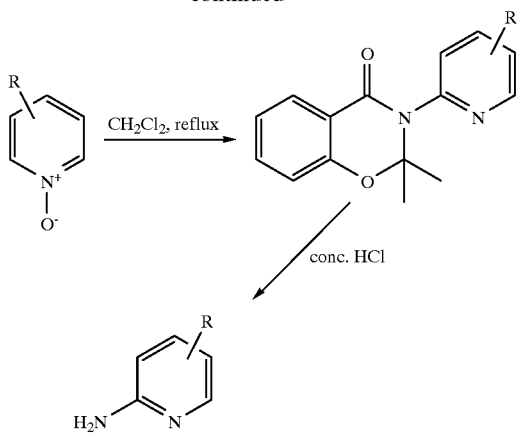

A procedure for the selective alkylation of 2-amino-4,6-dimethylpyridine is outlined in Scheme 5. 2-Amino-4,6-dimethylpyridine A is reacted with acetylacetone with the removal of water to form pyridylpyrrole B. Reaction of B with one equivalent of n-butyllithium (or phenyllithium) forms the anion on the 6-methyl group which is subsequently reacted with an electrophile R-X to form C. The pyrrole protecting group is subsequently removed by reaction with hydroxylamine hydrochloride in refluxing aqueous ethanol to form the 6-substituted product D.

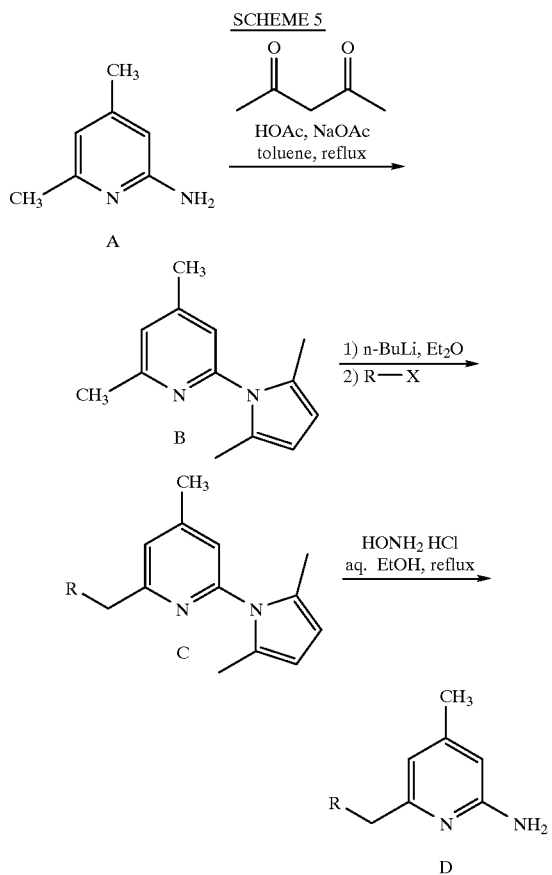

The invention will now be illustrated by the following non-limiting examples in which, unless stated otherwise.

All operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLES 1–12

The following compounds were obtained from commercial sources:

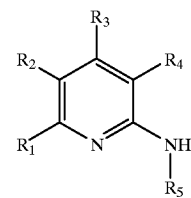

(I)

| Example | $R_1$ | $R_2$ | $R_3$ | $R_4$ | $R_5$ | Source[a] |
|---------|-------|-------|-------|-------|-------|-----------|
| 1 | H | H | H | H | H | Aldrich |
| 2 | H | H | H | $CH_3$ | H | Aldrich |
| 3 | H | H | $CH_3$ | H | H | Aldrich |
| 4 | H | $CH_3$ | H | H | H | Aldrich |
| 5 | $CH_3$ | H | H | H | H | Aldrich |
| 6 | $CH_3$ | H | $CH_3$ | H | H | Aldrich |
| 7 | H | H | $C_2H_5$ | H | H | SYNCHEM. |
| 8 | H | H | $CF_3$ | H | H | Fluorochem. |
| 9 | H | H | H | OH | H | Aldrich |
| 10 | H | H | H | $NH_2$ | H | Aldrich |
| 11 | H | H | phenyl | H | H | SPECS. |
| 12 | H | H | —$CH_2$-phenyl | H | H | Aldrich |

[a]Aldrich = Aldrich Chemical Co.; SYNCHEM = Synthetic Chemicals Ltd.; Fluorochem. = Fluorochemicals Ltd.; SPECS = Specialty Chemical Services B.V.

EXAMPLE 13

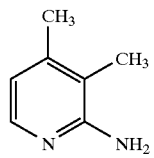

2-Amino-3,4-dimethylpyridine

The title compound was prepared by the method of W. O. Siegl (*J. Heterocyclic. Chem.*, 18, 1613 (1981)). N,N-Dimethylaniline (24 mL, 0.186 mol) was added to a solution of 3,4-dimethylpyridine (10 gm, 94 mmol) and sodium amide (4 gm, 100 mmol). The mixture was heated to 150° C. for 7 h under an inert atmosphere. After cooling to room temperature, the reaction mixture was poured into ice (400 mL). The organic layer was separated and dried over potassium carbonate. Fractional distillation in vacuo gave a mixture of 2-amino-3,4-dimethylpyridine and 2-amino-4,5-dimethylpyridine (bp. 114–8° C. /8 mm). Fractionional crystallization from heptane-benzene gave 2-amino-3,4-dimethylpyridine (mp. 82° C.).

Repeated fractional crystallization of the mother liquors afforded 2-amino-4,5-dimethylpyridine (mp. 113–4° C.).

EXAMPLE 14

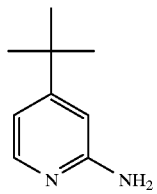

2-Amino-4-tert-butylpyridine

Using the procedure from Example 13 but substituting 4-tert-butylpyridine for 3,4-dimethylpyridine afforded 2-amino-4-tert-butylpyridine.

EXAMPLE 15

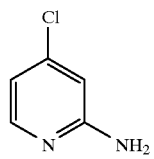

2-Amino-4-chloropyridine

The 4-chloro-2-picolinic acid hydrazide (mp. 166.5–68° C.) was treated with sodium nitrite according to the method of Graf (*Chem. Ber.* 64, 21 (1931)) to form the acylazide which was then heated in the presence of water to form the title compound (mp. 130–131° C.).

EXAMPLE 16

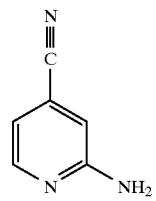

2-Amino-4-cyanopyridine

2-Amino-4-pyridinecarboxamide was dehydrated according to the method of Deady et al. (*Aust. J. Chem.*, 35, 2025 (1982)) to form the title compound (mp. 148–9° C.).

EXAMPLE 17

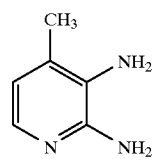

2,3-Diamino-4-methylpyridine

A solution of 2-amino-4-methyl-3-nitropyridine (Aldrich Chemical Co., 500 mg) in methanol (3 mL) was treated with palladium hydroxide on carbon (50 mg) and stirred under a hydrogen atmosphere (1 atm) at room temperature for 6 h. The mixture was filtered through a pad of celite filter aid and the solvent removed by rotoevaporation to give the title compound (340 mg).

Mass spectrum (FAB): m/e=124 (M+1).

EXAMPLE 18

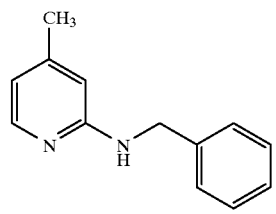

2-Benzylamino-4-methylpyridine

2-Amino-4-methylpyridine was reacted with potassium hydroxide in benzyl alcohol according to the method of Sprinzak (*Org. Syn. Coll. Vol. IV*. 91 (1963)) to form the title compound.

EXAMPLE 19

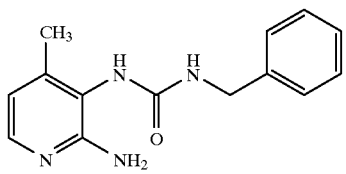

2-Amino-3-benzylurea-4-picoline

A solution of 2,3-diamino-4-picoline (example 17, 100 mg) in methylene chloride (2 mL) was treated with benzyl isocyanate (0.112 mL) and stirred at room temperature for 16 h. The mixture was filtered to collect the red ppt., washed with methanol, ethanol, hexane and dried under vacuum to give the title compound.

$^1$H NMR (400 MHz, CD$_3$OD): δ 7.70 (d, 1H), 7.32 (m, 4 H), 7.22 (m, 1H), 6.57 (d, 1H), 4.37 (s, 2H), 2.18 (s, 3H). Mass spectrum (FAB): m/e=257 (M+1).

EXAMPLE 20

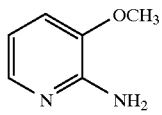

2-Amino-3-methoxypyridine

A solution of 2-amino-3-hydroxypyridine (Aldrich, 200 mg) in 20% methanol/benzene (4 mL) was treated with trimethylsilyldiazomethane (1.8 mL, 2.0 M), boron trifluoride diethyletherate (0.026 mL) and stirred at room temperature for 16 hr. The solvent was evaporated in vacuo and the crude oil was purified by medium pressure liquid chromatography on a 21×300 mm silica column eluted with 50% ethyl acetate/lmethylene chloride to give the title compound (50 mg).

$^1$H NMR (400 MHz, CDCl$_3$): δ 7.62 (d, 1H), 6.88 (d, 1H), 6.60 (dd, 1H), 4.60 (br, 2H), 3.82 (s, 3H). Mass spectrum (FAB): m/e=124 (M+1).

EXAMPLE 21

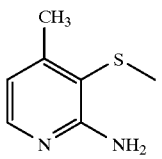

2-Amino-3-methylthio-4-picoline
Step A: 2-tert-Butylcarbonylamino-4-picoline

A solution of 2-amino-4-picoline (Aldrich, 5.0 g) in methylene chloride (80 mL) was treated with triethylamine (8.06 mL), trimethylacetyl chloride (6.26 mL) and stirred at 0° C. for 15 min., then at room temperature for 2 hr. The mixture was diluted with 200 mL water. The organic layer was washed with saturated sodium bicarbonate and saturated sodium chloride, dried over sodium sulfate, and concentrated in vacuo. The resulting oil was diluted in 50 mL hexane and cooled to 0° C. to crystallize the product. The crystals were collected by filtration and washed with cold hexane to afford the title compound (7.0 g).

$^1$H NMR (400 MHz, CDCl$_3$): δ 8.09 (d, 1H), 8.08 (s, 1H), 7.91 (br, 1H), 6.82 (d, 1H), 2,31 (s, 3H), 1.28 (s, 9H).

Step B: 2-tert-Butylcarbonlamino-3-methylthio-4-picoline

A solution of 2-tert-butylcarbonylamino-4-picoline (Step A, 250 mg) in anhydrous ethyl ether (5 mL) was cooled to −78° C. and treated with tert-butyllithium (1.7 mL, 1.7 M), and stirred at −78° C. for 3 hrs. To this was added dimethyl disulfide (0. 177 mL) and the reaction was allowed to warm to room temperature. The mixture was diluted with water and ethyl ether. The aqueous layer was extracted with ether. The combined organic layers were washed with saturated sodium chloride, dried over sodium sulfate, and concentrated in vacuo. The resulting oil was purified by medium pressure liquid chromatography on a 21×300 mm silica column eluted with 40% ethyl acetate/methylene chloride to afford the title compound (260 mg, lower Rf spot) and 2-tert-butylcarbonylamino-4-methylthiomethylpyridine (40 mg, higher Rf spot).

$^1$H NMR (400 MHz, CDCl$_3$): δ 9.29 (br, 1H), 8.29 (d, 1H), 6.90 (d, 1H), 2.51 (s, 3H), 2.21 (s, 3H), 1.34 (s, 9H).

Step C: 2-Amino-3-methlthio-4-picoline

A solution of 2-tert-butylcarbonylamino-3-methylthio-4-picoline (Step B, 260 mg) in 2 N HCl (5 mL) was heated at reflux for 10 hrs. after cooling to room temperature, the mixture was diluted with water and the aqueous layer was washed with ether. The combined organic layers were discarded and the aqueous layer was neutralized to pH=7 with saturated sodium carbonate. The aqueous layer then was extracted with ether, dried over sodium sulfate, and concentrated in vacuo to afford the title compound (150 mg).

$^1$H NMR (400 MHz, CDCl$_3$): δ 7.84 (d, 1H), 6.52 (d, 1H), 5.21 (br, 2H), 2.42 (s, 3H), 2.20 (s, 3H). Mass spectrum (FAB): m/e=155 (M+1).

EXAMPLE 22

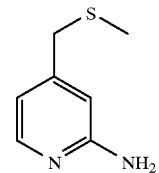

2-Amino-4-methylthiomethylpyridine

A solution of 2-tert-butylcarbonylamino-4-methylthiomethylpyridine (from Example 21, Step B) (40 mg) was treated in the same manner as described in Example 21, Step C to afford the title compound (25 mg).

$^1$H NMR (400 MHz, CDCl$_3$): δ 7.98 (d, 1H), 6.60 (d, 1H), 6.44 (s, 1H), 4.40 (br, 2H), 3.50 (s, 2H), 1.98 (s, 3H). Mass spectrum (FAB): m/e=155 (M+1).

EXAMPLE 23

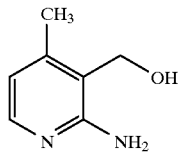

2-Amino-3-hydroxymethyl-4-picoline
Step A: 2-tert-Butylcarbonylamino-3-methoxymethyl-4-picoline A solution of 2-tert-butylcarbonylamino-4-picoline (from Example 21 Step A) (250 mg) was treated with methoxymethyl chloride (0.149 mL) under the same conditions as in Example 21, Step B to afford the title compound (125 mg).

$^1$H NMR (400 MHz, CDCl$_3$): δ 8.54 (br, 1H), 8.27 (d, 1H), 6.91 (d, 1H), 4.44 (s, 2H), 3.36 (s, 3H), 2,37 (s, 3H), 1.31 (s, 9H).

Step B: 2-Amino-3-hydroxymethyl-4-picoline

A solution of 2-tert-butylcarbonylamino-3-methoxymethyl-4-picoline (Step A, 125 mg) was treated in the same manner as described in Example 21, Step C. The resulting oil was purified by medium pressure liquid chromatography on a 21×130 mm silica gel column eluted with ethyl acetate to afford the title compound (10 mg) after crystallization from hexane.

$^1$H NMR (400 MHz, CDCl$_3$): δ 7.86 (d, 1H), 6.46 (d, 1H), 4.92 (br, 2H), 4.70 (s, 2H), 2.27 (s, 3H). Mass spectrum (FAB): m/e=138 (M+1).

EXAMPLE 24

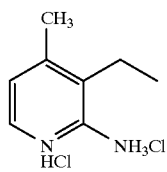

2-Amino-3-ethyl-4-picoline dihydrochloride

Step A: 2-tert-Butylcarbonylamino-3-ethyl-4-picoline

A solution of 2-tert-butylcarbonylamino-4-picoline (from Example 21, Step A) (250 mg) was treated with bromoethane (0.147 mL) under the same conditions as in Example 21, Step B to afford the title compound (40 mg).

$^1$H NMR (400 MHz, CDCl$_3$): δ 8.13 (d, 1H), 7.46 (br, 1H), 6.98 (d, 1H), 2.60 (q, 2H), 2,32 (s, 3H), 1.32 (s, 9H), 1.08 (t, 3H).

Step B: 2-Amino-3-ethyl-4-picoline dihydrochloride

A solution of 2-tert-butylcarbonylamino-3-ethyl-4-picoline (Step A, 40 mg) was treated in the same manner as described in Example 21, Step C. The resulting oil was dissolved in ether and HCl gas bubbled into the solution to afford the title compound after evaporating the solvent.

$^1$H NMR (400 MHz, CD$_3$OD): δ 7.61 (d, 1H), 6.81 (d, 1H), 2.67 (q, 2H), 2.42 (s, 3H), 1.13 (t, 3H). Mass spectrum (FAB): m/e=137 (M+1).

EXAMPLE 25

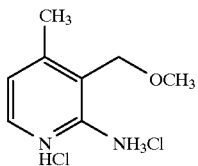

2-Amino-3-methoxymethyl-4-picoline dihydrochloride

A solution of 2-tert-butylcarbonylamino-3-methoxymethyl-4-picoline (Example 21, Step A) (65 mg) in 2 mL dioxane was treated with 1 mL hydrazine and stirred at reflux for 6 hrs. After cooling to room temperature, the reaction mixture was diluted with water. The aqueous layer was extracted with methylene chloride. The combined organic layers were dried over sodium sulfate and concentrated in vacuo. The resulting oil was purified by medium pressure liquid chromatography on a 21×130 mm silica gel column eluted with ethyl acetate. The resulting oil was dissolved in ether and HCl gas bubbled into the solution to afford the title compound after evaporating the solvent.

$^1$H NMR (400 MHz, CDCl$_3$, free base): δ 7.86 (d, 1H), 6.46 (d, 1H), 4.88 (br, 2H), 4.46 (s, 2H), 3.33 (s, 3H), 2.26 (s, 3H). Mass spectrum (FAB): m/e=153 (M+1).

EXAMPLE 26

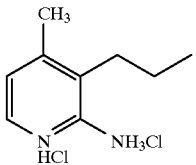

2-Amino-3-n-propyl-4-picoline dihydrochloride

Step A: 2-tert-Butylcarbonylamino-3-propyl-4-picoline

A solution of 2-tert-butylcarbonylamino-4-picoline (Example 21, Step A) (250 mg) was treated with iodopropane (0.153 mL) under the same conditions as in Example 21, Step B to afford the title compound (28 mg).

$^1$H NMR (400 MHz, CDCl$_3$): δ 8.13 (d, 1H), 7.52 (br, 1H), 6.97 (d, 1H), 2.53 (dd, 2H), 2,32 (s, 3H), 1.46 (m, 2H), 1.32 (s, 9H), 0.92 (t, 3H).

Step B: 2-Amino-3-propyl-4-picoline dihydrochloride

A solution of 2-tert-butylcarbonylamino-3-propyl-4-picoline (Step A, 28 mg) was treated in the same manner as described in Example 21, Step C. The resulting oil was dissolved in ether and HCl gas bubbled into the solution to afford the title compound after evaporating the solvent.

$^1$H NMR (400 MHz, CDCl$_3$, free base): δ 7.78 (d, 1H), 6.49 (d, 1H), 4.33 (br, 2H), 2.43 (dd, 2H), 2.22 (s, 3H), 1.53 (m, 2H), 0.99 (t, 3H). Mass spectrum (FAB): m/e=151 (M+1).

EXAMPLE 27

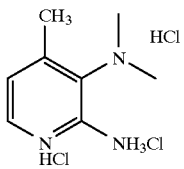

2-Amino-3-dimethylamino-4-picoline trihydrochloride

Step A: 2-tert-Butylcarbonylamino-3-azido-4-picoline

A solution of 2-tert-butylcarbonylamino-4-picoline (Example 21, Step A) (1.0 g) was treated with trisylazide (1.94 g) under the same conditions as in Example 21, Step B to afford the title compound (1.0 g).

$^1$H NMR (400 MHz, CDCl$_3$): δ 8.15 (d, 1H), 7.68 (br, 1H), 6.97 (d, 1H), 2,32 (s, 3H), 1.35 (s, 9H).

Step B: 2-tert-Butylcarbonylamino-3-dimethylamino-4-picoline

A solution of 2-tert-butylcarbonylamino-3-azido-4-picoline (Step A, 100 mg) was treated with palladium(II) hydroxide on carbon (35 mg), formaldehyde (37% in water, 0.032 mL), and hydrogen gas at 1 atmospheric pressure in methanol (3 mL) at room temperature for 16 h. The catalyst was removed by filtration and the resulting oil was purified by medium pressure liquid chromatography on a 21×300 mm silica gel column eluted with a gradient from 0 to 3% methanol in ethyl acetate to afford the title compound (40 mg).

$^1$H NMR (400 MHz, CDCl$_3$): δ 9.42 (br, 1H), 8.10 (d, 1 H), 6.70 (d, 1H), 2.78 (s, 6H), 2,30 (s, 3H), 1.29 (s, 9H).

Step C: 2-Amino-3-dimethylamin-4-picoline trihydrochloride

A solution of 2-tert-butylcarbonylamino-3-dimethylamino-4-picoline (Step B, 40 mg) was treated in the same manner as described in Example 21, Step C. The resulting oil was purified by medium pressure liquid chromatography on a 21×130 mm silica gel column eluted with from 1% methanol in ethyl acetate. The resulting oil was dissolved in ether and HCl gas bubbled into the solution to afford the title compound(20 mg) after evaporating the solvent.

$^1$H NMR (400 MHz, CDCl$_3$, free base): δ 7.67 (d, 1H), 6.35 (d, 1H), 4.91 (br, 2H), 2.75 (s, 6H), 2.22 (s, 3H). Mass spectrum (FAB): m/e=152 (M+1).

EXAMPLE 28

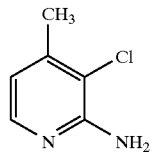

2-Amino-3-chloro-4-picoline

To a solution of 72% sulfuric acid (135 mL) cooled to 0° was added portionwise 2-amino-4-picoline (27g, 0.25 mol) keeping the temperature below 25° C. After the addition was completed, the bath was removed and condensed chlorine (11.4 mL) was allowed to evaporate and bubble through the reaction mixture over 1.5 h. The reaction mixture was then stirred for 1.5 h under chlorine reflux using a dry ice condenser, allowed to warm to room temperature and stirred for 18 h. The reaction mixture was poured into 500 g of ice, the pH adjusted to 10 by addition of 50% NaOH and 1 L of water was added. The mixture of 3-chloro and 5-chloro isomers was extracted with chloroform, dried ($Na_2SO_4$), and evaporated. The title compound was separated from 2-amino-5-chloro-4-picoline (see Example 29) by silica gel chromatography using 2% methanol/methylene chloride as eluant.

$^1$H NMR (400 MHz, $CDCl_3$): δ 2.30 (s,3H); 6.51(d,1H); 7.82 (d,1H); Mass spectrum (FAB): m/e=143 (M+1).

EXAMPLE 29

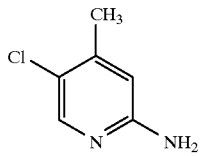

2-Amino-5-chloro-4-picoline

The title compound was isolated from the reaction in Example 28.

$^1$H NMR (400 MHz, $CDCl_3$): δ 2.25 (s,3H); 6.35 (s,1H); 7.93 (s,1H); Mass spectrum (FAB): m/e=143 (M+1).

EXAMPLE 30

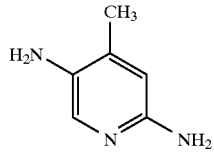

2.5-Diamino-4-picoline

To a solution of tin(II) chloride (4.95 g, 26.12 mmol) in concentrated hydrochloric acid (13.0 mL) was added 2-amino-5-nitro-4-picoline (1.0 g, 6.53 mmol) and heated at 90° C. for 24 h. The reaction was cooled to room temperature, made basic with 5N NaOH, extracted with ethyl acetate, dried ($Na_2SO_4$), and evaporated to give a solid. The crude material was subjected to silica gel chromatography using 10% methanol/methylene chloride as eluant to give the title compound.

$^1$H NMR (400 MHz, $CD_3OD$): δ 2.14 (s,3H); 6.42 (s,1H); 7.45 (s,1H); Mass spectrum (FAB): m/e=124 (M+1).

EXAMPLE 31

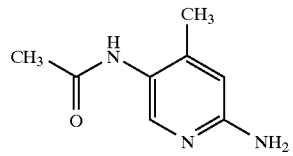

5-Acetylamino-2-amino-4-picoline

To a solution of 2,5-diamino-4-picoline, prepared as shown in Example 30, (50 mg, 0.41 mmol) in methylene chloride (1.0 mL) were added triethylamine (70 uL, 0.49 mmol) and acetic anhydride (43 uL, 0.45 mmol). After stirring 0.5 h at room temperature, the reaction mixture was evaporated to dryness and purified by silica gel chromatography using 40:10:1 chloroform-methanol-water as eluant to give the title compound.

$^1$H NMR (400 MHz, $CD_3OD$): δ 2.12 (s,3H); 2.13 (s,3H) 6.47 (s,1H); 7.70 (s,1H); Mass spectrum (FAB): m/e=166 (M+1).

EXAMPLE 32

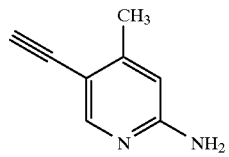

2-Amino-5-ethynyl-4-methyl-pyridine

Step A: 5-Nitro-4-methyl-2-(trimethylacetyl)aminopyridine

To a mixture of 5-nitro-4-methyl-2-aminopyridine (1.0 g, 6.53 mmol) in 15 mL of methylene chloride was added triethylamine (1.14 mL, 8.16 mmol) and cooled to 0° C. To this was added dropwise a solution of trimethylacetyl chloride (0.89 mL, 7.18 mmol) and the mixture allowed to warm to room temperature and stirred 72 h. The solution was diluted with 100 mL of methylene chloride, washed with saturated sodium bicarbonate, water, brine, dried ($Na_2SO_4$), and evaporated to an amber oil. This was subjected to silica gel chromatography using 10% ethyl acetate/hexane as eluant to yield the title compound.

$^1$H NMR (400 MHz, $CDCl_3$): δ 1.34 (s,9H); 2.65 (s,3H); 8.18 (b,1H); 8.29 (s,1H); 8.94 (s,1H).

Step B: 5-Amino-4-methyl-2-(trimethylacetyl) aminopyridine

A solution of 5-nitro-4-methyl-2-trimethylacetylaminopyridine (4.5 g, 18.97 mmol) in 50 mL of acetic acid containing 10% palladium/carbon was hydrogenated at atmospheric pressure for 48 h. The catalyst was removed by filtration and the filtrate was concentrated. The residue was coevaporated with toluene to give the title compound.

$^1$H NMR (400MHz, $CDCl_3$): δ 1.29 (s,9H); 2.19 (s,3H); 7.60 (s,1H); 8.04 (s,1H); 8.50 (b,1H).

Step C: 5-Iodo-4-methyl-2-(trimethylacetyl)aminopyridine

A mixture of 5-amino-4-methyl-2-(trimethylacetyl) aminopyridine (1.0 g, 4.82 mmol) in 34 mL of diiodomethane containing isoamyl nitrite (4.0 mL, 29.77 mmol) was heated at 85° C. for 0.5 h, cooled to room temperature and evaporated at 60° C. under high vacuum to give a red semi-solid. The crude material was purified by silica gel column chromatography using 10% ether/hexane as eluant to give the title compound.

$^1$H NMR (400 MHz, $CDCl_3$): δ 1.30 (s,9H); 2.40 (s,3H); 7.90 (b,1H); 8.22 (s,1H); 8.45 (s,1H).

Step D: 5-Ethynyl-4-methyl-2-(trimethylacetyl) aminopyridine

To a mixture of 5-iodo-4-methyl-2-trimethylacetylaminopyridine (176 mg, 0.55 mmol) in tetrahydrofuran (0.60 mL), triethyamine (3.32 mL), bis(triphenylphosphine)palladium(II) chloride (4 mg), copper (I) iodide (1.1 mg) and (trimethylsilyl)acetylene (117 uL, 0.83 mmol) were added. The mixture was stirred at room temperature for 3 h. The mixture was diluted with chloroform (50 mL), dried ($Na_2SO_4$), and evaporated to give a tan solid. The crude solid was dissolved in methanol (5 mL), treated with 1N potassium hydroxide (0.61 mL) and stirred at room temperature 18 h. The mixture was evaporated to dryness, dissolved in chloroform (50 mL), dried over $Na_2SO_4$, and evaporated to a solid. The product was purified by silica gel column chromatography using 10% ethyl acetate/hexane to yield the title compound.

$^1$H NMR (400MHz, $CD_3OD$): δ 1.30 (s,9H); 2.45 (s,3H); 3.85 (s,1H); 8.02 (s,1H); 8.30 (s,1H); Mass spectrum (FAB): m/e=217 (M+1).

Step E: 2-Amino-5-ethynyl-4-methyl-pyridine

A suspension of 5-ethynyl-4-methyl-2-(trimethylacetylamino)-pyridine (50 mg, 0.23 mmol) in 2N sodium hydroxide (1.0 mL) was heated at 90° C. for 18 h. The reaction mixture was cooled to room temperature, extracted with chloroform, dried ($Na_2SO_4$), and evaporated to give a tan solid. The title compound was purified by silica gel chromatography using 1% methanol/methylene chloride as eluant.

400 MHz $^1$H NMR ($CD_3OD$): δ 2.28 (s,3H); 3.59 (s,1H); 6.40 (s,1H); 7.92 (s,1H); Mass spectrum (FAB): m/e=133 (M+1).

EXAMPLE 33

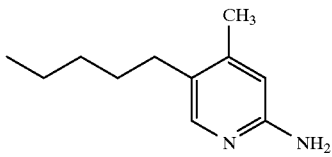

2-Amino-4-methyl-5-pentyl-pyridine

Step A: 4-Methyl-2-(trimethylacetyl)amino-5-(1-pentynyl)-pyridine

The above compound was prepared in a similar fashion as Example 32, Step D, but substituting 1-pentyne in place of (trimethylsilyl)acetylene to yield the title compound.

$^1$H NMR (400 MHz, $CD_3OD$): δ 1.08 (t,3H); 1.30 (s,9H); 1.65 (q,2H); 2.40 (s,3H); 2.45 (t,2H); 7.98 (s,1H); 8.20 (s,1H).

Step B: 4-Methyl-2-(trimethylacetyl)amino-5-(1-pentyl)-pyridine

A solution of 4-methyl-2-(trimethylacetyl)amino-5-(1-pentynyl)-pyridine (225 mg, 0.87 mmol) in ethyl acetate (4.5 mL) containing platinum oxide (45 mg) was hydrogenated at atmospheric pressure for 1.5 h. The catalyst was removed by filtration through a Millex-HV 0.45 um Filter Unit. Evaporation of the filtrate gave the title compound.

$^1$H NMR (400 MHz, $CD_3OD$): δ 0.95 (t,3H); 1.33(s,9H); 1.40 (m,4H); 1.60 (m,2H); 2,35 (s,3H); 2.63 (m,2H); 7.84 (s,1H); 8.00 (s,1H); Mass spectrum (FAB): m/e=263 (M+1).

Step C: 5-(1-Pentyl)-4-methyl-2-aminopyridine

A suspension of 4-methyl-2-(trimethylacetyl)amino-5-(1-pentyl)-pyridine (233 mg, 0.89 mmol) in 2N hydrochloric acid (3 mL) was heated at 100° C. for 18 h. The solution was cooled to room temperature, made basic with 20% aqueous sodium carbonate and extracted with chloroform. The organic layer was dried ($Na_2SO_4$), and evaporated. The product was purified by silica gel column chromatography using 2% methanol/methylene chloride to give the title compound.

$^1$H NMR (400MHz, $CD_3OD$): δ 0.90 (t,3H); 1.35 (s,4H); 1.50 (m,2H); 2.20 (s,3H); 2.45 (m,2H); 6.40 (s,1H); 7.58 (s,1H); Mass spectrum (FAB): m/e=179 (M+1).

EXAMPLE 34

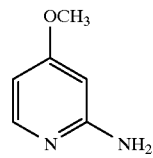

4-Methoxy-2-aminopyridine

4-Methoxy-2-aminopyridine was prepared from 4-chloro-2-aminopyridine by the method of G. B. Barlin et al (*J. Chem. Soc.* (B) 1425, 1971).

$^1$H NMR (400 MHz, $CDCl_3$) δ 7.18 (d, 1H, J=7 Hz); 5.95 (dd, 1H, J=7 Hz, J=2 Hz); 5.86 (d, 1H, J=2 Hz); 4.40(bs, 2H); 3.77 (s, 3H). Mass spectrum (FAB): m/e=129 (M+1).

EXAMPLE 35

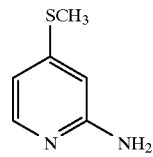

4-Methylthio-2-aminopyridine

Step A: 4-Methylthio-2-picolinic acid, methyl ester

4-Chloro-2-picolinic acid, methyl ester (1.0 g, 5.8 mmol) and 1.4 g (20 mmol) of sodium thiomethoxide in 10 mL of methanol was placed in a sealed thick wall glass tube and heated at 100° C. for 1 h. After cooling, the solution was acidified with 20 mmol of 12 N HCl in 5 mL of water, then nitrogen gas was bubbled into the reaction until most of the thiomethanol was purged. A precipitate was isolated by filtration to yield 240 mg of title compound.

$^1$H NMR (200 MHz, $CDCl_3$) δ 8.47(d,1H, J=5 Hz); 7.91(d, 1H, J=2 Hz); 7.24 (dd, 1H, J=5 Hz, J=2 Hz); 3.98 (s, 3H); 2.51(s, 3H).

Step B: 2-Azidocarbonyl-4-methylthiopyridine

4-Methylthio-2-picolinic acid, methyl ester (170 mg, 0.93 mmol) and 40 uL of anyhydrous hydrazine in 2 mL of methanol was refluxed for 1 h under a nitrogen atmosphere. The solvent was removed under reduced pressure to afford the hydrazide (160 mg).

$^1$H NMR 400 MHz($CD_3OD$) δ 8.36 (d,1H, J=5 Hz); 7.86 (d, 1H, J=2 Hz); 7.35 (dd, 1H, J=5 Hz, J=2 Hz); 2.56(s, 3H).

This material was suspended in 5 mL of 2N HCl at 0° C. Sodium nitrite (400 mg) was added portionwise to the solution with vigorous stirring. After stirring for 1 h, solid sodium bicarbonate was added portionwise until the pH=6. A precipitate was isolated by filtration and it was washed successively with cold water (3×5 mL) and dried under vacuum to give 90 mg of 4-methylthio-2-acylazidopyridine which was used without further purification.

Step C: 4-Methylthio-2-aminopyridine

The crude material from Step B above was suspended in 4 mL of a 1:1 mixture of water and acetic acid and heated for 1 h at 100° C. The solvent was removed under reduced pressure and the residue purified by silica gel column chromatography (95/5—CH$_2$Cl$_2$/methanol) to yield 25 mg of the title compound.

$^1$H NMR (400 MHz, CDCl$_3$) δ 7.85 (d, 1H, J=5 Hz); 6.48 (dd, 1H, J=5 Hz, J=2 Hz); 6.26 (d, 1H, J=2 Hz); 4.38 (bs, 2H); 2.41 (s, 3H). Mass spectrum (FAB): m/e=141 (M+1).

EXAMPLE 36

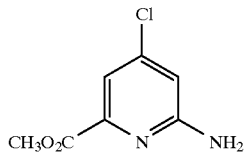

4-Chloro-6-methoxycarbonyl-2-aminopyridine
Step A: N-Ethyl-4-2pyridone-2,6-dicarboxylic acid
This intermediate was synthesized according to the method described by D. G. Markees (*J. Org. Chem.* 23, 1030 (1958)).
Step B: 4-Chloropyridine-2,6-dicarboxylic acid, dimethyl ester
N-Ethyl-4-pyridone-2,6-dicarboxylic acid, prepared in Step A of Example 36, was treated with thionyl chloride and heated at 80° C. as described in the literature. The excess thionyl chloride was removed under reduced pressure and the remaining residue was cooled to 0° C. The product was slowly poured into cold methanol with vigorous stirring. The solvent was then removed in vacuo and the crude product was purified by silica gel column chromatography. Two products were isolated: the higher R$_f$ product was 4,6-dichloropicolinic acid methyl ester while the lower R$_f$ product was the title compound.

$^1$H NMR (400 MHz, CDCl$_3$) δ 8.28 (s, 2H); 4.01 (s, 6H).
Step C: 4-Chloro-6-carbomethoxy-2-aminopyridine
4-Chloropyridine-2,6-dicarboxylic acid, dimethyl ester (230 mg, 1 mmol) was converted to the monoacyl hydrazide by adding one-half equivalent of anyhydrous hydrazine. The monohydrazide was converted to the monoacyl azide by the methodology described in step B of Example 35. The title compound was obtained by applying the methodology described in step C of Example 35.

$^1$H NMR (400 MHz, CDCl$_3$) δ 7.43 (d, 1H, J=1.5 Hz); 6.65 (d, 1H, J=1.5 Hz ); 4.91 (bs, 1H); 3.93 (s, 3H). Mass spectrum (FAB): m/e=187 (M+1).

EXAMPLE 37

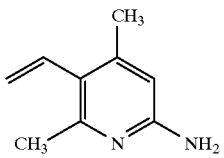

4,6-Dimethyl-5-ethenyl-2-aminopyridine
Step A: 5-Formyl-4,6-dimethyl-2-aminopyridine
To a 250 mL round bottomed flask was added a magnetic stirrer bar, 4,6-dimethyl-5-cyano-2-aminopyridine (2.94 g, 20 mmol) (SALOR Chemical) and 100 mL of dry benzene. The flask was stoppered with a rubber septum, flushed with nitrogen and cooled to 10° C. A solution of DIBAL in toluene (1M, 40 mL; Aldrich) was slowly added to the reaction mixture via syringe over a 30 min period. The temperature was maintained at or below 25° C. during the addition. After the addition was complete, the solution was heated at 50° C. for 45 min, cooled to 0° C. A solution of 2N HCl was added portionwise with vigorous stirring. After the gas evolution ceased, ice water (50 mL) was added. The aluminum salt precipitant was removed by filtration. The mixed aqueous/organic solution was made slightly basic (pH=9) with sodium carbonate. The organic layer is decanted and the aqueous layer was extracted with 8×50 mL of ethyl acetate. The organic extracts were combined with the benzene layer and the solvent removed under reduced pressure. The title compound was recovered 2.05 g (76%) and used as is in the next reaction.

$^1$H NMR (400 MHz, CDCl$_3$) δ 10.36 (s, 1H); 6.14 (s, 1H); 4.82 (bs, 1H); 2.65 (s, 3H); 2.49 (s, 1H).
Step B: 4,6-Dimethyl-5-ethenyl-2-aminopyridine
In a 10 mL round bottomed flask was added a magnetic stirrer bar, 500 mg (1.2 mmol) of triphenylphosphonium methyl bromide and 137 mg (1.22 mmol) of potassium t-butoxide. The flask is stoppered with a rubber septum, flushed with nitrogen and 5 mL of dry THF was added to the mixture. After stirring at room temperature for 1 h, the solution was cooled to −60° C. and a solution of 170 mg (1.0 mmol) of 5-formyl4,6-dimethyl-2-aminopyridine in 2 mL of THF was added. After stirring for 30 minutes, the solution was warmed to 25° C. and stirred for 1 h. The solvent was removed in vacuo and and the title compound purified by silica gel column chromatography eluted with (methylene chloride/methanol (95:5).

$^1$H NMR (400 MHz, CDCl$_3$) δ 6.58 (dd, 1H, J=18 Hz, J=11 Hz); 5.44 (dd, 1H, J=11 Hz, J=2 Hz); 5.20 (dd, 1H, J=18 Hz, J=2 Hz); 4.29 (bs, 1H); 2,37 (s, 3H); 2.18 (s, 1H). Mass spectrum (FAB): m/e=171 (M+1).

EXAMPLE 38

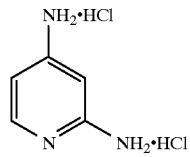

2,4-Diaminopyridine dihydrochloride
Step A: 4-Methyl-2-acetylaminopyridine
This reagent was prepared from 4-methyl-2-aminopyridine by the method cited (*Bull Chem. Soc*, 96, 542 (1957).
Step B: 4-Carboxy-2-acetylaminopyridine
In a 500 mL beaker fitted with a large Teflon coated magnetic stirrer bar was added 200 mL of water and 20 g (133 mmol) of 4-methyl-2-acetylaminopyridine. The solution temperature was raised to 85° C. and 46 g (291 mmol, 2.2 eq) of potassium permanganate was added portionwise over 1 h at such a rate that the solution temperature remained between 85–90° C. After permanganate addition was completed, the mixture was stirred for 30 min at 90° C. The mixture was then filtered through a bed of celite while still hot and then the filtrate volume was reduced by two thirds in vacuo. After cooling to room temperature, the mixture was again filtered through celite. The pH of the filtrate was adjusted to 4.5 with concentrated HCl. The water was removed in vacuo and the product recrystallized from water/ethanol to give 3.4 g of the title compound.

$^1$H NMR (200 MHz, CD$_3$OD) δ 8.60 (d, 1H, J=2 Hz); 8.39 (d, 1H, J=5 Hz); 7.56 (dd, 1H, J=5 Hz, J=2Hz); 2.16 (s, 3H).
Step C: 4-Methoxycarbonyl-2-acetylaminopyridine 4-Carboxy-2-acetylaminopyridine (3.4 g, 19 mmol) was dissolved in methanol/benzene (100 mL, 1:1). TMS-diazomethane was added (1M, Aldrich) with cooling until the yellow color just persisted, then the solvent was removed under reduced pressure. The product was purified by silica gel column chromatography (50/50 hexane/ethyl acetate) and 3.0 g of product was recovered.

$^1$H NMR (200 MHz, CDCl$_3$) δ 8.68 (d, 1H, J=2 Hz); 8.35 (d, 1H, J=5 Hz); 7.57 (dd, 1H, J=5 Hz, J=2Hz); 3.92 (s, 3H); 2.16 (s, 3H).

Step D: 2-Acetylaminopyridine-4-hydrazide

4-Methoxycarbonyl-2-acetylaminopyridine (210 mg, 1.1 mmol) was converted to the corresponding hydrazide via the procedure described in the first part of step B of Example 35.

$^1$H NMR (200 MHz, CD$_3$OD) δ 8.40 (s 1H); 8.35 (s 1H); 7.37 (dd, 1H, J=5 Hz, J=2Hz); 2.16 (s, 3H).

Step E: 4-Azidocarbonyl-2-acetylaminopyridine

The title compound was obtained from 2-acetylaminopyridine-4-hydrazide by the procedure described in the second part of step B of Example 35.

$^1$H NMR (200 MHz, CD$_3$OD) δ 8.61 (d 1H); 8.42 (t, 1H); 7.7 (t, 1H); 2.16 (s, 3H).

Step F: 4-Amino-2-acetylaminopyridine

The title compound was obtained from 4-azidocarbonyl-2-acetylaminopyridine by the procedure described in step C of Example 35.

$^1$H NMR (200 MHz, CD$_3$OD) δ 7.69 (d, 1H, J=6 Hz); 6.80 (d, 1H, J=2 Hz); 6.45 (dd, 1H, J=6 Hz, J=2Hz); 2.14 (s, 3H).

Step G: 2,4-Diaminopyridine, dihydrochloride

4-Amino-2-acetylaminopyridine (150 mg, 1.0 mmol) was dissolved in 5 mL of concentrated aqueous ammonium hydroxide and heated in a glass pressure tube for 18 h at 100° C. The solvent was removed under reduced pressure and the residue dissolved in 3 mL of 2N HCl. The solvent was removed under reduced pressure and the product isolated by recrystallization from ethanol to give 102 mg of the bis hydrochloride salt.

$^1$H NMR (200 MHz, CD$_3$OD) δ 7.35 (bs, 1H); 6.12 (d, 1H, J=5 Hz); 5.79 (bs, 1H). Mass spectrum (FAB): m/e=110 (M+1).

EXAMPLE 39

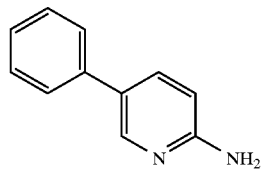

2-Amino-5-phenylpyridine

To a mixture of tetrakis(triphenylphosphine) palladium(0) (347 mg, 0.30 mmol) and 2-amnno-5-bromopyridine (1.73 g, 10 mmol) in benzene (20 mL) were added 2M sodium carbonate (10 mL) and a solution of phenylboronic acid (1.38 g, 11 mmol) in the minimum amount of ethanol. The reaction mixture was stirred for 3 h at reflux temperature under a nitrogen atmosphere. After cooling, the mixture was extracted with ethyl acetate, washed with water, saturated brine solution, dried (MgSO4), and evaporated. The title compound was obtained as a white crystalline solid after chromatography on silica gel (25% acetone/hexane); yield 320 mg (19%).

$^1$H NMR (400 MHz, CD$_3$OD): δ 6.67 (d, 1H), 7.28 (d, 1H), 7.39 (t, 2H), 7.51 (d, 2H), 7.73 (dd, 1H), 8.12 (d, 1H). Mass spectrum (FAB): m/e=171 (M+1).

EXAMPLE 40

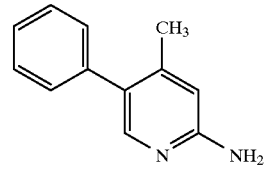

2-Amino-4-methyl-5-phenylpyridine

The title compound was obtained by an analogous procedure to Example 39, but substituting 2-amino-5-bromo-4-methylpyridine in place of 2-amino-5-bromopyridine.

$^1$H NMR (400 MHz, CD$_3$OD): δ 2.17 (s, 3H), 6.51 (s, 1H), 7.27–7.42 (m, 5H), 7.68 (s, 1H). Mass spectrum (FAB): m/e=185 (M+1).

EXAMPLE 41

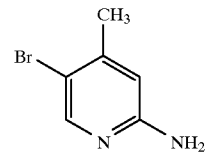

2-Amino-5-bromo-4-methylpyridine

To a solution of 2-amino-4-picoline (20 g, 0.185 mol) in glacial acetic acid (185 mL) was added bromine (12.5 mL, 0.243 mol) dropwise with stirring while maintaining the internal temperature between 15–20° C. by cooling in an ice bath. After the addition was completed, the reaction was stirred for 1 h. The resulting solid was filtered, washed with water, and treated with dilute aqueous sodium hydroxide. The remaining white solid was filtered, washed with water and then hexane. Recrystallization from diethyl ether-cyclohexane afforded the title compound; yield 8.1 g (23%).

$^1$H NMR (400 MHz, CD$_3$OD): δ 2.25 (s, 3H), 6.51 (s, 1H), 7.89 (s, 1H). Mass spectrum (FAB): m/e=187 (M).

EXAMPLE 42

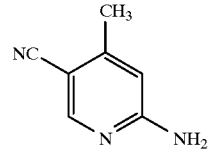

2-Amino-5-cyano-4-methylpyridine

A mixture of 2-amino-5-bromo-4-methylpyridine (4.0 g, 21.4 mmol) and copper(I) cyanide (2.2 g, 24.6 mmol) in N,N-dimethylformamide (5 mL) was stirred for 4 h at reflux temperature. The hot mixture was poured into a warm solution of sodium cyanide (4.3 g) in water (13 mL). After the mixture was vigorously shaken, the mixture was extracted with ethyl acetate. The organic extract was washed with 10% aqueous sodium cyanide, saturated brine solution and evaporated. The title compound was obtained as a solid after chromatography on silica gel (15% acetone/hexane); yield 1.81 g (64%).

$^1$H NMR (400 MHz, CD$_3$OD): δ 2.32 (s, 3H), 6.44 (s, 1H), 8.17 (s, 1H). Mass spectrum (FAB): m/e=134 (M+1).

EXAMPLE 43

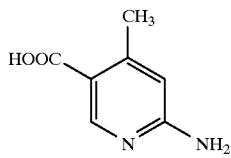

2-Amino-5-carboxy-4-methylpyridine

A solution of 2-amino-5-cyano-4-methylpyridine (600 mg, 4.50 mmol) in ethanol (7.5 mL) was treated with 10N sodium hydroxide (7.5 mL) for 24 h at reflux temperature. The mixture was cooled and diluted with water (30 mL). The pH was adjusted to 7 with conc. hydrochloric acid and 1N hydrochloric acid. The resulting solid was filtered, dried by suction, washed with ether, and dried in vacuo; yield 134 mg (20%).

$^1$H NMR (400 MHz, DMSO-d$_6$): δ 2.38 (s, 3H), 6.22 (s, 1H), 8.43 (s, 1H). Mass spectrum (FAB): m/e=153 (M+1).

EXAMPLE 44

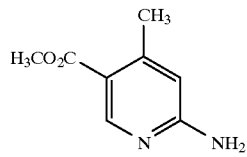

2-Amino-5-methoxycarbonyl-4-methylpyridine

A mixture of 2-amino-5-carboxy-4-methylpyridine (100 mg, 0.657 mmol) in 7:3 benzene-methanol (4 mL) was treated with (trimethylsilyl)diazomethane (2M solution in hexanes, 0.33 mL, 0.66 mmol). The mixture was evaporated and the residue chromatographed on silica gel eluting with 25% acetone/hexane to afford pure title compound; yield 88 mg (81%).

$^1$H NMR (400 MHz, CD$_3$OD): δ 2.47 (s, 3H), 3.80 (s, 3H), 6.39 (s, 1H), 8.48 (s, 1H). Mass spectrum (FAB): m/e=167 (M+1).

EXAMPLE 45

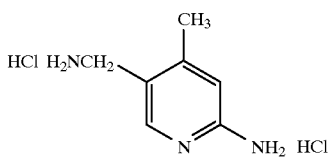

2-Amino-5-aminomethyl-4-methylpyridine dihydrochloride

A solution of 2-amino-5-cyano-4-methylpyridine (200 mg, 1.50 mmol) in a mixture of ethanol (17 mL) and methanol (7 mL) was hydrogenated for 48 h at atmospheric pressure in the presence of 1N hydrochloric acid (3 mL) and 10% palladium-on-charcoal (50 mg). The catalyst was removed by filtration through Celite, the filter washed with methanol, and the combined filtrate and washings evaporated. Crystallization from chloroform-methanol afforded pure title compound; yield 98 mg (31%).

$^1$H NMR (400 MHz, CD$_3$OD): δ 2.45 (s, 3H), 4.11 (d, 2H), 6.82 (s, 1H), 7.91 (s, 1H). Mass spectrum (FAB): m/e=138 (M+1).

EXAMPLE 46

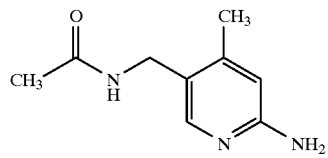

2-Amino-5-acetamidomethyl-4-methylpyridine

To a solution of 2-amino-5-aminomethyl-4-methylpyridine dihydrochloride (70 mg, 0.333 mmol) in methanol (2 mL) were added triethylamine (93 uL, 0.667 mmol) and acetic anhydride (47 uL, 0.498 mmol). The reaction mixture was stirred for 2 h at room temperature and then evaporated. The residue was chromatographed on silica gel (10% methanol/methylene chloride) to afford pure title compound.

$^1$H NMR (400 MHz, CD$_3$OD): δ 1.96 (s, 3H), 2,31 (s, 3H), 4.22 (s, 2H), 6.62 (s, 1H), 7.68 (s, 1H). Mass spectrum (EI): m/e=179 (M$^+$).

EXAMPLE 47

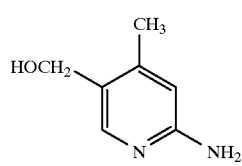

2-Amino-5-hydroxymethyl-4-methylpyridine

To a mixture of lithium aluminum hydride (LAH) (90 mg, 2.37 mmol) in dry tetrahydrofuran (THF) (2 mL) was added a solution of 2-amino-5-methoxycarbonyl-4-methylpyridine (100 mg, 0.602 mmol) in THF (1 mL). The reaction mixture was stirred for 1 h at reflux temperature. Excess LAH was decomposed by successive addition of water (90 uL), 15% sodium hydroxide (90 uL), and water (270 uL). Solids were removed by filtration through a pad of Celite. The title compound was obtained as a white crystalline solid after chromatography on silica gel (5–15% methanol/methylene chloride).

$^1$H NMR (400 MHz, CD$_3$OD): δ 2.29 (s, 3H), 4.48 (s, 2H), 6.42 (s, 1H), 7.72 (s, 1H). Mass spectrum (FAB): m/e=139 (M+1).

EXAMPLE 48

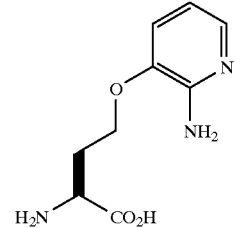

2-(2-Amino-3-pyridinoxy)-ethyl-(S)-glycine dihydrochloride

Step A: N-(tert-Butyloxycarbonyl)-2-(2-amino-3-pyridinoxy)-ethyl-(S)-glycine tert-butyl ester To a solution of N-(tert-butyloxycarbonyl)-(S)-homoserine tert-butyl ester (100 mg, 0.363 mmol) in tetrahydrofuran (4 mL) were added triphenylphosphine (190 mg, 0.724 mmol), 2-amino-3-hydroxypyridine (80 mg, 0.726 mmol), and diisopropyl azodicarboxylate (0.138 mL, 0.700 mmol). The reaction mixture was stirred for 24 h at room temperature and then evaporated. The residue was chromatographed on silica gel to afford the title compound; yield 14.5 mg.

$^1$H NMR (400 MHz, CDCl$_3$): δ 1.40 (s, 9H), 1.47 (s, 9H), 2.12 (m, 1H), 2.37 (m, 1H), 4.03–4.19 (m, 2H), 4.40 (m, 1H), 6.61 (dd, 1H), 7.00 (d, 1H), 7.48 (d, 1H). Mass spectrum (FAB): m/e=368 (M+1).

Step B: 2-(2-Amino-3-pyridinoxy)-ethyl-(S)-glycine dihydrochloride

The compound from Step A (14.5 mg) was treated with 4N HCl/dioxane (0.5 mL) for 6 h at room temperature. The mixture was evaporated, coevaporated several times each with diethyl ether and methanol. After drying in vacuo, the title compound was obtained in quantitative yield.

$^1$H NMR (400 MHz, CD$_3$OD): δ 2.41–2.61 (m, 2H), 4.32–4.43 (m, 3H), 6.89 (t, 1H), 7.48 (app d, 2H).

EXAMPLE 49

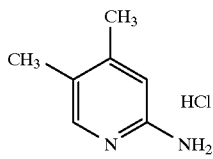

2-Amino-4,5-dimethylpyridine hydrochloride

Step A: 2-Acetamido-4,5-dimethylpyridine.

Acetic anhydride (2.0 mL, 21 mmol) and 500 mg (4.09 mmol) of a 4:1 mixture of 2-amino-3,4-dimethylpyridine and 2-amino-4,5-dimethylpyridine (prepared by the method of W. O. Siegl, J. Heterocycl. Chem. 1981, 18, 1613–1618) were heated in a 135–140° C. oil bath for 2 h. The solution was concentrated on a rotary evaporator and the residue was chromatographed twice on silica gel, eluted with 30–50% ethyl acetate in dichloromethane to give 71 mg of pure 2-acetamido-4,5-dimethylpyridine.

$^1$H NMR (200 MHz, CDCl$_3$): δ 8.28 (bs, 1H), 8.00 (s, 1H), 7.97 (s, 1H), 2.29 (s, 3H), 2.19 (s, 3H), 2.17 (s, 3H).

Step B: 2-Amino-4,5-dimethylpyridine hydrochloride.

2-Acetamido-4,5-dimethylpyridine (50 mg, 0.30 mmol) was warmed in 3.0 mL of concentrated hydrochloric acid at 110–115° C. for 10 h. The solution was then concentrated to give 48 mg (100% yield) of 2-aniino-4,5-dimethylpyridine hydrochloride as a colorless white solid.

$^1$H NMR (400 MHz, CD$_3$OD): δ 7.57 (s, 1H), 6.82 (s, 1H), 2.35 (s, 3H), 2.17(s,3H).

EXAMPLE 50

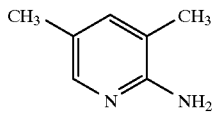

2-Amino-3,5-dimethylpyridine

The title compound wa prepared by the method of W. O. Siegl, J. Heterocycl. Chem. 1981, 18, 1613–8.

EXAMPLE 51

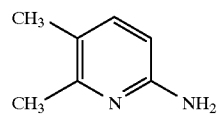

2-Amino-5,6-dimethylpyridine

The title compound was prepared by a modification of the method of G. Y. Lesher and M. D. Gruett, Belg. patent 612258, 1962.

EXAMPLE 52

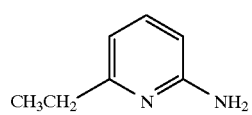

2-Amino-6-ethylpyridine

The title compound was prepared by the method of S. J. Childress and J. V. Scudi, J. Org. Chem., 1958, 23, 67–69.

EXAMPLE 53

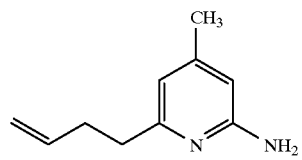

2-Amino-6-(3-buten-1-yl)-4-methylpyridine

Step A: 4,6-Dimethyl-2-(2,5-dimethylpyrrol-1-yl)pyridine.

A mixture of 2-amino-4,6-dimethylpyridine (20.0 g, 164 mmol), acetonylacetone (30 mL, 170 mmol), acetic acid (2.0 mL, 35 mmol), and sodium acetate trihydrate (200 mg, 1.5 mmol) in 140 mL of toluene was heated to reflux for 48 h in a flask connected to a Dean-Stark trap. After cooling to room temperature, the reaction mixture was washed with 50 mL each of 2.5 N aqueous sodium hydroxide, water, and saturated aqueous sodium chloride. The organic layer was dried (sodium sulfate), decanted, and evaporated. The residue was distilled through a 1×10 cm Vigreaux column to give 29.09 g (89% yield) of 4,6-dimethyl-2-(2,5-dimethylpyrrol-1-yl)pyridine as an almost colorless liquid boiling at 93–97° C. (0.05 mm).

$^1$H NMR (400 MHz, CDCl$_3$): δ 6.98 (s, 1H), 6.83 (s, 1H), 5.87 (s, 2H), 2.54 (s, 3H), 2.38 (s, 3H), 2.11 (s, 6H). Calc. for C$_{13}$H$_{16}$N$_2$: 77.96% C, 8.05% H, 13.99% N. Found: 77.53% C, 8.39% H, 14.34% N.

Step B: 6-(3-Buten-1-yl)-4-methyl-2-(2,5-dimethylpyrrol-1-yl)pyridine.

A solution of 213 mg (1.06 mmol) of 4,6-dimethyl-2-(2, 5-dimethylpyrrol-1-yl)pyridine in 1.2 mL of ethyl ether was added over a 5 min period to a –25° C. solution prepared from 1.2 mL of ethyl ether and 0.75 mL (1.09 mmol) of 1.45 M n-butyllithium in hexane. The mixture was stirred for 5 min at –25° C. and then allowed to warm to –5° C. over 10 min. Allyl bromide (0.105 mL, 147 mg, 1.21 mmol) was added and the mixture was allowed to warm to 10° C. over 1 h. Saturated aqueous ammonium chloride (10 mL) was added and the mixture was extracted with 20 mL of ethyl acetate. The organic layer was washed with 10 mL of saturated aqueous sodium chloride, dried (sodium sulfate), decanted, and evaporated. Column chromatography on 20 g of silica gel eluting with 5% ethyl acetate in hexane gave 175 mg (68% yield) of 6-(3-buten-1-yl)-4-methyl-2-(2,5-dimethylpyrrol-1-yl)pyridine as a colorless oil.

$^1$H NMR (400 MHz, CDCl$_3$): δ 6.98 (s, 1H), 6.86 (s, 1H), 5.88 (s, 2H), 5.86 (ddt, 1H, J=17, 10, 7 Hz), 5.03 (dq, 1H, J=17, 2 Hz), 4.97 (dm, 1H, J=10 Hz), 2.90 (t, 2H, J=7 Hz), 2,51 (q, 2H, J=7 Hz), 2.40 (s, 3H), 2.12 (s, 6H). Mass spectrum (FAB): m/e=241 (M+1).

Step C: 2-Amino-6-(3-buten-1-yl)-4-methylpyridine.

A mixture of 147 mg (0.612 mmol) of 6-(3-buten-1-yl)-4-methyl-2-(2,5-dimethylpyrrol-1-yl)pyridine and 215 mg (3.09 mmol) of hydroxylamine hydrochloride in 1.6 mL of 95% ethanol and 0.6 mL of water was heated overnight in a 100° C. oil bath. After cooling to room temperature, the solution was diluted with 25 mL of ethyl ether and washed with 15 mL of 2.5 N aqueous sodium hydroxide followed by 15 mL of saturated aqueous sodium chloride. The aqueous layers were extracted in succession with 25 mL of ethyl ether. The combined ethyl ether layers were dried (sodium sulfate), decanted, and evaporated. Flash column chromatography on 6 g of silica gel eluting with 100 mL of 1:1 ethyl acetate/dichloromethane gave 82 mg (83% yield) of 2-amino-6-(3-buten-1-yl)-4-methylpyridine as a pale yellow oil.

$^1$H NMR (400 MHz, CDCl$_3$): δ 6.37 (s, 1H), 6.20 (s, 1H), 5.87 (ddt, 1H, J=17, 10, 7 Hz), 5.06 (dq, 1H, J=17, 2 Hz), 4.98 (dm, 1H, J=10 Hz), 4,60 (bs, 2H), 2.69 (t, 2H, J=7 Hz), 2.44 (q, 2H, J=7 Hz), 2.22 (s, 3H). Mass spectrum (FAB): m/e=163 (M+1). Calc. for C$_{10}$H$_{14}$N$_2$: 74.02% C, 8.70% H, 17.28% N. Found: 73.82% C, 8.77% H, 17.43% N.

EXAMPLE 54

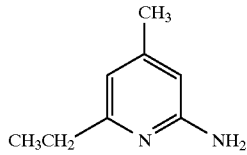

2-Amino-6-ethyl-4-methylpyridine

Step A: 6-Ethyl-4-methyl-2-(2,5-dimethylpyrrol-1-yl) pyridine.

By analogy to Example 53, Step B, 4,6-dimethyl-2-(2,5-dimethylpyrrol-1-yl)pyridine was treated with n-butyllithium and then iodomethane to give 6-ethyl-4-methyl-2-(2,5-dimethylpyrrol-1-yl)pyridine as a colorless oil in 64% yield.

$^1$H NMR (400 MHz, CDCl$_3$): δ 6.99 (s, 1H), 6.85 (s, 1H), 5.88 (s, 2H), 2.82 (q, 2H, J=7 Hz), 2.40 (s, 3H), 2.13 (s, 6H), 1.31 (t, 3H, J=7 Hz). Calc. for C$_{14}$H$_{18}$N$_2$: 78.46% C, 8.47% H, 13.07% N. Found: 78.39% C, 5.58% H, 13.24% N.

Step B: 2-Amino-6-ethyl-4-methylpyridine.

By analogy to Example 53, Step C, 6-ethyl-4-methyl-2-(2,5-dimethylpyrrol-1-yl)pyridine gave 2-amino-6-ethyl-4-methylpyridine as an almost colorless oil in 88% yield.

$^1$H NMR (400 MHz, CDCl$_3$): δ 6.38 (s, 1H), 6.20 (s, 1H), 4.63 (bs, 2H), 2.63 (q, 2H, J=7 Hz), 2.23 (s, 3H), 1.26 (t, 3H, J=7 Hz). Calc. for C$_8$H$_{12}$N$_2$: 70.55% C, 8.88% H, 20.57% N. Found: 70.26% C, 8.65% H, 20.46% N.

EXAMPLE 55

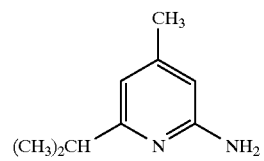

2-Amino-4-methyl-6-(1-methylethyl)pyridine

Step A: 4-Methyl-6-(1-methylethyl)-2-(2,5-dimethylpyrrol-1-yl)pyridine.

By analogy to Example 53, Step B, 6-ethyl-4-methyl-2-(2,5-dimethylpyrrol-1-yl)pyridine was treated with n-butyllithium and then iodomethane to give 4-methyl-6-(1-methylethyl)-2-(2,5-dimethylpyrrol-1-yl)pyridine as an almost colorless oil in 52% yield $^1$H NMR (400 MHz, CDCl$_3$): δ 6.99 (s, 1H), 6.84 (s, 1H), 5.89 (s, 2H), 3.11 (septet, 1H, J=7 Hz), 2.40 (s, 3H), 2.15 (s, 6H), 1.31 (d, 6H, J=7 Hz). Mass spectrum (FAB): m/e=229 (M+1).

Step B: 2-Amino-4-methyl-6-(1-methylethyl)pyridine.

By analogy to Example 53, Step C, 4-methyl-6-(1-methylethyl)-2-(2,5-dimethylpyrrol-1-yl)pyridine gave 2-amino-4-methyl-6-(1-methylethyl)pyridine in 69% yield as a colorless oil which spontaneously crystallized.

$^1$H NMR (400 MHz, CDCl$_3$): δ 6.38 (s, 1H), 6.17 (s, 1H), 4.37 (bs, 2H), 2.83 (septet, 1H, J=7 Hz), 2.21 (s, 3H), 1.24 (d, 6H, J=7 Hz). Mass spectrum (EI): m/e=150 (M$^+$). Calc. for C$_9$H$_{14}$N$_2$: 71.96% C, 9.39% H, 18.65% N. Found: 71.95% C, 9.26% H, 18.43% N.

EXAMPLE 56

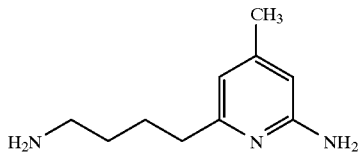

2-Amino-6-(4-aminobutyl)-4-methylpyridine

Step A: 4-Methyl-2-(2,5-dimethylpyrrol-1-yl)-6-(4-(2,5-dimethylpyrrol-1-yl)butyl)pyridine.

A solution of 297 mg (1.49 mmol) of 4,6-dimethyl-2-(2, 5-dimethylpyrrol-1-yl)pyridine (from Example 53, Step A) in 1.5 mL of ethyl ether was added to a −20° C. solution prepared from 3.0 mL of ethyl ether and 1.2 mL (1.7 mmol) of 1.4 M n-butyllithium in hexane. The mixture was stirred for 1 h at −20 to −15° C. with the formation of a preciptate. Tetrahydrofuran (1.0 mL) was added, the resulting orange-red solution was cooled to −45° C., and 400 mg (1.85 mmol) of 1-(3-bromopropyl)-2,5-dimethylpyrrole (S. P. Bruekelman, S. E. Leach, G. D. Meakins, and M. D. Tirel, J. Chem. Soc., Perkin Trans. 1, 1984, 2801–7) was added in one portion. The mixture was allowed to warm to 10° C. over 1.75 h, quenched with 10 mL of saturated aqueous ammonium chloride, and extracted with 20 mL of ethyl acetate. The organic layer was washed with 10 mL of saturated aqueous sodium chloride, dried (sodium sulfate), decanted, and evaporated. The residue was purified by flash column chromatography on 50 g of silica gel, eluting with 1.2 L of 5% ethyl acetate in hexane to give 402 mg (80% yield) of 4-methyl-2-(2,5-dimethylpyrrol-1-yl)-6-(4-(2,5-dimethylpyrrol-1-yl)butyl)pyridine as an almost colorless oil.

$^1$H NMR (400 MHz, CDCl$_3$): δ 6.94 (s, 1H), 6.86 (s, 1H), 5.88 (s, 2H), 5.75 (s, 2H), 3.73 (t, 2H, J=7 Hz), 2.81 (t, 2H,

J=7 Hz), 2.38 (s, 3H), 2.18 (s, 6H), 2.11 (2, 6H), 1.82 (quintet, 2H, J=7 Hz), 1.64 (quintet, 2H, J=7Hz). Mass spectrum (EI): m/e=335 (M+). Calc. for $C_{22}H_{29}N_3$: 78.76% C, 8.71% H, 12.52% N. Found: 78.68% C, 8.65% H, 12.45% N.

Step B: 2-Amino-6-(4-aminobutyl)-4-methylpyridine.

4-Methyl-2-(2,5-dimethylpyrrol-1-yl)-6-(4-(2,5-dimethylpyrrol-1-yl)butyl)pyridine (429 mg, 1.28 mmol) was dissolved in 6.5 mL of 95% ethanol and 2.5 mL of water was added followed by 818 mg (11.8 mmol) of hydroxylamine hydrochloride and 450 mg (6.96 mmol) of 87% potassium hydroxide. The mixture was heated in a 100° C. oil bath for 18 h. After cooling the reaction to room temperature, most of the ethanol was removed on a rotary evaporator. The residue was partitioned between 10 mL of 2 N aqueous hydrochloric acid and 20 mL of ethyl ether. The aqueous layer was made strongly basic by the addition of solid 87% potassium hydroxide and then extracted with 3×20 mL of ethyl ether. The combined ethyl ether extracts were dried over potassium hydroxide and sodium sulfate, decanted, and evaporated. The residue was purified by flash column chromatography on 6 g of silica gel eluting with 100 mL of 1% ammonium hydroxide and 7% methanol in dichloromethane followed by 100 mL of 2% ammonium hydroxide and 10% methanol in dichloromethane to give 172 mg (75% yield) of 2-amino-6-(4-aminobutyl)-4-methylpyridine as a light amber oil.

$^1$H NMR (400 MHz, $CDCl_3$): δ 6.37 (s, 1H), 6.16 (s, 1H), 4.29 (bs, 2H), 2.72 (t, 2H, J=7 Hz), 2,57 (t, 2H, J=7 Hz), 2.19 (s, 3H), 1.70 (quintet, 2H, J=7 Hz), 1.50 (quintet, 2H, J=7 Hz). Mass spectrum (FAB): m/e=180 (M+1).

EXAMPLE 57

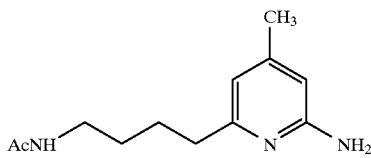

6-(4-Acetamidobutyl)-2-amino-4-methylpyridine

Triethylamine (0.059 mL, 43 mg, 0.42 mmol) and acetic anhydride (0.029 mL, 31 mg, 0.031 mmol) were added to a solution of 50 mg (0.028 mmol) of 2-amino-6-(4-aminobutyl)-4-methylpyridine (from Example 56) in 1.0 mL of dichloromethane. The solution was allowed to stand for 48 h at room temperature, then diluted with 25 mL of ethyl acetate and washed with 12 mL of saturated aqueous sodium bicarbonate and 12 mL of saturated aqueous sodium chloride. The aqueous layers were extracted in succession with 15 mL of ethyl acetate. The combined organic layers were dried (sodium sulfate), decanted, and evaporated. The residue was purified by flash column chromatography on 3.5 g of silica gel, eluting with 100 mL of 5% methanol in dichloromethane to give 27 mg (44% yield of 6-(4-acetamidobutyl)-2-amino-4-methylpyridine as an oil which spontaneously crystallized.

$^1$H NMR (400 MHz, $CDCl_3$): δ 6.35 (s, 1H), 6.17 (s, 1H), 5.76 (bs, 1H), 4.32 (bs, 2H), 3.27 (q, 2H, J=7 Hz), 2,58 (t, 2H, J=7 Hz), 2.20 (s, 3H), 1.97 (s, 3H), 1.71 (quintet, 2H, J=7 Hz), 1.55 (quintet, 2H, J=7 Hz). Mass spectrum (FAB): m/e=222 (M+1).

EXAMPLE 58

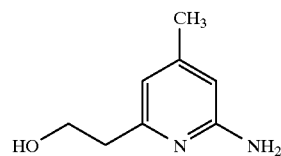

2-Amino-6-(2-hydroxyethyl)-4-methylpyridine

Step A: 6-(2-Hydroxyethyl)-4-methyl-2-(2,5-dimethylpyrrol-1-yl)pyridine.

A solution of 2.97 mg (14.8 mmol) of 4,6-dimethyl-2-(2,5-dimethylpyrrol-1-yl)pyridine (from Example 53, Step A) in 15 mL of ethyl ether was added to a −20° C. solution prepared from 30 mL of ethyl ether and 12 mL (17 mmol) of 1.4 M n-butyllithium in hexane. The mixture was stirred for 1 h at −20 to −15° C. with the formation of a precipitate. Tetrahydrofuran (10 mL) was added, giving an orange-red solution of the intermediate anion. Paraformaldehyde in a separate flask was heated to 150–160° C., generating formaldehyde gas. The formaldehyde, diluted with nitrogen, was introduced as a gas stream impinging on the anion solution (kept at −15 to −10° C.) until the anion color had faded (20–30 min). The mixture was stirred an additional 15 min, quenched by the addition of 50 mL of saturated aqueous ammonium chloride, and extracted with 50 mL of ethyl acetate. The organic layer was washed with 30 mL of saturated aqueous sodium choride, dried (sodium sulfate), decanted, and evaporated. The residue was purified by flash column chromatography on 90 g of silica gel eluting with 2 L of 30% ethyl acetate in hexane to give 1.55 g (45% yield) of 6-(2-hydroxyethyl)-4-methyl-2-(2,5-dimethylpyrrol-1-yl) pyridine as a colorless oil.

$^1$H NMR (400 MHz, $CDCl_3$): δ 7.00 (s, 1H), 6.90 (s, 1H), 5.89 (s, 2H), 4.02 (q, 2H, J=5 Hz), 3.78 (t, 1H, J=5 Hz), 3.02 (t, 2H, J=5 Hz), 2.40 (s, 3H), 2.13 (s, 6H). Mass spectrum (FAB): m/e=231 (M+1).

Step B: 2-Amino-6-(2-hydroxyethyl)-4-methylpyridine.

6-(2-Hydroxyethyl)-4-methyl-2-(2,5-dimethylpyrrol-1-yl)pyridine (457 mg, 1.98 mmol) was dissolved in 5.0 mL of 95% ethanol and 2.0 mL of water was added followed by 625 mg (8.99 mmol) of hydroxylamine hydrochloride and 350 mg (5.36 mmol) of 86% potassium hydroxide. The mixture was heated in a 100° C. oil bath for 24 h, the cooled to room temperature and partitoned between 15 mL of 2 N aqueous hydrochloric acid and 30 mL of dichloromethane. The aqueous layer was made strongly basic by the addition of solid 86% potassium hydroxide and extracted with 3×30 mL of ethyl ether. The ethyl ether layers were dried (sodium sulfate), decanted, and evaporated. The residue was purified by flash column chromatography on 25 g of silica gel, eluting with 20% isopropanol in dichloromethane to give 201 mg (67% yield) of 2-amino-6-(2-hydroxyethyl)4-methylpyridine as a colorless oil which spontaneously crystallized.

$^1$H NMR (400 MHz, $CDCl_3$): δ 6.35 (s, 1H), 6.20 (s, 1H), 4.32 (bs, 2H), 3.94 (t, 2H, J=6 Hz), 2.80 (t, 2H, J=6 Hz), 2.20 (s, 3H). Mass spectrum (FAB): m/e=153 (M+1).

EXAMPLE 59

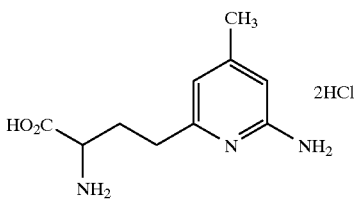

α-(2-(6-Amino-4-methylpyrid-2-yl)ethyl)glycine dihydrochloride

Step A: 6-(2-Methanesulfonyloxyethyl)-4-methyl-2-(2,5-dimethylpyrrol-1-yl)pyridine.

A solution of 2.00 g (8.68 mmol) of 6-(2-hydroxyethyl)-4-methyl-2-(2,5-dimethylpyrrol-1-yl)pyridine (from Example 58, Step A) and 1.82 mL (1.32 g, 13.1 mmol) of triethylamine in 20 mL of dichloromethane was cooled to 0° C. and 0.68 mL (1.0 g, 8.8 mmol) of methanesulfonyl chloride was added over 5 min. The mixture was stirred another 25 min at 0° C., diluted with 70 mL of ethyl acetate, and washed with 30 mL each of water, saturated aqueous sodium bicarbonate, and saturated aqueous sodium chloride. The organic layer was dried (sodium sulfate), decanted, and evaporated to give 2.68 g (100% yield) of 6-(2-methanesulfonyloxyethyl)-4-methyl-2-(2,5-dimethylpyrrol-1-yl)pyridine as a viscous pink oil.

$^1$H NMR (400 MHz, CDCl$_3$): δ 7.04 (s, 2H), 6.93 (s, 2H), 5.90 (s, 2H), 4,66 (t, 2H, J=6 Hz), 3.22 (t, 2H, J=6 Hz), 2.91 (s, 3H), 2.42 (s, 3H), 2.13 (s, 6H).

Step B: Diethyl 2-acetamido-2-(2-(6-amino-4-methylpyrid-2-yl)ethyl)malonate.

Sodium hydride (52 mg of 60% oil dispersion, 1.30 mmol) was added to a solution of 310 mg (1.43 mmol) of diethyl acetamidomalonate in 2.0 mL of N,N-dimethylformamide. After 30 min, 72 mg (0.20 mmol) of tetrabutylammonium iodide was added followed by 200 mg (0.65 mmol) of $^6$-(2-methanesulfonyloxyethyl)-4-methyl-2-(2,5-dimethylpyrrol-1-yl)pyridine in 1.0 mL of N,N-dimethylformamide. The reaction was stirred at room temperature for 30 min, at 60° C. for 20 h, and at room temperature for 3 d. The reaction was diluted with 30. mL of ethyl acetate and washed with 15 mL each of saturated aqueous sodium bicarbonate and saturated aqueous sodium chloride. The aqueous layers were extracted in succession with 30 mL of ethyl acetate. The combined organic layers were dried (sodium sulfate), decanted, and evaporated. The crude product was purified by flash column chromatography on 15 g of silica gel, eluting with 300 mL of 10% ethyl acetate in dichloromethane to give 243 mg (87% yield) of diethyl 2-acetamido-2-(2-(6-amino-4-methylpyrid-2-yl)ethyl)malonate as a tan solid.

$^1$H NMR (400 MHz, CDCl$_3$): δ 6.97 (s, 1H), 6.85 (s, 1H), 5.87 (s, 2H), 4.31–4.17 (m, 4H), 2.79–2.72 (m, 2H), 2.70–2.63 (m, 2H), 2.37 (s, 3H), 2.12 (s, 6H), 2.01 (s, 3H), 1.26 (t, 3H, J=7 Hz). Mass spectrum (FAB): m/e=430 (M+1).

Step C: N-Acetyl-α-(2-(6-amino-4-methylpyrid-2-yl)ethyl)glycine methyl ester.

Diethyl 2-acetamido-2-(2-(6-amino-4-methylpyrid-2-yl)ethyl)malonate (2,54 g, 5.92 mmol) was dissolved in 38 ml of 95% ethanol. Water (7.5 mL) and 87% potassium hydroxide (2,55 g, 39.4 mmol) were added and the solution was stirred at room temperature for 6 h. Hydroxylamine hydrochloride (3.87 g, 55.7 mmol) and water (7.5 mL) were added and the mixture was heated in a 100° C. oil bath for 14 h. The reaction mixture was poured into 120 mL of 2 N aqueous hydrochloric acid and washed with 2×120 mL of ethyl ether. The aqueous layer was evaporated and the residue was triturated with 40 mL of methanol and then 4×10 mL of methanol. The methanol extracts were evaporated to give 6.63 g of residue. A solution of 2.98 g of this residue in 13.5 mL of water was loaded on to an ion exchange column packed with 100 mL of Dowex 1X8-100 resin in the hydroxide form. The column was washed with 400 mL of water and 800 mL of 0.5 N aqueous hydrochloric acid. The column was regenerated and then another 2.98 g of the residue was passed down the column. The acid elution fractions were pooled and evaporated to give 2,54 g of orange foam. This material was dissolved in 100 mL of methanol and treated with excess diazomethane in ether. After quenching with acetic acid and evaporation of the solvent, the residue was dissolved in 100 mL of ethyl acetate and washed with 50 mL each of saturated aqueous sodium bicarbonate and saturated aqueous sodium chloride. The aqueous layers were extacted in succession with 100 mL of ethyl acetate. The combined organic layers were dried (sodium sulfate), decanted, and evaporated to give 1.46 g of orange film. Flash column chromatography on 40 g of silica gel eluting with 800 mL of 50% ethyl acetate in dichloromethane followed by 1 L of 5–10% methanol in dichloromethane gave 547 mg of slightly impure product. Chromatography on 40 g of silica gel eluting with 1% ammonium hydroxide and 10% isopropanol in dichloromethane gave 473 mg (30% yield) of N-acetyl-α-(2-(6-amino-4-methylpyrid-2-yl)ethyl)glycine methyl ester.

$^1$H NMR (400 MHz, CDCl$_3$): δ 6.79 (d, 1H, J=7 Hz), 6.33 (s, 1H), 6.15 (s, 1H), 4,60 (td, 1H, J=7, 5 Hz), 4.29 (bs, 2H), 3.69 (s, 3H), 2.69–2.54 (m, 2H), 2.24–2.04 (m, 2H), 2.17 (s, 3H), 1.98 (s, 3H). Mass spectrum (FAB): m/e=266 (M+1).

Step D: α-(2-(6-Amino-4-methylpyrid-2-yl)ethyl)glycine dihydrochloride.

N-Acetyl-α-(2-(6-amino-4-methylpyrid-2-yl)ethyl)glycine methyl ester (200 mg, 0.75 mmol) was heated in 6.0 mL of refluxing 2 N aqueous hydrochloric acid for 2.5 h. The solution was cooled and evaporated. The residue was dissolved in 2.75 mL of warm methanol and the solution was concentrated to a volume of 1–1.5 mL. Ethyl acetate (1.0 mL) and seed crystals were added. The crystals were separated using a Craig tube and recrystallized again to give 122 mg (58% yield) of α-(2-(6-amino-4-methylpyrid-2-yl)ethyl) glycine dihydrochloride as white crystals.

$^1$H NMR (400 MHz, CD$_3$OD): δ 6.68 (s, 1H), 6.66 (s, 1H), 4.06 (t, 1H, J=6 Hz), 3.04–2.86 (m, 2H), 2.39–2.20 (m, 2H), 2.37 (s, 3H). Calc. for C$_{10}$H$_{17}$Cl$_2$N$_3$O$_2$: 42.57% C, 6.07% H, 14.89% N. Found: 42.61% C, 6.06% H, 14.73% N.

EXAMPLE 60

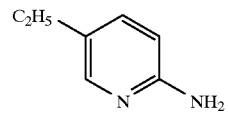

2-Amino-5-ethylpyridine

Step A: 3-(5-Ethyl-2-pyridinyl)-2,2-dimethyl-2,3-dihydro-(4h)-1,3-benzoxazin-4-one.

A solution of 172 mg (0.87 mmol) of 4-chloro-2,2-dimethyl-(2H)-1,3-benzoxazine (K. Wachi and A. Terada, *Chem. Pharm. Bull*, 1980, 28, 465–472) and 215 mg (1.75 mmol) of 3-ethylpyridine N-oxide (S. Hibino and E. Sugino, *J. Heterocycl Chem.*, 1990, 27, 175) in 1.6 mL of methylene chloride was heated to reflux for 9 h with stirring. After cooling the reaction, 30 mL ethyl acetate was added and the mixture was washed in succession with 10 mL saturated sodium bicarbonate and 10 mL of saturated aqueous sodium chloride. The organic solution was dried (sodium sulfate), decanted, and evaporated to give a yellow liquid. Flash column chromatography on 17 g of silica gel, eluting with 100 mL of 5% ethyl acetate/hexane and 500 mL of 7% ethyl acetate/hexane furnished 84 mg (33% yield) of 3-(5-ethyl-2-pyridinyl)-2,2-dimethyl-2,3-dihydro-(4H)-1,3-benzoxazin-4-one as a colorless syrup.

$^1$H NMR (400 MHz, CDCl$_3$): δ 8.36 (dd, 1H, J=3, 1 Hz), 7.97 (dd, 1H, J=8, 2 Hz), 7.58 (dd, 1H, J=8, 3 Hz), 7.46 (td, 1H, J=8, 2 Hz), 7.21 (d, 1H, J=8 Hz), 7.07 (td, 1H, J=8, 2 Hz), 6.94 (dd, 1H, J=8, 1 Hz), 2.68 (q, 2H, J=7 Hz), 1.71 (s, 6H), 1.27 (t, 3H, J=7 Hz). Mass spectrum (FAB): m/e=283 (M+1).

Step B: 2-Amino-5-ethylpyridine

Following the general method of K. Wachi and A. Terada (*Chem. Pharm. Bull.*, 1980, 28, 465–472), a mixture 81 mg (0.29 mmoles) of 3-(5-ethyl-2-pyridinyl)-2,2-dimethyl-2.3-dihydro-(4H)-1,3-benzoxazin-4-one and 2.0 mL of concentrated hydrochloric acid was heated to reflux for 8 h. The reaction was cooled to room temperature and the solvent was evaporated. The residue was dissolved in 4 mL ethyl acetate and washed with 3×1 mL of a 1:1 mixture of 10% of aqueous sodium hydroxide solution and saturated aqueous sodium chloride. The organic solution was dried (sodium sulfate), decanted, and evaporated to give 26 mg (84% yield) of 2-amino-5-ethylpyridine as an amber oil.

$^1$H NMR (400 MHz, CD$_3$OD): δ 7.71 (bs, 1H), 7.34 (dd, 1H, J=8,2 Hz), 6.53 (d, 1H, J=8 Hz), 2.48 (q, 2H, J=7 Hz), 1. 16 (t, 3H, J=7 Hz).

EXAMPLE 61

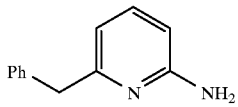

2-Amino-6-benzylpyridine

Step A: 2-Benzylpyridine N-oxide.

A stirred solution of 3.0 g (18 mmol) 2-benzylpyridine and 1.65 mL of 30% aqueous hydrogen peroxide in 5.0 mL of acetic acid was heated at 100° C. for 3 hr (S. Hibino and E. Sugino, *J. Heterocycl Chem.*, 1990, 27, 175). After cooling to room temperature, the reaction was diluted with 30 mL ethyl acetate and neutralized with sodium carbonate. The sodium acetate was separated by filtration and the filtrate was dried (sodium carbonate) and concentrated to give a yellow oil. Flash column chromatography on 125 g of silica gel using 7 of L 20% acetone/ethyl acetate furnished 2,58 g (79% yield) of 2-benzylpyridine N-oxide as an amber syrup.

$^1$H NMR (400 MHz, CDCl$_3$): δ 8.29–8.26 (m, 1H), 7.37–7.30 (m, 2H), 7.30–7.22 (m, 3H), 7.14–7.10 (m, 2H), 6.93–6.89 (m, 1H), 4.25 (s, 2H). Mass spectrum (FAB): m/e=170 (M-15).

Step B: 2,2-Dimethyl-3-(6-phenylmethyl-2-pyridinyl)-2,3-dihydro-(4H)-1,3-benzoxazin-4-one.

By analogy to Example 60, Step A, 2-benzylpyridine N-oxide was converted into 2,2-dimethyl-3-(6-phenylmethyl-2-pyridinyl)-2,3-dihydro-(4H)-1,3-benzoxazin4-one.

$^1$H NMR (400 MHz, CDCl$_3$): δ 7.97 (dd, 1H, J=8, 2 Hz), 7.64 (t, 1H, J=8 Hz), 7.46 (td, 1H, J=8, 2 Hz), 7.31–7.17 (m, 5H), 7.12 (d, 1H, J=8 Hz), 7.07 (t, 1 H, J=7Hz), 7.06 (d, 1H, J=7 Hz), 6.93 (d, 1H, J=8 Hz), 4.12 (s, 2H), 1.65 (s, 6H). Mass spectrum (FAB): m/e=345 (M+1).

Step C: 2-Amino-6-benzylpyridine

By analogy to Example 60, Step B, 2,2-dimethyl-3-(6-benzyl-2-pyridinyl)-2,3-dihydro-(4H)-1,3-benzoxazin-4-one was converted into 2-amino-6-benzylpyridine.

$^1$H NMR (400 MHz, CDCl$_3$): δ 7.33–7.16 (m, 6H), 6.40 (d, 1H, J=7 Hz), 6.30 (d, 1H, J=8 Hz), 4.40 (bs, 2H), 3.95 (s, 2H). Mass spectrum (FAB): m/e=185 (M+1).

EXAMPLE 62

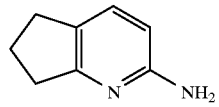

2-Amino-6,7-dihydro-(5H)-pyrindine

Step A: 6,7-Dihydro-(5H)-pyrindine N-oxide.

By analogy to Example 61, Step A, 3.0 g (25.2 mmol) of 6,7-dihydro-(5H)-pyrindine was converted into crude 6,7-Dihydro-(5H)-pyrindine N-oxide. Flash column chromatography on 100 g of silica gel, eluting with 4 L of 50% ethyl acetate/dichloromethane and 2.5 L of 5% methanol/ dichloromethane furnished 2.7 g (88% yield) of 6,7-Dihydro-(5H)-pyrindine N-oxide as a white solid.

$^1$H NMR (400 MHz, CDCl$_3$): δ 8.02 (d, 1H, J=6 Hz), 7.09 (d, 1H, J=7 Hz), 7.04 (t, 1H, J=7 Hz), 3.15 (t, 2H, J=7 Hz), 3.00 (t, 2H, J=7 Hz), 2.16 (quintet, 2H, J=7 Hz). Mass spectrum (FAB): m/e=120 (M-15).

Step B: 3-(6,7-Dihydro-(5H)-1-pyrindin-2-yl)-2,2-dimethyl-2,3-dihydro-(4H)-1,3-benzoxazin-4-one.

By analogy to Example 60, Step A, 6,7-Dihydro-(5H)-pyrindine N-oxide was converted into 3-(6,7-dihydro-(5H)-1-pyrindin-2-yl)-2,2-dimethyl-2,3-dihydro-(4H)-1,3-benzoxazin-4-one.

$^1$H NMR (400 MHz, CDCl$_3$): δ 7.86 (dd, 1H, J=8, 2 Hz), 7.55 (d, 1H, J=8 Hz), 7.45 (td, 1H, J=8, 2 Hz), 7.06 (td, 1H, J=8, 1 Hz), 7.01 (d, 1H, J=8 Hz), 6.93 (d, 1H, J=8 Hz), 2.99 (t, 2H, J=7 Hz), 2.94 (t, 2H, J=7 Hz), 2.14 (quintet, 2H, J=7 Hz), 1.70 (s, 6H). Mass spectrum (FAB): m/e=295 (M+1). Calc. for C$_{18}$H$_{18}$N$_2$O$_2$: C$_{73.45}$% C, 6.16% H, 9.52% N. Found: 73.21% C, 5.95% H, 9.43% N.

Step C: 2-Amino-6,7-dihydro-(5H)-pyrindine

By analogy to Example 60, Step B, 3-(6,7-dihydro-(5H)-1-pyrindin-2-yl)-2,2-dimethyl-2,3-dihydro-(4H)-1,3-benzoxazin-4-one gave 2-amino-6,7-dihydro-(5H)-pyrindine as a white solid in 44% yield.

$^1$H NMR (400 MHz, CDCl$_3$): δ 7.27 (d, 1H, J=8 Hz), 6.28 (d, 1H, J=8 Hz), 4.27 (br, 2H), 2.85 (t, 2H, J=7 Hz), 2.80 (t, 2H, J=7 Hz), 2.08 (quintet, 2H, J=7 Hz). Mass spectrum (EI): m/e=133 (M-1).

EXAMPLE 63

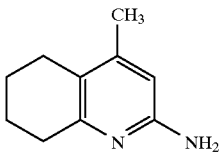

2-Amino-4-methyl-5,6,7,8-tetrahydroquinoline

Step A: 4-Methyl-5,6,7,8-tetrahydroquinoline

Using the general method of F. W. Vierhapper and E. L. Eliel (*J. Org. Chem.*, 1975, 40, 2729), a solution of 4.97 g (34.7 mmol) of lepidine in 35 mL of trifluoroacetic acid was shaken with 580 mg of platinum oxide under 50 psi of hydrogen for 18 h. After filtering off the catalyst, the solution was concentrated to about 20 mL and diluted with 25 mL of water. The aquous solution was chilled in ice, and basified carefully with 35 mL of 50% aqueous sodium hydroxide. The aqeuous layer was then extracted with 4×50 mL of diethyl ether. The organic layers were dried over potassium hydroxide, decanted, and concentrated to yield 4.7 g (92% yield) of 4-methyl-5,6,7,8-tetrahydroquinoline as an amber oil.

¹H NMR (400 MHz, CDCl₃): δ 8.20 (d, 1H, J=5 Hz), 6.86 (d, 1H, J=5 Hz), 2.88 (t, 2H, J=6 Hz), 2.62 (t, 2H, J=6 Hz), 2.18 (s, 3H), 1.88–1.78 (m, 4H).

Step B: 2-Amino-4-methyl-5,6,7,8-tetrahydroquinoline.

Following the general method of W. O. Siegl, (*J. Heterocycl. Chem.*, 1981, 18, 1613–18), 4-methyl-5,6,7,8-tetrahydroquinoline (1.47 g, 10.0 mmol) and 2.0 mL of N,N-dimethylaniline were added to 438 mg sodium amide (11.2 mmol) in a round bottom flask fitted with a mechanical stirrer and a reflux condenser. The mixture was heated at 180° C. under nitrogen for 24 h. The mixture was poured onto crushed ice and stirred until gas evolution ceased. The aquous solution was extracted with 5×15 mL of diethyl ether. The organic solution was dried (sodium sulfate), decanted and concentrated to give a red liquid which was purified by flash column chromatography on 200 g of silica gel, eluting with 500 mL of dichloromethane, 1L of 50% ethyl acetate/dichloromethane, 2 L of 80% ethyl acetate/dichloromethane, and 1L of ethyl acetate to give 254 mg of pink crystals. Kugelrohr distillation at 100–120° C. (0.3 mm) yielded 230 mg (15% yield) of 2-amino-4-methyl-5,6,7,8-tetrahydroquinoline as a white solid.

¹H NMR (400 MHz, CDCl₃): δ 6.19 (s, 1H), 4.10 (bs, 2H), 2.69 (t, 2H, J=5 Hz), 2.48 (t, 2H, J=5 Hz), 2.08 (s, 3H), 1.82–1.72 (m, 4H). Mass spectrum (FAB): m/e=149 (M+1).

EXAMPLE 64

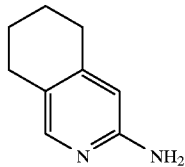

3-Amino-5,6,7,8-tetrahydroisoquinoline

Using the method of Example 63, Step A, 75 mg of 3-aminoisoquinoline (7.73 mmoles) and 8.7 mg platinum oxide in 2 mL of trifluoroacetic acid was shaken under 40 psi of hydrogen for 3 h. The mixture was filtered and catalyst was washed with ethyl acetate. After concentrating the filtrate, the residue was dissolved in 10 mL of ethyl acetate and washed with 5 mL of saturated aquous sodium bicarbonate. The organic solution was dried (sodium sulfate), decanted, and concentrated to give a yellow syrup. Flash coumn chromatography on 19 g of silica gel, eluting with 600 mL of 50% ethyl acetate/hexane gave 26.5 mg (34% yield) of 3-amino-5,6,7,8-tetrahydroisoquinoline as a pale yellow solid.

¹H NMR (400 MHz, CDCl₃): δ 7.78 (s, 1H), 6.22 (s, 1H), 4.12 (bs, 2H), 2.65–2.56 (m, 4H), 1.78–1.68 (m, 4H). Mass spectrum (FAB): m/e=149 (M+1)

EXAMPLE 65

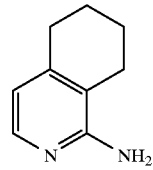

1-Amino-5,6,7,8-tetrahydroisoquinoline

Using the method described in Example 63, Step B, a mixture of 2.0 g (15.0 mmol) of 5,6,7,8-tetrahydroisoquinoline and 644 mg (16.5 mmol) of sodium amide in 2.5 mL of xylene was stirred at 150° C. overnight. The crude material was purified by flash column chromatography on silica gel eluting with 0–100% ethyl acetate/dichloromethane, and the partially purified material was distilled using a Kugelrohr apparatus at 100–105° C. (0.3 mm). Recrystallization of the distallate from a hexane/toluene mixture gave 120 mg of 1-amino-5,6,7,8-tetrahydroisoquinoline as a white solid containing approximately 7% of 1-aminoisoquinoline.

¹H NMR (400 MHz, CDCl₃): δ 7.78 (d, 1H, J=5 Hz), 6.41 (d, 1H, J=5 Hz), 4.28 (bs, 2H), 2.63 (t, 2H, J=6 Hz), 2.36 (t, 2H, J=6Hz), 1.88–1.80 (m, 2H), 1.78–1.70 (m, 2H). Mass spectrum (FAB): m/e=149 (M+1).

EXAMPLE 66

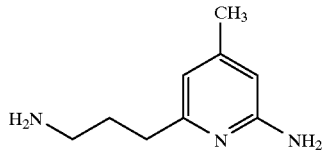

2-Amino-6-(3-aminopropyl)-4-methylpyridine

Step A: 1-(2-Bromoethyl)-2,6-dimethylpyrrole.

By analogy to the preparation of 1-(3-bromopropyl)-2,5-dimethylpyrrole (S. P. Bruekelman, S. E. Leach, C. D. Meakins, and M. D. Tiral, *J. Chem. Soc. Perkin Trans.* 1, 1984, 2801–7), 2-bromoethylamine hydrobromide was converted into 1-(2-bromoethyl)-2,6-dimethylpyrrole.

¹H NMR (400 MHz, CDCl₃): δ 5.79 (s, 2H), 4.11 (t, 2H, J=8 Hz), 3.40 (t, 2H, J=8 Hz), 2.24 (s, 6H). Mass spectrum (FAB): m/e=202 (M+1).

Step B: 4-Methyl-2-(2,5-dimethylpyrrol-1-yl)-6-(3-(2,5-dimethylpyrrol-1-yl)propyl)pyridine.

By analogy to Example 53, Step B, 1-(2-bromoethyl)-2, 6-dimethylpyrrole was converted into 4-methyl-2-(2,5-dimethylpyrrol-1-yl)-6-(3-(2,5-dimethylpyrrol-1-yl)propyl) pyridine.

¹H NMR (400 MHz, CDCl₃): δ 6.95 (s, 1H), 6.85 (s, 1H), 5.86 (s, 2H), 5.73 (s, 2H), 3.78 (t, 2H, J=8 Hz), 2.80 (t, 2H, J=8 Hz), 2.37(s, 3H), 2.16 (s, 6H), 2.09 (s, 6H), 2.09–1.98 (m, 2H). Mass spectrum (FAB): m/e=322 (M+1).

Step C: 2-Amino-6-(3-aminopropyl)-4-methylpyridine.

By analogy to Example 56, Step B, 4-methyl-2-(2,5-dimethylpyrrol-1-yl)-6-(3-(2,5-dimethylpyrrol-1-yl)propyl) pyridine was treated with 9.2 equivalents of hydroxylamine hydrochloride and 5.4 equivalents of potassium hydroxide in refluxing ethanol/water to yield 2-amino-6-(3-aminopropyl)-4-methylpyridine.

¹H NMR (400 MHz, CD₃OD): δ 6.36 (s, 1H), 6.43 (s, 1H), 2.62 (t, 2H, J=7 Hz), 2,54 (t, 2H, J=7 Hz), 2.18 (s, 3H), 1.79 (quintet, 2H, J=7 Hz). Mass spectrum (FAB): m/e=166 (M+1).

EXAMPLE 67

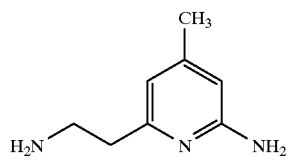

2-Amino-6-(2-aminoethyl)-4-methylpyridine

Step A: 4-Methyl-2-(2,5-dimethylpyrrol-1-yl)-6-(2-phthalimidoethyl)pyridine.

To a stirred solution of 250 mg (0.906 mmol) of 6-(2-methanesulfonyloxyethyl)-4-methyl-2-(2,5-dimethylpyrrol-1-yl)pyridine (from Example 59, Step A) in 0.70 mL of dry N,N-dimethylformide was added 336 mg (1.81 mmol) of potassium phthalimide and 67 mg (0.18 mmol) of tetrabutylammonium iodide. The mixture was stirred at room temperature for 2 h and at 40° C. for 20 h. The reaction was diluted with 50 mL of dichloromethane, washed with 30 mL of saturated aqueous sodium bicarbonate and 30 mL of saturated aqueous sodium chloride, dried (sodium sulfate), decanted, and evaporated. To remove the contaminating phthalimide, the residue was dissolved in 40 mL of diethyl ether and washed 2×20 mL of 2.5 N aqueous sodium hydroxide, followed by saturated aqueous sodium chloride. The organic phase was dried (sodium sulfate), decanted, and concentrated. Flash column chromatography on 26 g of silica gel, eluting with 200 mL of 7% of ethyl acetate/hexane and 500 mL of 30% of ethyl acetate/hexane furnished 206 mg (63% yield) of 4-methyl-2-(2,5-dimethylpyrrol-1-yl)-6-(2-phthalimidoethyl)pyridine as an amber syrup.

$^1$H NMR (400 MHz, CDCl$_3$): δ 7.78 (dd, 2H, J=6, 3 Hz), 7.66 (dd, 2H, J=6, 3 Hz), 6.96 (s, 1H), 6.84 (s, 1H), 5.81 (s, 2H), 4.07 (t, 2H, J=7 Hz), 3.13 (t, 2H, J=7 Hz), 2.33 (s, 3H), 2.06 (s, 6H). Mass spectrum (FAB): m/e=360 (M+1).

Step B: 6-(2-Aminoethyl)4-methyl-2-(2,5-dimethylpyrrol-1-yl)pyridine.

To a solution of 4-methyl-2-(2,5-dimethylpyrrol-1-yl)-6-(2-phthalimidoethyl)pyridine (100 mg, 0.28 mmol) in 1.0 mL of methanol under nitrogen at room temperature was added hydrazine (0.018 mL, 0.56 mmol) via syringe. The mixture was stirred at room temperature overnight. Dichloromethane (2.0 mL) was added to the reaction. The precipitate was removed by filtration and washed with another 2 mL of dichloromethane. The combined filtrates were concentrated. The resulting residue was chromatographed on 7 g of silica gel, eluting with 100 mL of 5% methanol/dichloromethane followed by 200 mL of 96:4:1 dichloromethane/methanol/triethylamine to give 44 mg (68% yield) of 6-(2-aminoethyl)-4-methyl-2-(2,5-dimethylpyrrol-1-yl)pyridine as colorless syrup.

$^1$H NMR (400 MHz, CDCl$_3$): δ 6.98 (s, 1H), 6.86 (s, 1H), 5.86 (s, 2H), 3.15 (t, 2H, J=6 Hz), 2.95 (t, 2H, J=6 Hz), 2.67 (bs, 2H), 2.37 (s, 3H), 2.10 (s, 6H). Mass spectrum (FAB): m/e=230(M+1).

Step C: 2-Amino-6-(2-aminoethyl)-4-methylpyridine.

By analogy to Example 56, Step B, 6-(2-aminoethyl)-4-methyl-2-(2,5-dimethylpyrrol-1-yl)pyridine was treated with 4.6 equivalents of hydroxylamine hydrochloride and 3.2 equivalents of potassium hydroxide in refluxing ethanol/water to yield 2-amino-6-(2-aminoethyl)-4-methylpyridine.

$^1$H NMR (400 MHz, CD$_3$OD): δ 6.35 (s, 1H), 6.26 (s, 1H), 2.91 (t, 2H, J=7 Hz), 2.66 (t, 2H, J=7 Hz), 2.18 (s, 3H). Mass spectrum (FAB): m/e=152 (M+1).

EXAMPLE 68

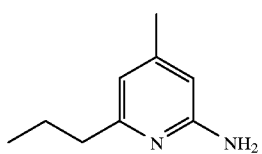

2-Amino-4-methyl-6-propylpyridine

Step A: 4-Methyl-2-(2,5-dimethylpyrrol-1-yl)-6-propylpyridine.

By analogy to Example 53, Step B, the anion of 4,6-dimethyl-2-(2,5-dimethylpyrrol-1-yl)pyridine was alkylated with bromoethane to give 4-methyl-2-(2,5-dimethylpyrrol-1-yl)-6-propylpyridine.

$^1$H NMR (400 MHz, CDCl$_3$): δ 6.94 (s, 1H), 6.81 (s, 1H), 5.85 (s, 2H), 2.73 (t, 2H, J=7 Hz), 2.36 (s, 3H), 2.10 (s, 6H), 1.74 (sextet, 2H, J=7 Hz), 0.93 (t, 3H, J=7 Hz). Mass spectrum (FAB): m/e=229 (M+1).

Step B: 2-Amino-4-methyl-6-propylpyridine.

By analogy to Example 56, Step B, 4-methyl-2-(2,5-dimethylpyrrol-1-yl)-6-propylpyridine was treated with 4,6 equivalents of hydroxylamine hydrochloride and 2.8 equivalents of potassium hydroxide in refluxing ethanol/water to yield 2-amino-4-methyl-6-propylpyridine.

$^1$H NMR (400 MHz, CDCl$_3$): δ 6.33 (s, 1H), 6.13 (s, 1H), 4.27 (bs, 2H), 2,51 (t, 2H, J=7 Hz), 2.17 (s, 3H), 1.66 (sextet, 2H, J=7 Hz), 0.93 (t, 3H, J=7 Hz). Mass spectrum (FAB): m/e 151 (M+1).

EXAMPLE 69

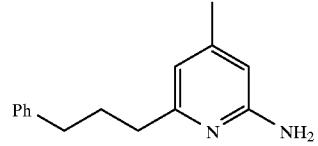

2-Amino-4-methyl-6-(3-phenylpropyl)pyridine

Step A: 4-Methyl-2-(2,5-dimethylpyrrol-1-yl)-6-(3-phenylpropyl)pyridine.

By analogy to Example 53, Step B, the anion of 4,6-dimethyl-2-(2,5-dimethylpyrrol-1-yl)pyridine was alkylated with (2-bromoethyl)benzene to give 4-methyl-2-(2,5-dimethylpyrrol-1-yl)-6-(3-phenylpropyl)pyridine.

$^1$H NMR (400 MHz, CDCl$_3$): δ 7.26 (t, 2H, J=7 Hz), 7.19–7.13 (m, 3H), 6.93 (s, 1H), 6.82 (s, 1H, 5.85 (s, 2H), 2.79 (t, 2H, J=7 Hz), 2.64 (t, 2H, J=7 Hz), 2.36 (s, 3H), 2.10 (s, 6H), 2.06 (quintet, 2H, J=7 Hz). Mass spectrum (FAB): m/e=305 (M+1).

Step B: 2-Amino-4-methyl-6-(3-phenylpropyl)pyridine.

By analogy to Example 56, Step B, 4-methyl-2-(2,5-dimethylpyrrol-1-yl)-6-(3-phenylpropyl)pyridine was treated with 4.6 equivalents of hydroxylamine hydrochloride and 2.8 equivalents of potassium hydroxide in refluxing ethanol/water to yield 2-amino-4-methyl-6-(3-phenylpropyl)pyridine as a yellow oil which spontaneously crystallized.

$^1$H NMR (400 MHz, CDCl$_3$): δ 7.28–7.22 (m, 2H), 7.20–7.12 (m, 3H), 6.33 (s, 1H), 6.14 (s, 1H), 4.26 (bs, 2H), 2.65 (t, 2H, J=8 Hz), 2,59 (t, 2H, J=8 Hz), 2.17 (s, 3H), 2.04–1.93 (m, 2H). Mass spectrum (FAB): m/e=227 (M+1). Calc. for C$_{15}$H$_{18}$N$_2$: 79.61% C, 8.02% H, 12.38% N. Found: 79.45% C, 7.96% H, 12.34% N.

EXAMPLE 70

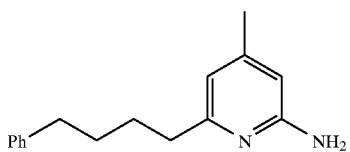

2-Amino-4-methyl-6-(4-phenylbutyl)pyridine
Step A: 4-Methyl-2-(2,5-dimethylpyrrol-1-yl)-6-(4-phenylbutyl)pyridine.

By analogy to Example 53, Step B, the anion of 4,6-dimethyl-2-(2,5-dimethylpyrrol-1-yl)pyridine was alkylated with 1-bromo-3-phenylpropane to give 4-methyl-2-(2,5-dimethylpyrrol-1-yl)-6-(4-phenylbutyl)pyridine.

$^1$H NMR (400 MHz, CDCl$_3$): δ 7.27–7.21 (m, 2H), 7.17–7.12 (m, 3H), 6.91 (s, 1H), 6.81 (s, 1H), 5.85 (s, 2H), 2.77 (t, 2H, J=7 Hz), 2.62 (t, 2H, J=7 Hz), 2.35 (s, 3H), 2.09 (s, 6H), 1.78 (quintet, 2H, J=7 Hz), 1.64 (quintet, 2H, J=7 Hz). Mass spectrum (FAB): m/e=319 (M+1). Caic. for C$_{22}$H$_{26}$N$_2$: 82.97% C, 8.23% H, 8.80% N. Found: 82.78% C, 8.03% H, 8.58% N.

Step B: 2-Amino-4-methyl-6-(4-phenylbutyl)pyridine.

By analogy to Example 56, Step B, 4-methyl-2-(2,5-dimethylpyrrol-1-yl)-6-(4-phenylbutyl)pyridine was treated with 4,6 equivalents of hydroxylamine hydrochloride and 2.8 equivalents of potassium hydroxide in refluxing ethanol/water to yield 2-amino-4-methyl-6-(4-phenylbutyl)pyridine as a yellow oil.

$^1$H NMR (400 MHz, CDCl$_3$): δ 7.24 (t, 2H, J=7 Hz), 7.17–7.12 (m, 3H), 6.31 (s, 1H), 6.13 (s, 1H), 4.44 (bs, 2H), 2.62 (t, 2H, J=7 Hz) 2,56 (t, 2H, J=7 Hz, 2.16 (s, 3H), 1.74–1.60 (m, 4H). Mass spectrum (FAB): m/e=241 (M+1).

EXAMPLE 71

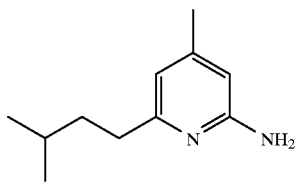

2-Amino-4-methyl-6-(3-methylbutyl)pyridine
Step A: 4-Methyl-6-(3-methylbutyl)-2-(2,5-dimethylpyrrol-1-yl)pyridine.

A solution prepared by the addition of 1.58 mL (2.85 mmol) of 1.8 M phenyllithium in 70:30 cyclohexane/diethyl ether to 4.0 mL of diethyl ether was stirred at –10° C. 4,6-Dimethyl-2-(2,5-dimethylpyrrol-1-yl)pyridine (500 mg, 2.5 mmol) was added as a solution in 1.7 mL of diethyl ether and the mixture was stirred 1h at –5 to –10° C. The red solution was then cooled to –45° C. and 0.354 mL (566 mg, 3.08 mmol) of 1-iodo-2-methylpropane was added in one portion. The reaction was warmed slowly to 10° C., stirring a total 2 h after addition of the iodide. The reaction was then quenched with 10 mL of saturated aqueous ammonium chloride and extracted with 30 mL of ethyl acetate. The organic phase was washed with 10 mL of saturated aqueous sodium chloride, dried over sodium sulfate and concentrated to give a yellow oil. Purification by flash column chromatography on silica gel, eluting with dichloromethane/hexane yielded 330 mg (52% yield) of 4-methyl-6-(3-methylbutyl)-2-(2,5-dimethylpyrrol-1-yl)pyridine as a yellow oil.

$^1$H NMR (400 MHz, CDCl$_3$): δ 6.95 (s, 1H), 6.81 (s, 1H), 5.86 (s, 2H), 2.67 (t, 2H, J=7 Hz), 2.36 (s, 3H), 2.10 (s, 6H), 1.63–1.51 (m, 3H), 0.92 (d, 6H, J=6 Hz). Mass spectrum (FAB): m/e=257 (M+1).

Step B: 2-Amino-4-methyl-6-(3-methylbutyl)pyridine.

By analogy to Example 56, Step B, 4-methyl-6-(3-methylbutyl)-2-(2,5-dimethylpyrrol-1-yl)pyridine was treated with 4.6 equivalents of hydroxylamine hydrochloride and 2.8 equivalents of potassium hydroxide in refluxing ethanol/water to yield 2-amino-4-methyl-6-(3-methylbutyl)pyridine as an amber oil.

$^1$H NMR (400 MHz, CDCl$_3$): δ 6.35 (s, 1H), 6.13 (s, 1H), 4.24 (bs, 2H), 2,56.2.51 (m, 2H), 2.17 (s, 3H), 1.64–1.48 (m, 3H), 0.91 (d, 6H, J=6 Hz). Mass spectrum (FAB): m/e=179 (M+1). Calc. for C$_{11}$H$_{18}$N$_2$: 74.11% C, 10.19% H, 15.71% N. Found: 73.82% C, 10.24% H, 15.63% N.

EXAMPLE 72

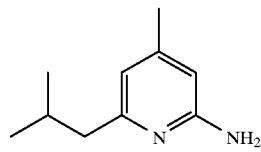

2-Amino-4-methyl-6-(2-methylpropyl)pyridine
Step A: 4-Methyl-6-(2-methylpropyl)2-(2,5-dimethylpyrrol-1-yl)pyridine.

By analogy to Example 71, Step A, the anion of 4,6-dimethyl-2-(2,5-dimethylpyrrol-1-yl)pyridine was alkylated with 2-iodopropane to give 4-methyl-6-(2-methylpropyl)-2-(2,5-dimethylpyrrol-1-yl)pyridine.

$^1$H NMR (400 MHz, CDCl$_3$): δ 6.92 (s, 1H), 6.81 (s, 1H), 5.85 (s, 2H), 2.62 (d, 2H, J=7 Hz), 2.36 (s, 3H), 2.18–2.05 (m, 1H), 2.08 (s, 6H), 0.90 (d, 6H, J=7 Hz). Mass spectrum (FAB): m/e=243 (M+1).

Step B: 2-Amino-4-methyl-6-(2-methylpropyl)pyridine.

By analogy to Example 56, Step B, 4-methyl-6-(2-methylpropyl)-2-(2,5-dimethylpyrrol-1-yl)pyridine was treated with 4.6 equivalents of hydroxylamine hydrochloride and 2.8 equivalents of potassium hydroxide in refluxing ethanol/water to yield 2-amino-4-methyl-6-(2-methylpropyl)pyridine as a white solid.

$^1$H NMR (400 MHz, CDCl$_3$): δ 6.30 (s, 1H), 6.13 (s, 1H), 4.24 (bs, 2H), 2.39 (d, 2H, J=7 Hz), 2.17 (s, 3H), 2.08–1.94 (m, 1H), 0.89 (d, 6H, J=7 Hz). Mass spectrum (FAB): m/e=165 (M+1).

EXAMPLE 73

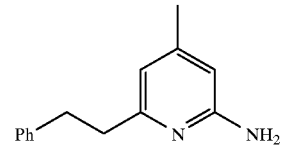

2-Amino-4-methyl-6-(2-phenylethyl)pyridine
Step A: 4-Methyl-2-(2,5-dimethylpyrrol-1-yl)-6-(2-phenylethyl)pyridine.

By analogy to Example 71, Step A, the anion of 4,6-dimethyl-2-(2,5-dimethylpyrrol-1-yl)pyridine was alkylated with benzylbromide to give 4-methyl-2-(2,5-dimethylpyrrol-1-yl)-6-(2-phenylethyl)pyridine as an amber oil.

$^1$H NMR (400 MHz, CDCl$_3$): δ 7.28–7.22 (m, 2H), 7.19–7.14 (m, 3H), 6.89 (s, 1H), 6.83 (s, 1H), 5.86 (s, 2H), 3.10–3.00 (m, 4H), 2.14 (s, 3H), 2.11 (s, 6H). Mass spectrum (FAB): m/e=291 (M+1).

Step B: 2-Amino-4-methyl-6-(2-phenylethyl)pyridine.

By analogy to Example 56, Step B, 4-methyl-2-(2,5-dimethylpyrrol-1-yl)-6-(2-phenylethyl)pyridine was treated with 4.6 equivalents of hydroxylamine hydrochloride and 2.8 equivalents of potassium hydroxide in refluxing ethanol/water to yield 2-amino-4-methyl-6-(2-phenylethyl)pyridine as a colorless oil.

$^1$H NMR (400 MHz, CDCl$_3$): δ 7.28–7.16 (m, 5H), 6.32 (s, 1H), 6.16 (s, 1H), 4.29 (bs, 2H), 2.99–2.93 (m, 2H), 2.87–2.81 (m, 2H), 2.18 (s, 3H). Mass spectrum (FAB): m/e=213 (M+1).

EXAMPLE 74

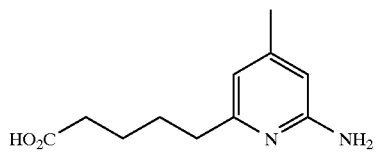

5-(6-Amino-4-methyl-2-pyridinyl)pentanoic acid hydrochloride

Step A: Methyl 5-(4-methyl-6-(2,5-dimethylpyrrol-1-yl)-2-pyridinyl)pentanoate.

By analogy to Example 53, Step B, the anion of 4,6-dimethyl-2-(2,5-dimethylpyrrol-1-yl)pyridine was alkylated with trimethyl 4-bromoorthobutyrate. The crude product was purified by flash column chromatography on silica gel, eluting with 10% ethyl acetate in hexane to give the hydrolysis product of the orthoester intermediate. Methyl 5-(4-methyl-6-(2,5-dimethylpyrrol-1-yl)-2-pyridinyl)pentanoate was isolated as an amber oil in 49% yield.

$^1$H NMR (400 MHz, CDCl$_3$): δ 6.94 (s, 1H), 6.82 (s, 1H), 5.85 (s, 2H), 3.64 (s, 3H), 2.76 (t, 2H, J=7 Hz), 2.36 (s, 3H), 2.32 (t, 2H, J=7 Hz), 2.09 (s, 6H), 1.80–1.71 (m, 2H), 1.70–1.61 (m, 2H). Mass spectrum (FAB): m/e=301 (M+1). Calc. for C$_{18}$H$_{24}$N$_2$O$_2$: 71.97% C, 8.05% H, 9.63% N. Found: 71.80% C, 8.11% H, 9.63% N.

Step B: Methyl 5-(6-amino-4-methyl-2-pyridinyl)pentanoate.

Methyl 5-(4-methyl-6-(2,5-dimethylpyrrol-1-yl)-2-pyridinyl)pentanoate (330 mg, 1.10 mmol) was dissolved in 6.0 mL of 95% ethanol, and 1.0 mL of water was added followed by 199 mg (3.08 mmol) of 87% potassium hydroxide. After 2 h, an additional 1 mL of water was added along with 351 mg (5.06 mmol) of hydroxylamine hydrochloride. The solution was heated to reflux for 20 h, then cooled and concentrated. The residue was dissolved in 15 mL of 2 N aqueous hydrochloric acid and washed with 2×10 mL of ethyl ether. The aqueous layer was evaporated and triturated with 3×5 mL of methanol. The methanol extracts were evaporated to give 619 mg of partially crystalline material. A portion (495 mg) of this material was dissolved in 6.0 mL of methanol along with 510 mg (2.68 mmol) of p-toluenesulfonic acid and heated to reflux for 20 h. The reaction was cooled and concentrated and the residue was partitioned between 25 mL of saturated aqueous sodium bicarbonate and 50 mL of ethyl acetate. The aqueous layer was extracted with 2×25 mL of ethyl acetate. The combined organic layers were washed with 50 mL of saturated aqueous sodium chloride, dried (sodium sulfate), decanted, and evaporated. The residue was purified by flash column chromatography on 20 g of silica gel, eluting with 500 mL of 50% ethyl acetate in dichloromethane to give 119 mg (61% yield) of methyl 5-(6-amino-4-methyl-2-pyridinyl)pentanoate as an amber oil.

$^1$H NMR (400 MHz, CD$_3$OD): δ 6.63 (s, 1H), 6.43 (s, 1H), 3.64 (s, 3H), 2.51 (t, 2H, J=7 Hz), 2.33 (t, 2H, J=7 Hz), 2.17 (s, 3H), 1.69–1.57 (m, 4H). Mass spectrum (FAB): m/e=223 (M+1).

Step C: 5-(6-Amino-4-methyl-2-pyridinyl)pentanoic acid hydrochloride.

A mixture of methyl 5-(6-amino-4-methyl-2-pyridinyl) pentanoate (119 mg, 0.536 mmol) in 10 mL of 2.0 N hydrochloric acid was refluxed for 3 h. After cooling to room temperature, the reaction was extracted with 2×10 mL of dichloromethane and the aqueous phase was concentrated in vacuo to give 134 mg of 5-(6-amino-4-methyl-2-pyridinyl) pentanoic acid hydrochloride as a pink solid.

$^1$H NMR (400 MHz, CD$_3$OD): δ 6.64 (s, 1H), 6.63 (s, 1H), 2.72 (t, 2H, J=7 Hz), 2.38–2.32 (m, 5H), 1.78–1.61 (m, 4H). Mass spectrum (FAB): m/e=209 (M+1). Calc. for C$_{11}$H$_{17}$ClN$_2$O$_2$: 53.99% C, 7.00% H, 11.45% N, 14.49% Cl. Found: 53.60% C, 7.07% H, 11.27% N, 14.71% Cl.

EXAMPLE 75

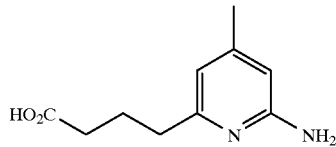

4-(6-Amino-4-methyl-2-pyridinyl)butanoic acid hydrochloride

Step A: Diethyl (2-(4-methyl-6-(2,5-dimethylpyrrol-1-yl)-2-pyridinyl)ethyl)malonate.

Diethyl malonate (229 mg, 1.43 nimol) was added dropwise via syringe over 5 min to a suspension of sodium hydride (52 mg of 60% oil dispension, 1.30 mmol) in 2.0 mL of N,N-dimethylformamide, and the mixture was stirred at room temperature until it became clear. A solution of 200 mg (0.65 mmol) of 6-(2-methanesulfonyloxyethyl)-4-methyl-2-(2,5-dimethylpyrrol-1-yl)pyridine (from Example 59, Step A) in 1.0 mL of N,N-dimethylformamide was added to the reaction followed by 72 mg (0.19 mmol) of tetrabutylammonium iodide, and the reaction was stirred at room temperature for 3 h followed by 15 h at 65° C. The reaction was diluted with ethyl acetate (30 mL) and washed with 15 mL of saturated aqueous sodium bicarbonate and 15 mL of saturated aqueous sodium chloride. The combined aqueous layers were extracted with 30 ml of ethyl acetate and the combined organic layers were dried (sodium sulfate), decanted and concentrated. The residue was purified by flash column chromatography on 50 g of silica gel, eluting with 500 mL of 5% ethyl acetate/hexane and 700 mL of of 10% ethyl acetate/hexane to give 97 mg (40% yield) of diethyl (2-(4-methyl-6-(2,5-dimethylpyrrol-1-yl)-2-pyridinyl)ethyl) malonate as a yellow oil.

$^1$H NMR (400 MHz, CDCl$_3$): δ 6.95 (s, 1H), 6.84 (s, 1H), 5.85 (s, 2H), 4.18 (q, 4H, J=7 Hz), 3.34 (t, 1H, J=7 Hz), 2.81 (t, 2H, J=7 Hz), 2.36 (s, 3H), 2.33 (q, 2H, J=7 Hz), 2.10 (s, 6H), 1.25 (t, 6H, J=7 Hz). Mass spectrum (FAB): m/e=373 (M+1).

Step B: Dimethyl (2-(6-amino-4-methyl-2-pyridinyl)ethyl) malonate.

To a solution of diethyl (2-(4-methyl-6-(2,5-dimethylpyrrol-1-yl)-2-pyridinyl)ethyl)malonate (96 mg, 0.26 mmol) in 1.4 mL of ethanol was added 0.3 mL of water, followed by 105 mg of 87% potassium hydroxide (1.63 mmol). After the mixture had been stirred at room temperature for 7 h., additional water (0.3 mL) was added along with 166 mg (2.39 mmol) of hydroxylamine hydrochloride. The mixture was refluxed 12 h. After removing solvent in vacuo, the residue was dissolved into 10 mL of 2.0 N aqueous hydrochloric acid and washed with 2×10 mL of diethyl ether. The aqueous phase was concentrated and swirled with 3×1 mL of methanol. The methanol extracts were combined, filtered, and evaporated. The residue was dissolved in 5.0 mL of methanol along with 149 mg (0.78 mmol) of p-toluenesulfonic acid and heated to reflux for 16 h. The reaction was cooled and concentrated and the residue was partitioned between 15 mL of saturated aqueous sodium bicarbonate and 30 mL of ethyl acetate. The organic layer was washed with 15 mL of saturated aqueous sodium chloride, dried (sodium sulfate), decanted, and evaporated. The residue was purified by flash column chromatography on 10 g of silica gel, eluting with 200 mL of 40% ethyl acetate in dichloromethane and 200 ML of 50% ethyl acetate in dichloromethane to give 36 mg (52% yield) of dimethyl (2-(6-amino-4-methyl-2-pyridinyl)ethyl)malonate.

$^1$H NMR (400 MHz, CD$_3$OD): δ 6.32 (s, 1H), 6.25 (s, 1H), 3.72 (s, 6H), 3.42 (t, 1H, J=7 Hz), 2,53 (t, 2H, J=7 Hz), 2.22–2.12 (m, 5H). Mass spectrum (EI): m/e=266 (M$^+$).

Step C: 4-(6-Amino-4-methyl-2-pyridinyl)butanoic acid hydrochloride.

A mixture of dimethyl (2-(6-amino-4-methyl-2-pyridinyl) ethyl)malonate (34 mg, 0.13 mmol) in 2.0 mL of 2.0 N hydrochloric acid was refluxed for 8 h. After cooling to room temperature, the reaction was extracted with 2×15 mL of dichloromethane and the aqueous phase was concentrated in vacuo to give 17 mg (58% yield) of 4-(6-amino-4-methyl-2-pyridinyl)butanoic acid hydrochloride.

$^1$H NMR (400 MHz, CD$_3$OD): δ 6.66 (s,1H), 6.63 (s, 1H), 2.75 (t, 2H, J=7 Hz), 2.39 (t, 2H, J=7 Hz), 2.35 (s, 3H), 1.98 (quintet, 2H, J=7 Hz). Mass spectrum (FAB): m/e=195 (M+1).

EXAMPLE 76

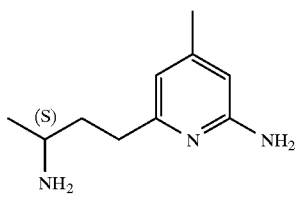

(S)-2-Amino-6-(3-aminobutyl)-4-methylpyridine

Step A: (S)-1-(2-Hydroxy-1-methylethyl)-2,5-dimethylpyrrole.

2,5-Hexanedione (3.6 mL, 30.7 mmol) was added to a solution of (S)-2-amino-1-propanol (2.44 g, 32.5 mmol) in 15 mL of methanol. The mixture was stirred at reflux for 2 h. After concentrating in vacuo, the residue was dissolved in 100 mL of ethyl acetate and washed with 50 1 mL of saturated aqueous sodium bicarbonate and 50 mL of saturated aqueous sodium chloride. The organic layer was dried (sodium sulfate), decanted, and evaporated to give a yellow solid. Flash column chromatography on 150 g of silica gel using 2.5 L of 15% ethyl acetate/hexane to furnish 4.53 g (96% yield) of (S)-1-(2-hydroxy-1-methylethyl)-2,5-dimethylpyrrole as a white solid.

$^1$H NMR (400 MHz, CD$_3$OD): δ 5.63 (s, 2H), 4.31 (sextet, 1H, J=7 Hz), 3.80 (dd, 1H, J=11, 7 Hz), 3.72 (dd, 1H, J=11, 7 Hz), 2.44 (s, 6H), 1.41 (d, 3H, J=7 Hz).

Step B: (S)-1-(2-Bromo-1-methylethyl)-2,5-dimethylpyrrole.

Triphenylphosphine (2.24 g, 8.50 mmol) was added in four portions over 10 minutes to an ice cooled mixture of (S)-1-(2-hydroxy-1-methylethyl)-2,5-dimethylpyrrole (1.0 g, 6.54 mmol) and carbon tetrabromide (3.03 g, 9.15 mmol) in 50 mL of acetonitrile. The mixture was stirred at 0° C. for 1.5 h, room temperature for 18 h, and 50° C. for 6 h. The solvent was removed in vacuo. The residue was purified by flash column chromatography on 70 g of silica gel, eluting with 1 L of 15% dichloromethane in hexane to give 1.22 g (85% yield) of (S)-1-(2-bromo-1-methylethyl)-2,5-dimethylpyrrole as a yellow liquid.

$^1$H NMR (400 MHz, CDCl$_3$): δ 5.75 (s, 2H), 4.46 (sextet, 1H, J=7 Hz), 3.65 (dd, 1H, J=11, 7 Hz), 3.61 (dd, 1H, J=11, 7 Hz), 2.26 (s, 6H), 1.60 (d,3H,J=7Hz).

Step C: (S)-4-Methyl-2-(2,5-dimethylpyrrol-1-yl)-6-(3-(2,5-dimethylpyrrol-1-yl)-3-methylpropyl)pyridine.

By analogy to Example 71, Step A, the anion of 4,6-dimethyl-2-(2,5-dimethylpyrrol-1-yl)pyridine was alkylated with (S)-1-(2-bromo-1-methylethyl)-2,5-dimethylpyrrole to give (S)-4-methyl-2-(2,5-dimethylpyrrol-1-yl)-6-(3-(2,5-dimethylpyrrol-1-yl)-3-methylpropyl)pyridine.

$^1$H NMR (400 MHz, CDCl$_3$): δ 6.83 (s, 1H), 6.79 (s, 1H), 5.87 (s, 2H), 5.72 (s, 2H), 4.18 (sextet, 1H, J=7 Hz), 2.69–2.54 (m, 2H), 2.36–2.06 (m, 17H), 1.44 (d, 3H, J=7 Hz). Mass spectrum (FAB): m/e=336 (M+1).

Step D: (S)-2-Amino-6-(3-aminobutyl)-4-methylpyridine.

By analogy to Example 56, Step B, (S)-4-methyl-2-(2,5-dimethylpyrrol-1-yl)-6-(3-(2,5-dimethylpyrrol-1-yl)-3-methylpropyl)pyridine was treated with 9.2 equivalents of hydroxylamine hydrochloride and 5.4 equivalents of potassium hydroxide in refluxing ethanol/water to yield (S)-2-amino-6-(3-aminopropyl)-4-methylpyridine $^1$H NMR (400 MHz, CDCl$_3$): δ 6.35 (s, 1H), 6.13 (s, 1H), 4.27 (bs, 2H), 2.89 (sextet, 1H, J=6 Hz), 2.66–2.51 (m, 2H), 2.17 (s, 3H), 1.75–1.58 (m, 2H), 1.45 (bs, 2H), 1.07 (d, 3H, J=6 Hz). Mass spectrum (FAB): m/e=180 (M+1).

EXAMPLE 77

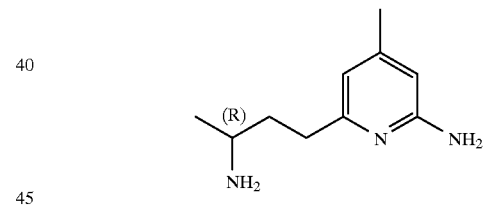

(R)-2-Amino-6-(3-aminobutyl)-4-methylpyridine

Step A: (R)-1-(2-Hydroxy-1-methylethyl)-2,5-dimethylpyrrole.

By analogy to Example 76, Step A, (R)-2-amino-1-propanol was converted into (R)-1-(2-hydroxy-1-methylethyl)-2,5-dimethylpyrrole.

$^1$H NMR (400 MHz, CDCl$_3$): 5.77 (s, 2H), 4.43–4.33 (m, 1H), 3.93 (dd, J=11, 9 Hz), 3.75 (dd, J=11, 6 Hz), 2.27 (s, 6H), 1.45 (d, 3H, J=7 Hz). Mass spectrum (FAB): m/e=154 (M+1).

Step B: (R)-1-(2-Bromo-1-methylethyl)-2,5-dimethylpyrrole.

By analogy to Example 76, Step B, (R)-1-(2-hydroxy-1-methylethyl)-2,5-dimethylpyrrole was converted into (R)-1-(2-bromo-1-methylethyl)-2,5-dimethylpyrrole.

$^1$H NMR (400 MHz, CDCl$_3$): δ 5.75 (s, 2H), 4.46 sextet, 1H, J=7 Hz), 3.65 (dd, 1H, J=11, 7 Hz), 3.61 (dd, 1H, J=11, 7 Hz), 2.26 (s, 6H), 1.60 (d, 3H, J=7 Hz). Mass spectrum (FAB): m/e=216 (M+1).

Step C: (R-4-Methyl)-2-(2,5-dimethylpyrrol-1-yl)-6-(3-(2, 5-dimethylpyrrol-1-yl)-3-methylpropyl)pyridine.

By analogy to Example 76, Step A, the anion of 4,6-dimethyl-2-(2,5-dimethylpyrrol-1-yl)pyridine was alkylated with (R)-1-(2-bromo-1-methylethyl)-2,5-dimethylpyrrole to give (R)-4-methyl-2-(2,5-dimethylpyrrol-1-yl)-6-(3-(2,5-dimethylpyrrol-1-yl)-3-methylpropyl)pyridine.

$^1$H NMR (400 MHz, CDCl$_3$): δ 6.83 (d, 1H), 6.79 (s, 1H), 5.87 (s, 2H), 5.72 (s, 2H), 4.18 (sextet, 1H, J=7 Hz), 2.69–2.54 (m, 2H), 2.36–2.06 (m, 17H), 1.44 (d, 3H, J=7 Hz). Mass spectrum (FAB): m/e=336 (M+1).

Step D: (R)-2-Amino-6-(3-aminobutyl)-4-methylpyridine

By analogy to Example 56, Step B, (R)-4-methyl-2-(2,5-dimethylpyrrol-1-yl)-6-(3-(2,5-dimethylpyrrol-1-yl)-3-methylpropyl)pyridine was treated with 9.2 equivalents of hydroxylamine hydrochloride and 5.4 equivalents of potassium hydroxide in refluxing ethanol/water to yield (R)-2-amino-6-(3-aminopropyl)-4-methylpyridine $^1$H NMR (400 MHz, CDCl$_3$): δ 6.35 (s, 1H), 6.13 (s, 1H), 4.27 (bs, 2H), 2.89 (sextet, 1H, J=6 Hz), 2.66–2.51 (m, 2H), 2.17 (s, 3H), 1.75–1.58 (m, 2H), 1.49 (br, 2H), 1.08 (d, 3H, J=6 Hz). Mass spectrum (FAB): m/e=180 (M+1).

EXAMPLE 78

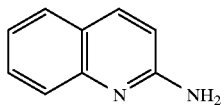

2-Aminoquinoline

The title compound is commercially available from Maybridge Chemical Comp., Ltd., Cornwall, UK.

EXAMPLE 79

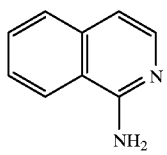

1-Aminoisoquinoline

The title compound is commercially available from Aldrich Chemical Co., Milwaukee, Wis. 53233.

EXAMPLE 80

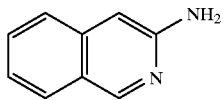

3-Aminoisoquinoline

The title compound is commercially available from Aldrich Chemical Co. (SALOR), Milwaukee, Wis. 53233.

What is claimed is:

1. A method for inhibiting the activity of nitric oxide synthases comprising administering to a subject suffering from a nitric oxide synthase mediated disease, a non-toxic therapeutically effective amount of a compound of Formula (I)

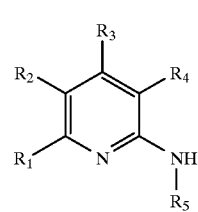

or a pharmaceutically acceptable salt thereof wherein:
$R_1$, $R_2$, $R_3$ and $R_4$ are each independently selected from the group consisting of:
(a) hydrogen,
(b) hydroxy,
(c) amino,
(d) carboxyl,
(e) aminocarbonyl,
(f) cyano,
(g) nitro,
(h) halo, where halo is selected from fluoro, chloro, bromo, and iodo,
(i) trifluoromethyl,
(j) $C_{1-12}$alkyl,
(k) $C_{2-12}$alkenyl,
(l) $C_{2-12}$alkynyl,
(m) $C_{1-12}$alkoxy,
(n) $C_{1-12}$alkylcarbonyl,
(o) $C_{1-12}$alkoxycarbonyl,
(p) $C_{1-12}$alkylaminocarbonyl,
(q) mono- and di-$C_{1-12}$alkylamino,
(r) $C_{1-12}$alkylthio,
(s) aryl, where aryl is selected from phenyl and naphthyl,
(t) aryloxy, where aryl is selected from phenyl and naphthyl,
(u) arylthio, where aryl is selected from phenyl and naphthyl,
(v) aryl$C_{1-6}$alkyl, where aryl is selected from phenyl and naphthyl,
(w) cycloalkyl, wherein the cycloalkyl is a 5- to 10-membered monocyclic ring which optionally contains 1 or 2 heteroatoms selected from S, O, and N,
(x) heteroaryl, wherein heteroaryl is selected from the group consisting of:
(1) pyridyl,
(2) pyrrolyl,
(3) furanyl,
(4) thienyl,
(5) isothiazolyl,
(6) imidazolyl,
(7) benzimidazolyl,
(8) tetrazolyl,
(9) pyrazinyl,
(10) pyrimidyl,
(11) quinolyl,
(12) isoquinolyl,
(13) benzofuranyl,
(14) isobenzofuryl,
(15) benzothienyl,
(16) pyrazolyl,
(17) pyrazinyl
(18) indolyl,
(19) isoindolyl,
(20) purinyl,

(21) carbazolyl,
(22) isoxazolyl,
(23) thiazolyl,
(24) triazolyl
(25) oxazolyl,
(26) oxadiazolyl,
(27) thiadiazolyl,
(28) benzthiazolyl and
(29) benzoxazolyl, and
(y) heteroaryl$C_{1-6}$alkyl, where heteroaryl is defined above in item (x),
each of (j) to (y) being optionally mono- or di-substituted, the substituents being independently selected from the group consisting of:
(1) hydroxy,
(2) $C_{1-6}$alkyl,
(3) $C_{1-6}$alkoxy,
(4) amino,
(5) mono- and di-$C_{1-6}$alkylamino,
(6) carboxyl
(7) $C_{1-6}$alkylthio,
(8) —$S(O)_k$-$C_{1-3}$alkyl, where k is 1 or 2,
(9) $C_{1-6}$alkoxycarbonyl,
(10) halo selected from fluoro, chloro, bromo, and iodo,
(11) oxo,
(12) amidino and
(13) guanidino; and
$R_5$ is selected from the group consisting of:
(a) hydrogen,
(b) $C_{1-12}$alkyl,
(c) $C_{2-12}$alkenyl,
(d) $C_{2-12}$alkynyl,
(e) aryl, wherein the aryl group is as defined above,
(f) aryl$C_{1-6}$alkyl, wherein the aryl group is as defined above,
(g) heteroaryl, wherein heteroaryl is as defined above,
(h) heteroaryl$C_{1-6}$alkyl, wherein heteroaryl is as defined above, and
(i) cycloalkyl, wherein the cycloalkyl is a 5- to 10-membered monocyclic ring which optionally contains 1 or 2 heteroatoms selected from the group consisting of S, O and N,
each of (b) to (i) being optionally mono- or di-substituted, the substituents being independently selected from the group consisting of:
(1) hydroxy,
(2) $C_{1-6}$alkyl,
(3) $C_{1-6}$alkoxy,
(4) amino,
(5) mono- and di-$C_{1-6}$alkylamino,
(6) carboxyl
(7) $C_{1-6}$alkylthio,
(8) —$S(O)_k$—$C_{1-3}$alkyl, where k is 1 or 2,
(9) $C_{1-6}$alkoxycarbonyl,
(10) halo selected from fluoro, chloro, bromo, and iodo,
(11) oxo,
(12) amidino and
(13) guanidino,
with the proviso that $R_2$ is other than aryl, heteroaryl, aryl$C_{1-4}$alkyl, or heteroaryl$C_{1-4}$alkyl.

2. A method for inhibiting the activity of nitric oxide synthases comprising administering to a subject suffering from a nitric oxide synthase mediated disease, a non-toxic therapeutically effective amount of a compound of Formula (I)

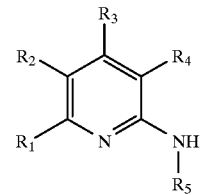

or a pharmaceutically acceptable salt thereof wherein:

$R_1$, $R_2$, $R_3$ and $R_4$ are each independently selected from the group consisting of:
(a) hydrogen,
(b) hydroxy,
(c) amino,
(d) cyano,
(e) fluoro, chloro, bromo, and iodo,
(f) trifluoromethyl,
(g) $C_{1-6}$alkyl,
(h) $C_{1-6}$alkoxy,
(i) $C_{1-6}$alkylthio,
(j) $C_{1-6}$alkylcarbonyl,
(k) mono- and di-$C_{1-6}$alkylamino,
(l) aryl, where aryl is phenyl and naphthyl,
(m) aryloxy, where aryl is phenyl and naphthyl,
(n) cycloalkyl, wherein the cycloalkyl is a 5-, 6-, or 7-membered monocyclic ring which optionally contains 1 or 2 heteroatoms selected from S, O, and N, and
(o) heteroaryl, wherein heteroaryl is selected from the group consisting of:
(1) pyridyl,
(2) furanyl,
(3) thienyl,
(4) pyrazinyl,
(5) pyrimidyl,
(6) thiazolyl and
(7) triazolyl,
each of (g) to (o) being optionally mono- or di-substituted, the substituents being independently selected from the group consisting of:
(1) hydroxy,
(2) $C_{1-4}$alkyl,
(3) $C_{1-3}$alkoxy,
(4) $C_{1-3}$alkylthio,
(5) mono- and di-$C_{1-3}$alkylamino,
(7) —$S(O)_k$—$C_{1-3}$alkyl, where k is 1 or 2,
(8) —$C(O)$—$O$—$C_{1-3}$alkyl,
(9) halo selected from fluoro, chloro and bromo,
(10) amino and
(11) carboxyl, and one of $R_1$ and $R_2$, $R_2$ and $R_3$ and $R_3$ and $R_4$ is taken together to form a 5-, 6- or 7-membered saturated monocyclic ring which together with the atoms to which $R_1$ and $R_2$, or $R_2$ and $R_3$ or $R_3$ and $R_4$ are attached there is formed a bicyclic ring according to Formulae (IIa–IIc),

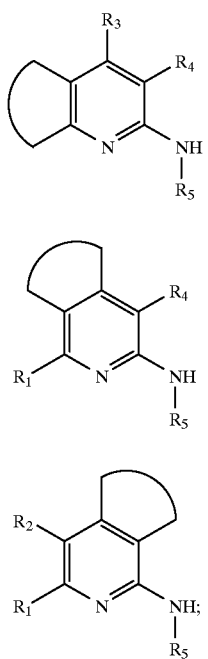

(IIa)

(IIb)

(IIc)

and $R_5$ is selected from the group consisting of:
 (a) hydrogen,
 (b) $C_{1-6}$alkyl,
 (c) aryl, wherein the aryl group is phenyl and naphthyl,
 (d) aryl$C_{1-6}$alkyl, wherein the aryl group is phenyl and naphthyl,
 (e) heteroaryl, wherein heteroaryl is as defined above,
 (f) heteroaryl$C_{1-6}$alkyl, wherein heteroaryl is as defined above, and
 (g) cycloalkyl, wherein the cycloalkyl is a 5-, 6-, or 7-membered monocyclic ring which optionally contains 1 or 2 heteroatoms selected from S, O, and N,
  each of (b) to (g) being optionally mono- or di-substituted, the substituents being independently selected from the group consisting of:
   (1) hydroxy,
   (2) $C_{1-4}$alkyl,
   (3) $C_{1-3}$alkoxy,
   (4) $C_{1-3}$alkylthio,
   (5) mono- and di-$C_{1-3}$alkylamino,
   (7) —S(O)$_k$—$C_{1-3}$alkyl, where k is 1 or 2,
   (8) —C(O)—O—$C_{1-3}$alkyl and
   (9) halo selected from fluoro, chloro and bromo.

3. A method for inhibiting the activity of nitric oxide synthases comprising administering to a subject suffering from a nitric oxide synthase mediated disease, a non-toxic therapeutically effective amount of a compound of Formula (I)

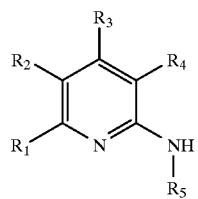

(I)

or a pharmaceutically acceptable salt thereof wherein:

$R_1$, $R_2$, $R_3$ and $R_4$ are each independently selected from the group consisting of:
 (a) hydrogen,
 (b) hydroxy,
 (c) amino,
 (d) cyano,
 (e) fluoro, chloro, bromo, and iodo,
 (f) trifluoromethyl,
 (g) $C_{1-6}$alkyl,
 (h) $C_{1-6}$alkoxy,
 (i) $C_{1-6}$alkylthio,
 (j) $C_{1-6}$alkylcarbonyl,
 (k) mono- and di-$C_{1-6}$alkylamino,
 (l) aryl, where aryl is phenyl and naphthyl,
 (m) aryloxy, where aryl is phenyl and naphthyl,
 (n) cycloalkyl, wherein the cycloalkyl is a 5-, 6-, or 7-membered monocyclic ring which optionally contains 1 or 2 heteroatoms selected from S, O, and N, and
 (o) heteroaryl, wherein heteroaryl is selected from the group consisting of:
  (1) pyridyl,
  (2) furanyl,
  (3) thienyl,
  (4) pyrazinyl,
  (5) pyrimidyl,
  (6) thiazolyl and
  (7) triazolyl,
  each of (g) to (o) being optionally mono- or di-substituted, the substituents being independently selected from the group consisting of:
   (1) hydroxy,
   (2) $C_{1-4}$alkyl,
   (3) $C_{1-3}$alkoxy,
   (4) $C_{1-3}$alkylthio,
   (5) mono- and di-$C_{1-3}$alkylamino,
   (7) —S(O)$_k$—$C_{1-3}$alkyl, where k is 1 or 2,
   (8) —C(O)—O—$C_{1-3}$alkyl,
   (9) halo selected from fluoro, chloro and bromo,
   (10) amino and
   (11) carboxyl, and one of $R_1$ and $R_2$, $R_2$ and $R_3$ and $R_3$ and $R_4$ is taken together to form a 5-, 6- or 7-membered saturated monocyclic ring containing 1 or 2 heteroatoms which together with the atoms to which $R_1$ and $R_2$, or $R_2$ and $R_3$ or $R_3$ and $R_4$ are attached there is formed a bicyclic ring according to Formulae (IIa–IIc), the heteroatoms being selected from the group consisting of O, S and N,

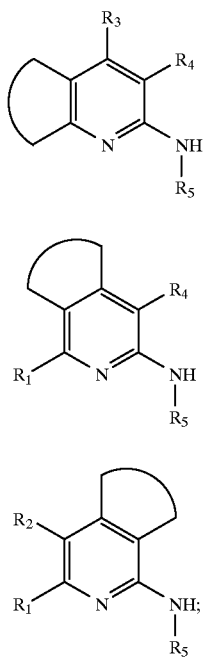

R₅ is selected from the group consisting of:
(a) hydrogen,
(b) C₁₋₆alkyl,
(c) aryl, wherein the aryl group is phenyl and naphthyl,
(d) arylC₁₋₆alkyl, wherein the aryl group is phenyl and naphthyl,
(e) heteroaryl, wherein heteroaryl is as defined above,
(f) heteroarylC₁₋₆alkyl, wherein heteroaryl is as defined above, and
(g) cycloalkyl, wherein the cycloalkyl is a 5-, 6-, or 7-membered monocyclic ring which optionally contains 1 or 2 heteroatoms selected from S, O, and N, each of (b) to (g) being optionally mono- or di-substituted, the substituents being independently selected from
(1) hydroxy,
(2) C₁₋₄alkyl,
(3) C₁₋₃alkoxy,
(4) C₁₋₃alkylthio,
(5) mono- and di-C₁₋₃alkylamino,
(7) —S(O)ₖ—C₁₋₃alkyl, where k is 1 or 2,
(8) —C(O)—O—C₁₋₃alkyl and
(9) halo selected from fluoro, chloro and bromo.

4. A method for inhibiting the activity of nitric oxide synthases comprising administering to a subject suffering from a nitric oxide synthase mediated disease, a non-toxic therapeutically effective amount of a compound selected from the group consisting of:
(a) 2-amino-3-benzylurea-4-picoline,
(b) 2-amino-3-methoxypyridine,
(c) 2-amino-3-methylthio-4-picoline,
(d) 2-amino-4-methylthiomethylpyridine,
(e) 2-amino-3-hydroxymethyl-4-picoline,
(f) 2-amino-3-ethyl-4-picoline dihydrochloride,
(g) 2-amino-3-methoxymethyl-4-picoline dihydrochloride,
(h) 2-amino-3-n-propyl-4-picoline dihydrochloride,
(i) 2-amino-3-dimethylamino-4-picoline trihydrochloride,
(j) 2-amino-3-chloro-4-picoline,
(k) 2-amino-5-chloro-4-picoline,
(l) 2,5-diamino-4-picoline,
(m) 5-acetylamino-2-amino-4-picoline,
(n) 2-amino-5-ethynyl-4-methyl-pyridine,
(o) 2-amino-4-methyl-5-pentyl-pyridine,
(p) 4-methylthio-2-aminopyridine,
(q) 4-chloro-6-methoxycarbonyl-2-aminopyridine,
(r) 4,6-dimethyl-5-ethenyl-2-aminopyridine,
(s) 2.4-diaminopyridine dihydrochloride,
(t) 2-amino-5-phenylpyridine,
(u) 2-amino-4-methyl-5-phenylpyridine,
(v) 2-amino-5-bromo-4-methylpyridine,
(w) 2-amino-5-cyano-4-methylpyridine,
(x) 2-amino-5-carboxy-4-methylpyridine,
(y) 2-amino-5-methoxycarbonyl-4-methylpyridine,
(z) 2-amino-5-aminomethyl-4-methylpyridine dihydrochloride,
(aa) 2-amino-5-acetamidomethyl-4-methylpyridine,
(ab) 2-amino-5-hydroxymethyl-4-methylpyridine,
(ac) 2-(2-amino-3-pyridinoxy)-ethyl-(S)-glycine dihydrochloride,
(ad) 2-amino-4,5-dimethylpyridine hydrochloride,
(ae) 2-amino-6-(3-buten-1-yl)-4-methylpyridine,
(af) 2-amino-6-ethyl-4-methylpyridine,
(ag) 2-amino-4-methyl-6-(1-methylethyl)pyridine,
(ah) 2-amino-6-(4-aminobutyl)-4-methylpyridine,
(ai) 6-(4-acetamidobutyl)-2-amino-4-methylpyridine,
(aj) 2-amino-6-(2-hydroxyethyl)-4-methylpyridine,
(ak) α-(2-(6-amino-4-methylpyrid-2-yl) ethyl)glycine dihydrochloride,
(al) 2-amino-5-ethylpyridine,
(am) 2-amino-6-benzylpyridine,
(an) 2-amino-6,7-dihydro-(5H)-pyrindine,
(ao) 2-amino-6-(3-aminopropyl)-4-methylpyridine,
(ap) 2-amino-6-(2-aminoethyl)-4-methylpyridine,
(aq) 2-amino-4-methyl-6-propylpyridine,
(ar) 2-amino-4-methyl-6-(3-phenylpropyl)pyridine,
(as) 2-amino-4-methyl-6-(4-phenylbutyl)pyridine,
(at) 2-amino-4-methyl-6-(3-methylbutyl)pyridine,
(au) 2-amino-4-methyl-6-(2-methylpropyl)pyridine,
(av) 2-amino-4-methyl-6-(2-phenylethyl)pyridine,
(aw) 5-(6-amino-4-methyl-2-pyridinyl)pentanoic acid hydrochloride,
(ax) 4-(6-amino-4-methyl-2-pyridinyl)butanoic acid hydrochloride,
(ay) (S)-2-amino-6-(3-aminobutyl)-4-methylpyridine, and
(az) (R)-2-Amino-6-(3-aminobutyl)-4-methylpyridine,
or a pharmaceutically acceptable salt thereof.

* * * * *